(12) United States Patent
Neumann et al.

(10) Patent No.: US 8,445,280 B2
(45) Date of Patent: *May 21, 2013

(54) METHOD FOR CREATING PERFUSABLE MICROVESSEL SYSTEMS

(75) Inventors: Thomas Neumann, Seattle, WA (US); Anna Tourovskaia, Mountlake Terrace, WA (US); Mark E. Fauver, Seattle, WA (US); Julia Oi Yan Yu, Kirkland, WA (US)

(73) Assignee: Nortis, Inc., Seattle, WA (US)

( * ) Notice: Subject to any disclaimer, the term of this patent is extended or adjusted under 35 U.S.C. 154(b) by 282 days.

This patent is subject to a terminal disclaimer.

(21) Appl. No.: 12/679,429

(22) PCT Filed: Sep. 24, 2008

(86) PCT No.: PCT/US2008/077447
§ 371 (c)(1),
(2), (4) Date: Jul. 15, 2010

(87) PCT Pub. No.: WO2009/042639
PCT Pub. Date: Apr. 2, 2009

(65) Prior Publication Data
US 2010/0279268 A1 Nov. 4, 2010

Related U.S. Application Data

(63) Continuation-in-part of application No. 11/860,471, filed on Sep. 24, 2007, now Pat. No. 8,003,388.

(51) Int. Cl.
*C12N 5/07* (2010.01)

(52) U.S. Cl.
USPC .......................... 435/395; 435/325; 435/397

(58) Field of Classification Search
USPC ......................................... 435/395, 325, 397
See application file for complete search history.

(56) References Cited

U.S. PATENT DOCUMENTS

| | | |
|---|---|---|
| 4,878,908 A | 11/1989 | Martin et al. |
| 5,804,366 A | 9/1998 | Hu et al. |
| 6,503,273 B1 | 1/2003 | McAllister et al. |
| 6,592,623 B1 | 7/2003 | Bowin et al. |
| 6,642,019 B1 | 11/2003 | Anderson et al. |
| 6,893,812 B2 | 5/2005 | Woltering |
| 6,989,071 B2 | 1/2006 | Kocur et al. |
| 2002/0150879 A1 | 10/2002 | Woltering |
| 2002/0177121 A1 | 11/2002 | Woltering et al. |
| 2003/0138945 A1 | 7/2003 | McAllister et al. |
| 2003/0138950 A1 | 7/2003 | McAllister et al. |
| 2003/0171053 A1 | 9/2003 | Sanders |
| 2004/0044403 A1 | 3/2004 | Bischoff et al. |
| 2006/0216320 A1 | 9/2006 | Kitazono et al. |
| 2007/0110962 A1 | 5/2007 | Tien et al. |
| 2007/0116674 A1 | 5/2007 | Casteilla |
| 2007/0224677 A1 | 9/2007 | Neumann |

OTHER PUBLICATIONS

Pepper, M. S. et al., "Chondrocytes Inhibit Endothelial Sprout Formation in Vitro: Evidence for Involvement of a Transforming Growth Factor-Beta," J Cell Physiol 1991, 146:170-179.
Rosen, E. M. et al., "Quantitation of Cytokine-Stimulated Migration of Endothelium and Epithelium by a New Assay Using Microcarrier Beads," Exp Cell Res 1990, 186:22-31.
Sage, E. H., Vernon, R. B., "Regulation of Angiogenesis by Extracellular Matrix: the Growth and the Glue," J Hypertens Suppl 1994, 12:S145-152.
Vernon, R. B. et al., "Reorganization of Basement Membrane Matrices by Cellular Traction Promotes the Formation of Cellular Networks in Vitro," Lab Invest 1992, 66:536-547.
Vernon, R. B., Gooden, M. D., "New Technologies in Vitro for Analysis of Cell Movement on or Within Collagen Gels," Matrix Biol 2002, 21:661-669.
Vernon R. B. et al., "Organized Type I Collagen Influences Endothelial Patterns During 'Spontaneous Angiogenesis in Vitro': Planar Cultures as Models of Vascular Deveopment," In Virto Cell Dev Biol Anim 1995, 31: 120-131.
Vernon R. B., Sage, E.H., "A Novel, Quanititative Model for Study of Endothelial Cell Megration and Sprout Formation Within Three-Dimensional Collagen Matrices," Microvasc Res 1999, 57: 118-133.
Villaschi, S., Nicosia, R. F., "Angiogenic Role of Endogenous Basic Fibroblast Growth Factor Released by Rat Aorta After Injury," Am J Pathol 1993, 143: 181-190.
Neumann, Thomas, Grant Abstract, Grant No. 1 R21 HL081152-01 awarded by NIH national Heart, Lung and Blood Institute 2005.
Ratner, Buddy D., Grant Abstract, Grantt No. 5R24HL064387-04 awarded by NIH National Heart, Lung and Blood Institute 2003.
L'Heureux, N. et al., "A Completely Biological Tissue-Engineered Human Blood Vessel," The FASEB Journal. vol. 12 (1), pp. 47-56, Jan. 1998.
Migliore, A. et al., "Controlled In Vitro Growth of Cell Microtubes: Towards the Realisation of Artifcial Microvessels," Biomed Microdevices. vol. 10, pp. 81-88, Aug. 9, 2007.
Adryan, B., et al., Tracheal development and the von Hippel-Lindau tumor suppressor homolog in Drosophila. Oncogene. 2000. 19(24): p. 2803-11.

(Continued)

*Primary Examiner* — Ruth Davis
(74) *Attorney, Agent, or Firm* — George A. Leone; Citadel Patent Law

(57) ABSTRACT

A method for creating networks of perfusable microvessels in vitro. Cells including cell types capable of sprouting are seeded 1300 into a channel in a matrix at to activate competency 1304 of the cells for sprouting as microvessels based on the seeding density. The matrix channel is perfused with medium to allow parent vessels to form and for viability 1324. The parent vessels and matrix are incubated and perfused to provide for sprouting of microvessels from parent vessels into the surrounding matrix 1328. The sprouting parent vessels are grown until network forms 1332.

33 Claims, 26 Drawing Sheets

OTHER PUBLICATIONS

Ghabrial, A., et al., Branching morphogenesis of the Drosophila tracheal system. Annu Rev Cell Dev Biol, 2003. 19: p. 623-47.
Gerhardt, H., et al., VEGF guides angiogenic sprouting utilizing endothelial tip cell filopodia. J Cell Biol, 2003. 161(6): p. 1163-77.
Gerhardt, H., VEGF and endothelial guidance in angiogenic sprouting. Organogenesis, 2008. 4(4): p. 241-6.
Lubarsky, B. and M.A. Krasnow, Tube morphogenesis: making and shaping biological tubes. Cell, 2003. 112(1): p. 19-28.
Horowitz, A. and M. Simons, Branching morphogenesis. Circ Res, 2008. 103(8): p. 784-95.
Metzger, R.J. and M.A. Krasnow, Genetic control of branching morphogenesis. Science, 1999. 284(5420): p. 1635-9.
Hogan, B.L. and P.A. Kolodziej, Organogenesis: molecular mechanisms of tubulogenesis. Nat Rev Genet, 2002. 3(7): p. 513-23.
Wiseman, B.S. and Z. Werb, Stromal effects on mammary gland development and breast cancer. Science, 2002. 296 (5570): p. 1046-9.
Castellucci, M., et al., Villous sprouting: fundamental mechanisms of human placental development. Hum Reprod Update, 2000. 6(5): p. 485-94.
Nicosia, R.F., Ottinetti, A., Growth of Microvessels in Serum-Free Matrix Culture of Rat Aorta, Laboratory Investigation, vol. 63, No. 1, p. 115-122, 1990.
Maniotis, A. J. et al., Vascular Channel Formation by Human Melanoma Cells in Vivo and in Vitro: Vasculogenic Mimicry, American Journal of Pathology, vol. 155, No. 3, p. 739-752, Sep. 1999.
Neumann, T. et al., Tissue Engineering of Skeletal Muscle Using Polymer Fiber Arrays, Tissue Engineering, vol. 9, No. 5, p. 995-1003, 2003.
Lin, A. Y. et al., Distinguishing Fibrovascular Septa From Vasculogenic MimicryPatterns, Arch, Pathol. Lab. Med., vol. 129, p. 884-892, Jul. 2005.
Chrobak, "Formation of perfused, functional microvascular tubes in vitro," Microvascular Research 71 (May 2006) 185-196.
Akhtar, N. M., Dickerson E. B., Auerback R., "The Sponge/Matrigel Angiogenesis Assay." Angiogenesis, 2002, 5: 75-80.
Algire, G. H., Chalkley, H. W., Legallais, F. Y., "Vascula Reactions of Normal and Malignant Tissues in Vivo. I. Vascular Reactions of Mice to Wounds and to Normal and Neoplastic Transplants," J Natl Cancer Inst 1945, 6:73-85.
Andrade, S. P. et al., "Sponge-Induced Angiogenesis in Mice and the Pharmacological Reactivity of the Neovasculature Quantitated by a Fluorimetric Method," Microvasc Res 1997, 54:253-261.
Arthur, W. T. et al., "Growth Factors Reverse the Impaired Sprouting of Microvessels from Aged Mice," Microvasc Res 1998, 55:260-270.
Ausprunk, D. H., Knighton, D. R., Folkman J., "Differentiation of Vascular Endothelium in the Chick Chorioallantois: A Structural and Autoradiographic Study." Dev Biol 1974, 38:237-248.
Clark, E. R., Clark, E. L., "Microscopic Observations on the Growth of Blood Capillaries in the Living Mammal," Am J Anat 1939, 64:251-301.
Davis, G.E., Camarillo, C. W., "An Alpha 2 Beta 1 Integrin-Dependent Pinocytic Mechanism Involving Intracellular Vacuole Formation and Coalescence Regulates Capillary Lumen and Tube Formation in Three-Dimensional Collagen Matrix," Exp Cell Res 1996, 224:39-51.
Elsdale, T., Bard J., "Collagen substrata for studies on cell behavior," J Cell Biol 1972, 54:626-637.
Feder, J. et al., "The formation of capillary-like tubes by calf aortic endothelial cells grown in vitro," J Cell Physiol 1983, 116:1-6.
Fishman, J. A. et al., "Endothelial Regeneration in the Rat Carotid Artery and the Significance of Endothelial Denudation in the Pathogenesis of Myointimal Thickening," Lab Invest 1975, 32:339-351.
Folkman, J., Haudenschild, C., "Angiogenesis in Vitro," Nature 1980, 288:551-556.
Folkman, J. et al., "Long-Term Culture of Capillary Endothelial Cells," Proc Natl Acad Sci U S A 1979, 76:5217-5221.
Gimbrone, M. A. Jr., "Culture of Vascular Endothelium," In: Prog Hemost Thromb. 1976, p. 1-28.
Gimbrone, M. A., Jr. et al., "Human Vascular Endothelial Cells in Culture. Growth and DNA synthesis," J Cell Biol 1974a, 60:673-684.
Grimbrone, M. A., Jr. et al., "Tumor Growth and Neovascularization: An Experimental Model Using the Rabbit Cornea," J Natl Cancer Inst 1974b, 52:413-427.
Greenblatt, M., Shubi, P., "Tumor Angiogenesis: Transfilter Diffusion Studies in the Hamster by the Transparent Chamber Technique," J Natl Cancer Inst 1968, 41:111-124.
Hoying, J. B. et al., "Angiogenic Potential of Microvessel Fragments Established in Three-Dimensional Collagen Gels," In Vitro Cell Dev Biol Anim 1996, 32:409-419.
Jaffe, E. A. et al., "Culture of Human Endothelial Cells Derived From Umbilical Veins. Identification by Morphologic and Immunologic Criteria," J Clin Invest 1973, 52:2745-2756.
Jozaki, K. et al. "An in Vitro Model of Cell Migration: Evaluation of Vascular Endothelial Cell Migration," Anal Biochem 1990, 190:39-47.
Koike, T. et al., "Inhibited Angiogenesis in Aging: a Role for TIMP-2," J Gerontol A Biol Sci Med Sci 2003, 58: B798-805.
Kubota, Y. et al., "Role of Laminin and Basement Membrane in the Morphological Differentiation of Human Endothelial Cells into Capillary-Like structures," J Cell Biol 1988, 107:1589-1598.
Kuzuya, M., Kinsella, J. L., "Induction of Endothelial Cell Differentiation in Vitro by Fibroblast-Derived Soluble Factors," Exp Cell Res 1994, 215:310-318.
Maciag, T. et al., Organizational behavior of human umbilical vein endothelial cells. J Cell Biol 1982, 94:511-520.
Madri, J. A., "Endothelial Cell-Matrix Interactions in Hemostasis," Prog Hemost Thromb 1982, 6:1-24.
Madri, J. A., Pratt, B. M., "Endothelial Cell-Matrix Interactions: In Vitro Models of Angiogenesis," J Histochem Cytochem 1986, 34:85-91.
Madri, J. A. et al., "Phenotypic Modulation of Endothelial Cells by Transforming Growth Factor-Beta Depends Upon the Composition and Organization of the Extracellular Matrix," J Cell Biol 1988, 106:1375-1384.
Madri, J. A., Stenn, K. S., "Aortic Endothelial Cell Migration. I. Matrix Requirements and Composition," Am J Pathol 1982, 106:180-186.
Manoussaki, D. et al., "A Mechanical Model for the Formation of Vascular Networks in Vitro," Acta Biotheor 1996, 44:271-282.
Marx, M. et al., "Modulation of Platelet-Derived Growth Factor Receptor Expression in Microvascular Endothelial Cells During in Vitro Angiogenesis," J Clin Invest 1994, 93:131-139.
Merwin, J. R. et al., "Transforming Growth Factor Beta 1 Modulates Extracellular Matrix Organization and Cell-Cell Junctional Complex Formation During in Vitro Angiogenesis," J Cell Physiol 1990, 142:117-128.
Montesano, R., Orci, L., "Tumor-Promoting Phorbol Esters Induce Angiogenesis in Vitro," Cell 1985, 42:469-477.
Montesano, R. et al., "In Vitro Rapid Organization of Endothelial Cells into Capillary-Like Networks is Promoted by Collagen Matrices," J Cell Biol 1983, 97:1648-1652.
Montesano, R. et al., "Paracrine Induction of Angiogenesis in Vitro by Swiss 3T3 Fibroblasts," J Cell Sci 1993, 105 ( Pt 4):1013-1024.
Mori, M. et al., "Capillary Growth from Reversed Rat Aortic Segments Cultured in Collagen Gel," Acta Pathol Jpn 1988, 38:1503-1512.
Nehls, V., Drenckhahn, D., "A Novel, Microcarrier-Based in Vitro Assay for Rapid and Reliable Quantification of Three-Dimensional Cell Migration and Angiogenesis," Microvasc Res 1995, 50:311-322.
Nehls, V., Herrmann, R., "The Configuration of Fibrin Clots Determines Capillary Morphogenesis and Endothelial Cell Migration," Microvasc Res 1996, 51:347-364.
Neumann, T. et al., "Tissue Engineering of Perfused Microvessels," Microvasc Res 2003, 66:59-67.
Nicosia, R. F. et al., "Modulation of angiogenesis in vitro by laminin-entactin complex." Dev Biol 1994a, 164:197-206.
Nicosia, R. F. et al., "Large-Vessel Endothelium Switches to a Microvascular Phenotype During Angiogenesis in Collagen Gel Culture of Rat Aorta," Atherosclerosis 1992, 95:191-199.
Nicosia, R. F. et al., "Vascular Endothelial Growth Factor, Platelet-Derived Growth Factor, and Insulin-Like Growth Factor-1 Promote Rat Aortic Angiogenesis in Vitro," Am J Pathol 1994b,145:1023-1029.

Nicosia, R. F., Ottinetti, A., "Modulation of Microvascular Growth and Morphogenesis by Reconstituted Basement Membrane Gel in Three-Dimensional Cultures of Rat Aorta: a Comparative Study of Angiogenesis in Matrigel, Collagen, Fibrin, and Plasma Clot," In Vitro Cell Dev Biol 1990, 26:119-128.

Nicosia, R. F. et al., "Histotypic Angiogenesis in Vitro: Light Microscopic, Ultrastructural, and Radioautographic Studies," In Vitro 1982, 18:538-549.

Nicosia, R. F. et al., "Angiogenesis-Dependent Tumor Spread in Reinforced Fibrin Clot Culture," Cancer Res 1983, 43:2159-2166.

Nicosia, R. F., Tuszynski, G. P., "Matrix-Bound Thrombospondin Promotes Angiogenesis in Vitro," J Cell Biol 1994, 124:183-193.

Passaniti, A. et al., "A Simple, Quantitative Method for Assessing Angiogenesis and Antiangiogenic Agents Using Reconstituted Basement Membrane, Heparin, and Fibroblast Growth Factor," Lab Invest 1992, 67:519-528.

Chrobak, Kenneth M. et al., "Formation of perfused, functional microvascular tubes in vitro," Microvascular Research May 2006 LNKD-PUBMED: 16600313, vol. 71, No. 3, May 2006, pp. 185-196.

Frerich Bernard et al., "Microvascular engineering in perfusion culture: immunohistochemistry and CLSM findings.", Head 7 Face Medicine 2006 LNKD-PUBMED: 16914036, vol. 2, 2006, p. 26.

Frerich B et al., "Maturation of Capillary-like structures in a tube-like construct in persfusion and rotation culture.", International Journal of Oral and Maxillofacial Surgery May 2008 LNKD-PUBMED: 18367381, vol. 37, No. 5, May 2008, pp. 459-466.

Takei, Takayuki et al., "Fabrication of Artificial Endothelialized Tubes with Predetermined Three-Dimensional Configuration from Flexible Cell-Enclosing Alginate Fibers" Biotechnol. Prog. 2007, 23, 182-186.

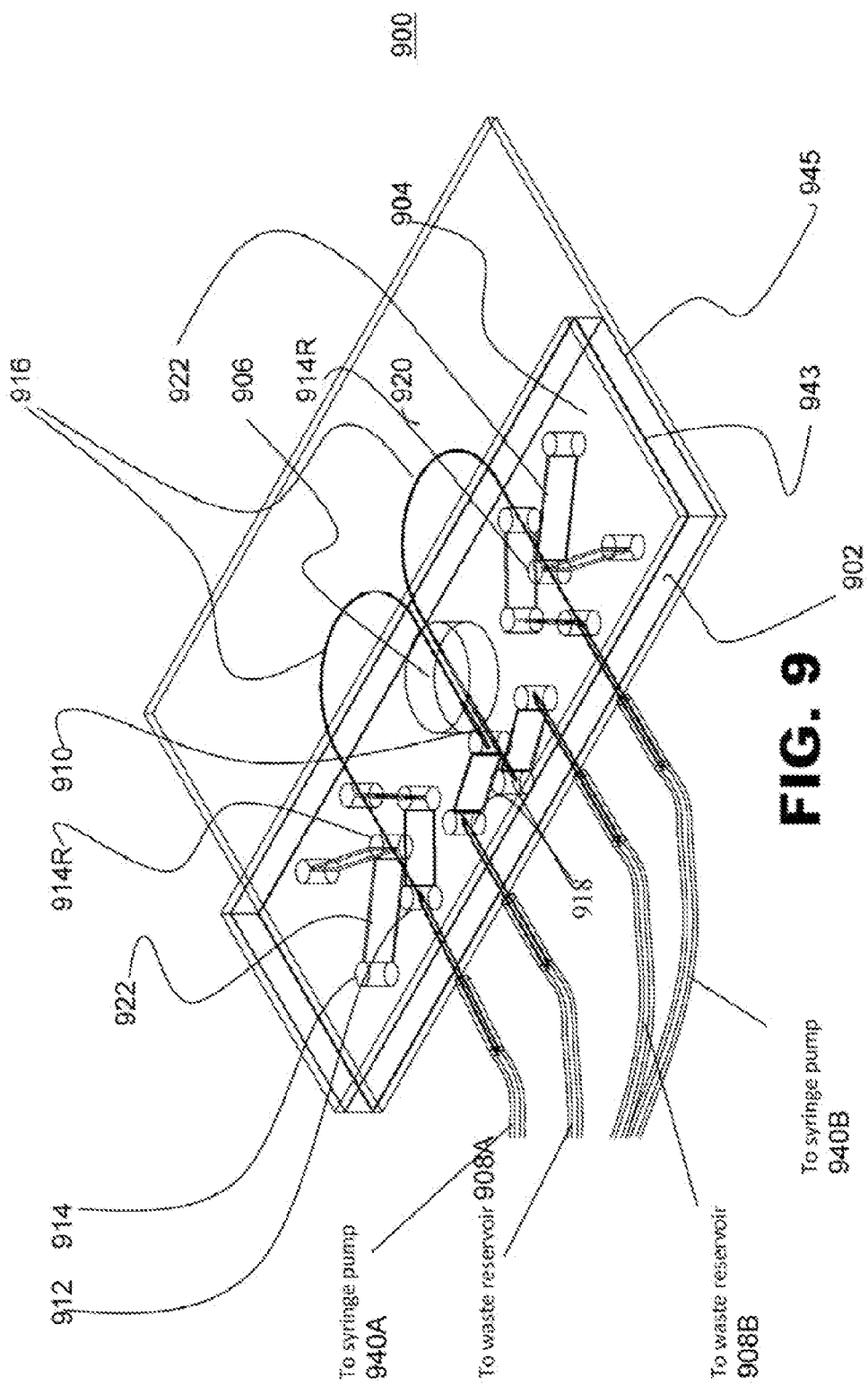

1050
1052
1054

1102
1106
1104

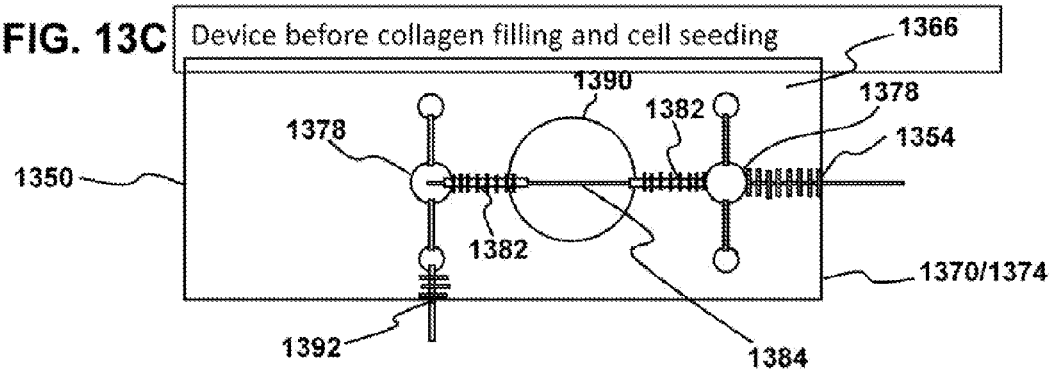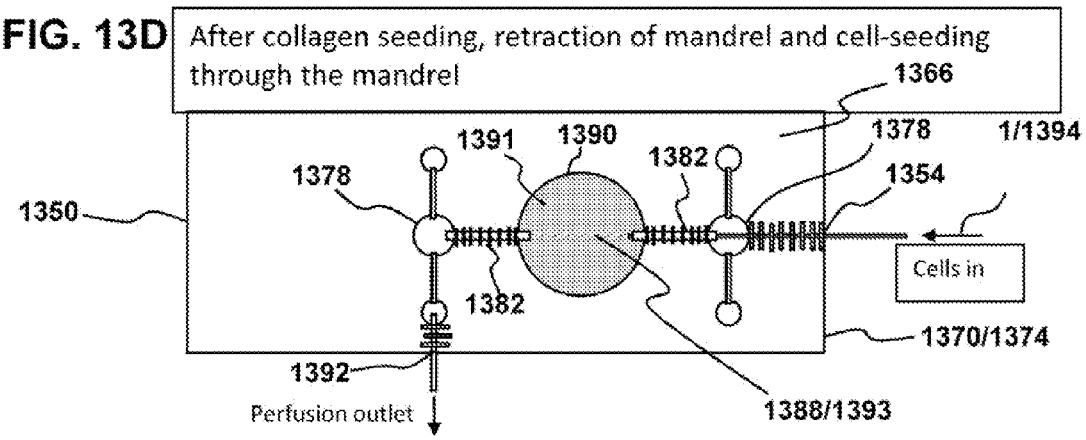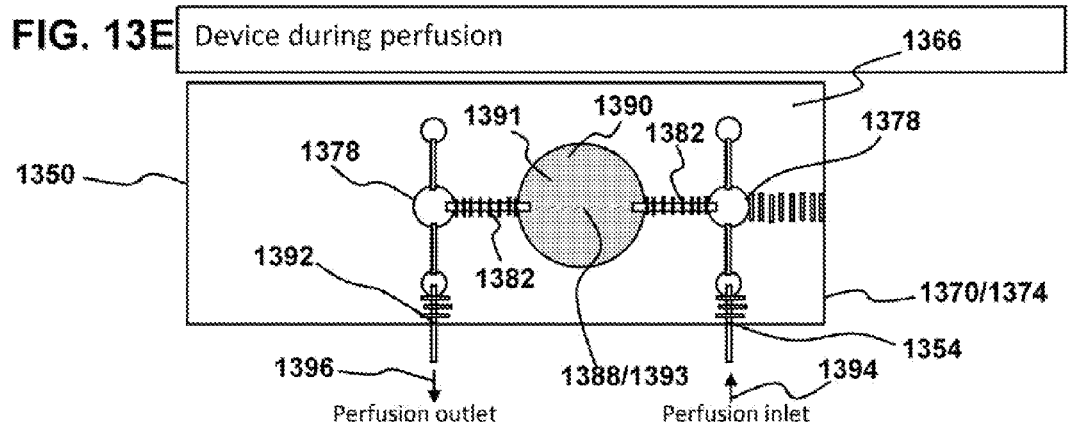

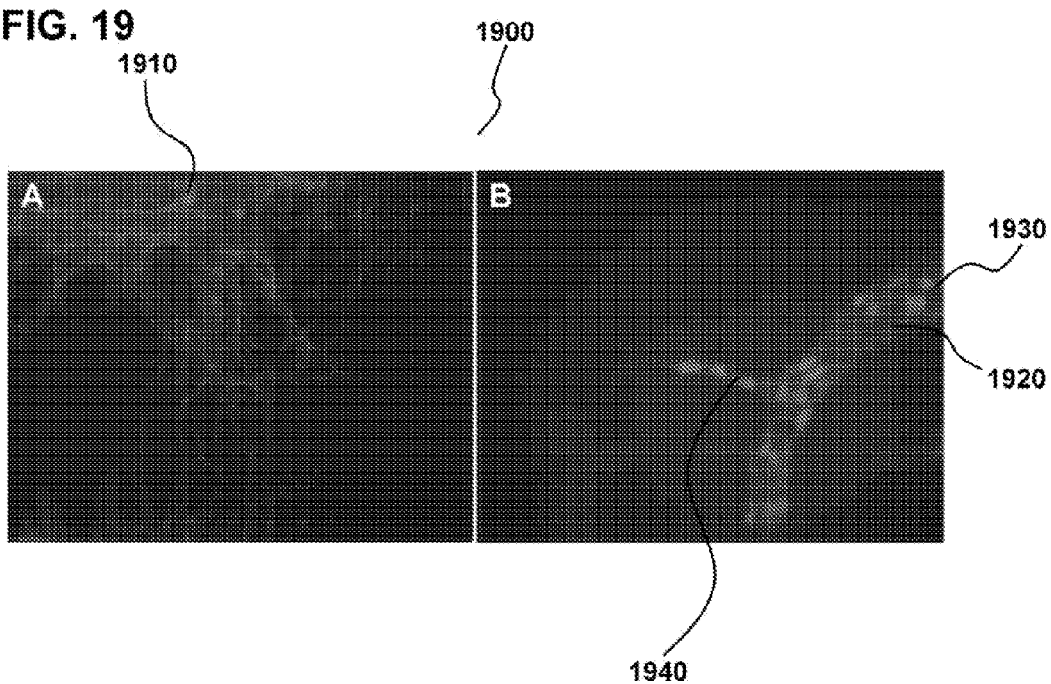

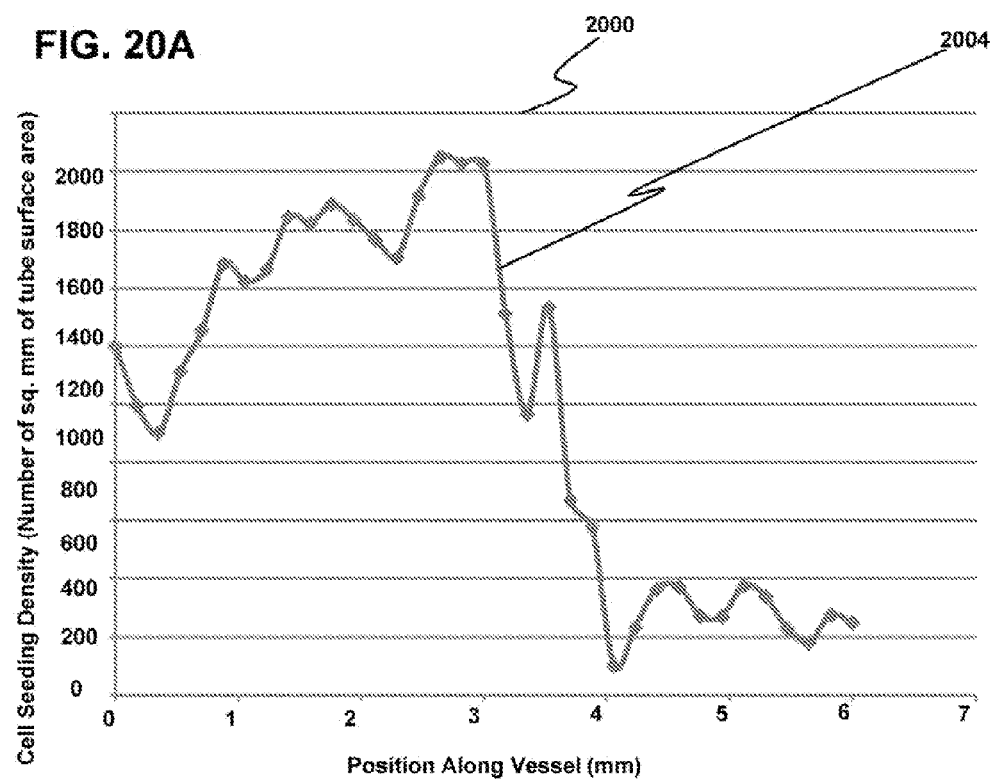

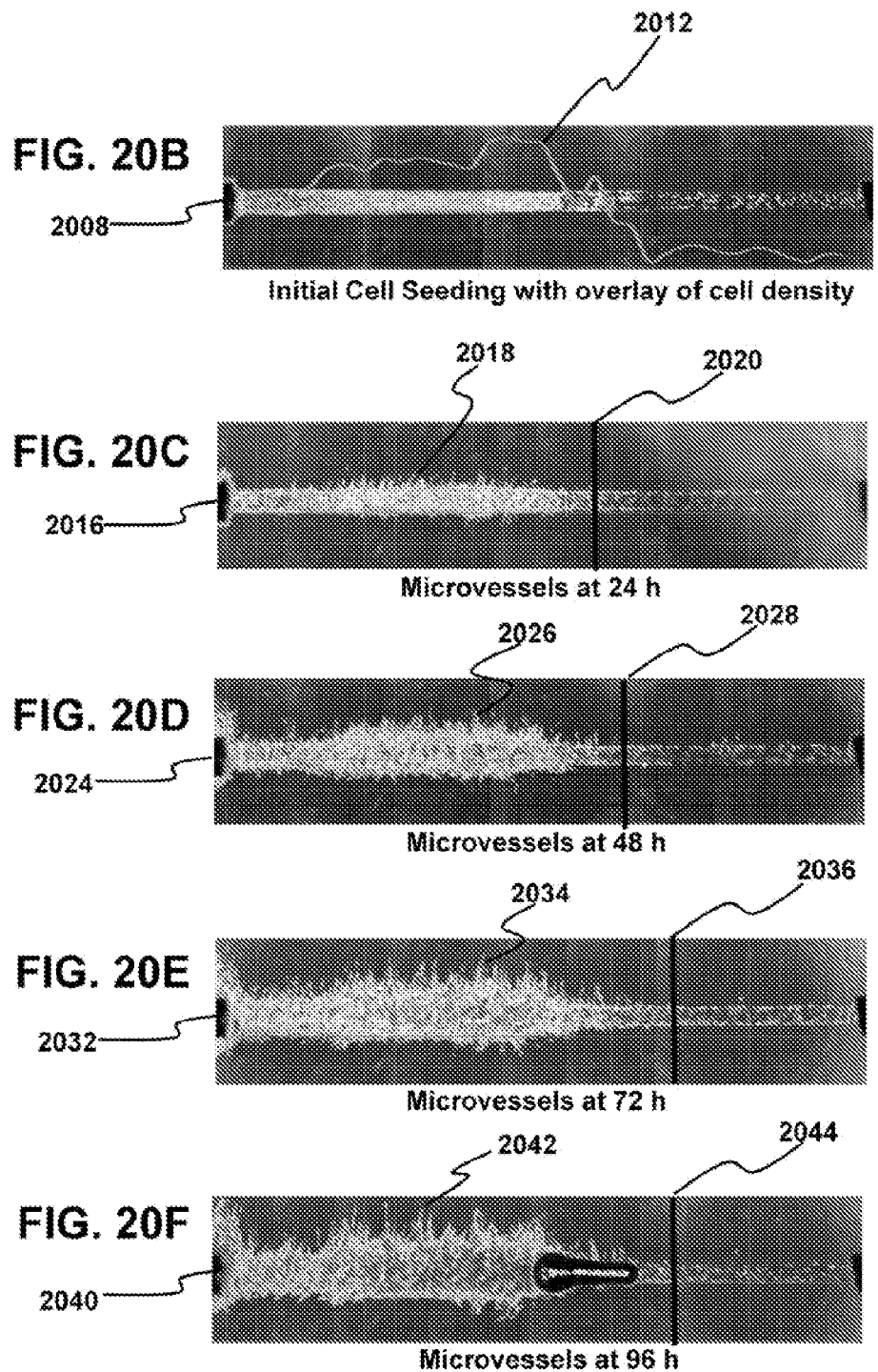

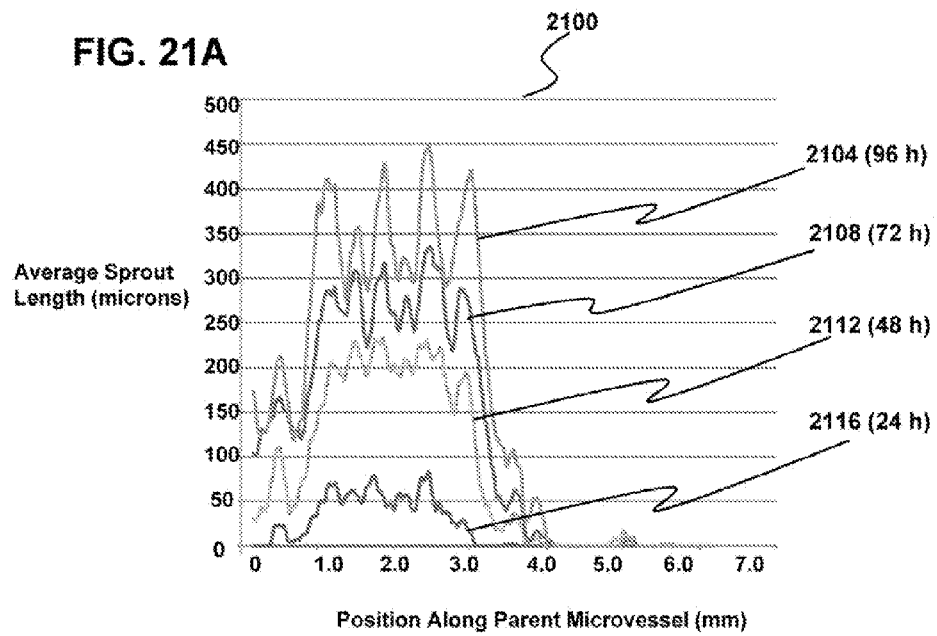
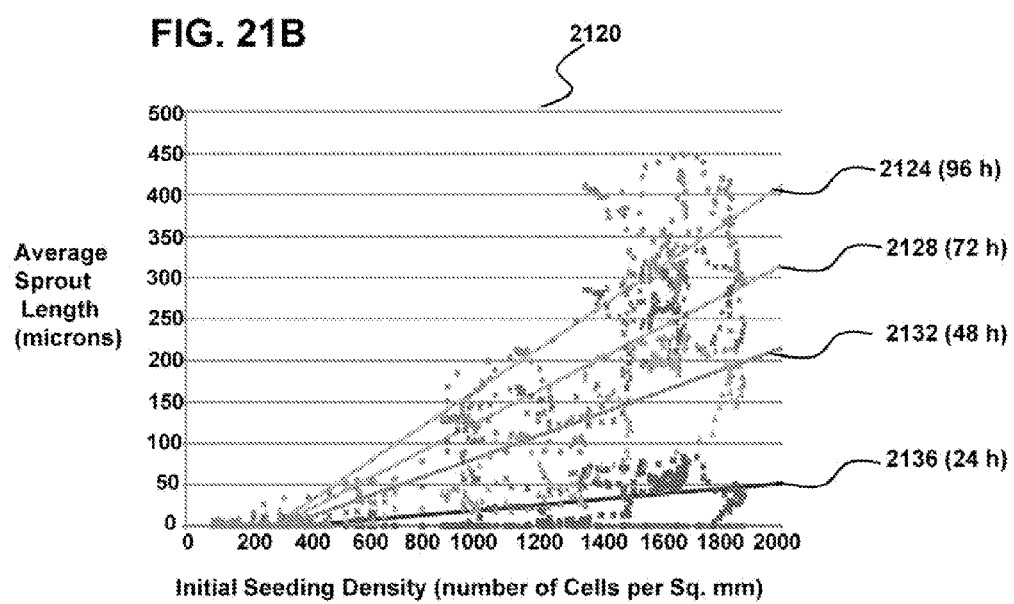

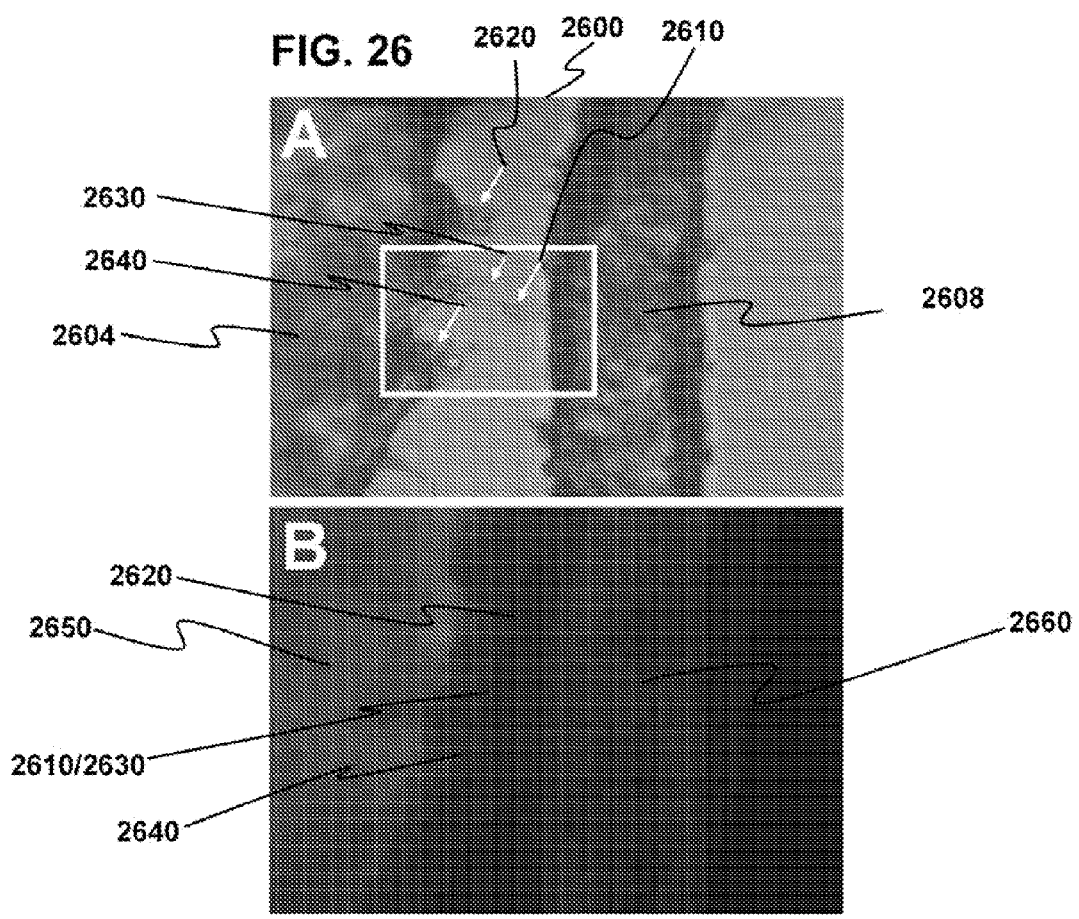

METHOD FOR CREATING PERFUSABLE MICROVESSEL SYSTEMS

RELATED APPLICATION

This application claims priority from and is a continuation-in-part of co-pending U.S. application Ser. No. 11/860,471 of Neumann, filed Sep. 24, 2007, entitled "Method for Creating Perfusable Microvessel Systems," which is a continuation in part of U.S. application Ser. No. 11/388,920 of Neumann, filed Mar. 24, 2006, U.S. application Ser. No. 11/388,920 and U.S. application Ser. No. 11/860,471 of Neumann are hereby incorporated by reference.

FIELD OF THE INVENTION

The present invention relates to methods for the study of physiological and pathological vascular growth, and vascular growth in response to angiogenic or angiostatic factors.

TECHNICAL BACKGROUND

During normal processes of vascular growth (e.g., the menstrual cycle, placentation, changes in adiposity, wound repair, inflammation), the creation of new blood vessels is regulated and eventually ceases. Significantly, the deregulation of vascular growth is a critical element of pathology. For example, tumor growth, diabetic retinopathies, arthritis, and psoriasis involve excessive proliferation of blood vessels that contributes directly to the pathological state. In contrast, impairment of vascular growth, characteristic of aged individuals, compromises the healing of wounds and the revascularization of tissues rendered ischemic by trauma or disease. Therefore, an understanding of the mechanisms that direct the assembly new blood vessels, and the processes that start and stop vascular growth, are central to the development of strategies to control vascularization in disease.

During the growth of new blood vessels (angiogenesis), sprouts arise from endothelial cells that line the lumens of capillaries and postcapillary venules—the smallest branches of the vascular system. Angiogenesis is a complex, multi-step process. Although published studies of angiogenesis number in the many thousands, the cellular mechanisms that mediate and regulate angiogenic growth and morphogenesis are poorly understood.

The details of angiogenic sprouting are difficult to observe in "real-time" in viva because of the opacity of most tissues. Tissue sections are difficult to reconstruct in 3D and do not communicate the dynamic nature of vascular growth. Moreover, the region near the tips of angiogenic sprouts—a critical area of control of vascular invasion and morphogenesis—is rarely found in tissue sections. In order to overcome the limitations of conventional histology, a variety of "models" of angiogenesis in vivo and in vitro have been developed.

Models of angiogenesis in vivo: To circumvent the opacity of living tissues, investigators have observed angiogenesis through "Windows" in living animals that include the naturally transparent tails of amphibian larvae (Clark and Clark 1939), or specialized viewing chambers either implanted into rabbit ears (Clark and Clark 1939), mouse skin (Algire, Chalkley et al. 1945) and hamster cheek pouches (Greenblatt and Shubi 1968) or developed from rabbit corneal pockets (Gimbrone, Cotran at al. 1974) or chick chorioallantoic membranes (Ausprunk, Knighton et al. 1974). From these early, largely descriptive studies came validation of the central paradigm of tumor-induced vascular chemotaxis and the corresponding discovery of diffusible, tumor-derived molecules that promote vascular growth. Newer assays of angiogenesis in vivo measure vascular ingrowth into polymeric sponges or plugs of gelled basement membrane proteins implanted subcutaneously into rodents (Passaniti, Taylor at al. 1992; Andrade, Machado at al. 1997; Akhtar, Dickerson at al. 2002; Koike, Vernon et al. 2003). For all of their elegance, approaches in vivo are made difficult by (1) intra-species variation in angiogenic response from animal to animal; (2) the lack of translation of results from one species to another; (3) high costs of animal purchase and maintenance; (4) public disapproval of the use of animals for research purposes; and (5) complexities encountered in animal surgeries and in the visualization and evaluation of results.

Two-dimensional (2D) models of angiogenesis in vitro: In an effort to understand the molecular mechanics of angiogenesis, endothelial cells isolated from large vessels were cultured in flat dishes until they formed confluent, pavement-like monolayers that simulated the endothelial linings of blood vessels (Jaffe, Nachman at al. 1973; Gimbrone 1976). Although useful as models of proliferative responses to endothelial injury in large blood vessels (Gimbrone, Cotran at al. 1974; Fishman, Ryan at al, 1975; Madri and Stenn 1982; Madri and Pratt 1986; Jozaki, Marucha et al. 1990; Rosen, Meromsky et al. 1990), monolayer cultures of endothelial cells on rigid substrata do not typically organize into capillary-like tubes in simulation of angiogenesis. In 1980, however, following successful long-term culture of capillary endothelial cells (Folkman. Haudenschild at al. 1979), it was reported that 20-40 day cultures of bovine or human capillary endothelial cells developed a 2D cellular network on top of the confluent cellular monolayer, a process termed "angiogenesis in vitro" (Folkman and Haudenschild 1980). The endothelial cells of the network appeared as "lubes" with "lumens" filled with a fibrillar/amorphous material that was interpreted to be an endogenously-synthesized network of "mandrels" on which the cells organized. Later studies reported similar 2D network formation by endothelial cells from large vessels (Maciag, Kadish at al, 1982; Madri 1982; Feder, Marasa at al. 1983) and by endothelial cells seeded on top of malleable, hydrated gels of basement membrane proteins (e.g. Matrigel® gel)(Kubota, Kleinman at al, 1988).

Although 2D models of vascular development remain in use today (the Matrigel®-based assay (Kubota, Kleinman at al. 1988) is available commercially), such models lack the following 5 defining characteristics of true angiogenesis:

1. Invasion—Endothelial cells in 2D models form networks on top of extracellular matrix and show little propensity to burrow into the extracellular matrix (Vernon, Angello et al. 1992; Vernon, Lara et al. 1995).
2. Directionality—In 2D models, the networks of endothelial cells form in vitro more or less simultaneously throughout a field of pre-positioned cells, whereas angiogenesis in vivo involves the vectorial invasion of extracellular matrix by filamentous sprouts that arborize by multiple levels of branching.
3. Correct polarity—Although the 2D models make unicellular tubes that markedly resemble capillaries (Maciag, Kadish et al, 1982; Feder, Marasa et al, 1983; Sage and Vernon 1994), their polarity is "inside-out", that is, they deposit basement membrane material on their luminal surfaces and have their thrombogenic surfaces facing outward to the surrounding culture media (Maciag, Kadish et al. 1982; Feder, Marasa et al 1983)—opposite to the situation in vivo,
4. Lumen formation—Evidence that 2D models generate endothelial cell (EC) tubes with patent lumens is weak. Typically, the endothelial cell tubes have "luminal" spaces that are filled with extracellular matrix (either exogenous or synthesized by the cells)(Maciag, Kadish et al. 1982; Madri 1982; Feder, Marasa et al. 1983; Sage and Vernon 1994; Vernon, Lara et al. 1995). Where present, patent lumens usually appear as slit-like or narrow cylindrical spaces bounded by thick walls of endothelial cell cytoplasm—quite different from the inflated, thin-walled endothelial cell tubes that typify capillaries in viva 5. Cell specificity—The cellular networks in 2D models are generated by mechanical processes that may be accomplished by non-EC cell types (Vernon, Angello et al, 1992; Vernon, Lara et al. 1995). Indeed, mathematical modeling has shown that any adherent cell type capable of applying tensile forces to malleable, 2D extracellular matrix (either synthesized endogenously or supplied (e.g., Matrigel® gel)) can generate networks under optimal conditions (Manoussaki; Lubkin et al. 1996).

Three-dimensional (3D) models of angiogenesis in vitro: The recognition that angiogenesis in vivo occurs within a 3D extracellular matrix has led to a variety of models in which sprouting is induced within 3D gels of extracellular matrix in vitro. In an early 3D model, endothelial cells dispersed within collagen gels (Montesano, Orci et al, 1983) formed networks of cords and tubes (Elsdale and Bard 1972). Although the endothelial cell tubes exhibited correct polarity, the characteristics of invasion and directionality were lacking (the endothelial cells were pre-embedded and evenly dispersed in the extracellular matrix). Nonetheless, this approach has proven useful in studies of lumen formation (Davis and Camarillo 1996) and of responses of endothelial cells to growth factors (Madri, Pratt et al. 1988; Merwin, Anderson et al. 1990; Kuzuya and Kinsella 1994; Marx, Perlmutter et al, 1994; Davis and Camarillo 1996).

In an alternative approach, 1 mm sections (rings) of rat aorta embedded in a 3D plasma clot generated branching, anastomosing tubes (Nicosia, Tchao et al, 1982). Sprouts from the aortic rings exhibited angiogenesis-like invasion and directionality in addition to polarity. Explant models utilizing aortic rings from rats or microvascular segments from mice have been used to study the influence of tumors, growth factors, various extracellular matrix supports, and conditions of aging on angiogenesis (Nicosia, Tchao et al. 1983; Mori, Sadahira et al. 1988; Nicosia and Ottinetti 1990; Nicosia, Bonanno et al. 1992; Villaschi and Nicosia 1993; Nicosia, Bonanno et al. 1994; Nicosia, Nicosia et al. 1994; Nicosia and Tuszynski 1994; Hoying, Boswell et al. 1996; Arthur, Vernon et al. 1998).

A variety of models exist that induce purified endothelial cells (as monolayers or aggregates) to sprout invasively into underlying or surrounding 3D extracellular matrix gels (Montesano and Orci 1985; Pepper, Montesano et al. 1991; Montesano, Pepper et al, 1993; Nehls and Drenckhahn 1995; Nehls and Herrmann 1996; Vernon and Sage 1999; Vernon and Gooden 2002). Each of these models has specific limitations that include difficulty in visualizing sprout formation, limited sprouting, a requirement for sectioning, or lack of effectiveness with certain types of endothelial cells.

Wolverine and Gulec have disclosed a 3D angiogenesis system (US 2002/0150879 A1) that involves embedding a fragment of tumor tissue into a matrix. The outgrowth of microvessels can be characterized to assay the angiogenic potential of the tissue. However, this approach does not provide luminal perfusion of the microvessels.

Neumann (the inventor here) et al. 2003, has disclosed the possibility of creating perfused microvessels in vitro that can be included in an artificial tissue. Neumann et al. 2003 teaches using 127 micrometer nylon fishing line as mandrels held by shrink tubing for making microvessels. The vessels were made from rat aortic smooth muscle cells embedded in agar. These microvessels were of an exploratory nature and not suitable for creating a human vessel graft.

Two-dimensional models of vascular growth in vitro do not establish the defining characteristics of angiogenesis listed previously, whereas existing 3D models reproduce some or most of the characteristics. Importantly, none of the 3D models currently available reconstruct a parent blood vessel that contains a pressurized, flowing, circulatory fluid. Consequently, none of the existing in vitro 3D models permit study of the contribution of luminal pressure and flow to vascular growth and morphogenesis,

SUMMARY OF THE DISCLOSURE

A method for creating networks of perfusable microvessels in vitro, is disclosed. Cells in are seeded into a channel within a matrix. The cells capable of sprouting are activated for competency to sprout as microvessels from parent vessels. The competency for sprouting in the cells is triggered from the density of the seeding. The channel is perfused with medium forming parent vessels. The parent vessels are incubated and perfused to maintain viability and to provide for sprouting of the microvessels into the surrounding matrix. The sprouting parent vessels are grown until have formed networks.

The present disclosure provides methods and systems that overcome the limitations of existing models of angiogenesis by combining proven methods for generating invasive, tubular, microvascular sprouts in 3D extracellular matrix (ECM) with novel methodologies for the fabrication of a tissue-engineered parent vessel that will be the source of luminal flow. Via the perfusate, angiogenesis-modulatory compounds can be administered to the luminal surface of endothelial cells where specific target receptors are known to reside.

The presence of a luminal flow of nutrient medium may substantially increase the survival time and stability of capillary tubes in vitro. Luminal perfusion has been shown to have a positive impact on vessel growth and maturation, (French, Zuckmantel et al. 2008). This implies that the vessels would be more stable with luminal perfusion. Further, inclusion of smooth muscle cells or pericytes, endothelial progenitor cells, and even stem cells into formation of parent vessels would be believed to aid function as part of the vessel maturation process.

The disclosed angiogenesis system can be used to evaluate a variety of experimental parameters that include hypoxia/hyperoxia, test of specific soluble or insoluble bioactive compounds, use of genetically modified cells, and gene delivery via viral transfection/transduction. The homophilic or heterotypic cell-cell interactions, cell-matrix interactions, cell-growth factor interactions, and mechanical-flow, can be examined as stimuli that induce cellular signaling that ultimately activate cells for integrated phenotypic behavior such as observed in the sprouting of microvessels from parent vessels.

Additionally, contribution of the physical forces from seeding at high-density can be evaluated for the sprouting competency phenotype. Without being bound to a particular theory, for example seeding of endothelial cells at high-density results in physical compression where the endothelial cells are balled up during the process. Since endothelial cells are typically spread out laterally in vessel formation this is not initially possible during seeding where cells are tightly packed together. Thus growth into the matrix may be favored triggering the sprouting phenotype. Also, with a higher number of cells per luminal surface area, sprouts can be formed much more quickly by simple migration and coalescence of cells rather than by cell division. The contributions of genes and gene products that regulate such cellular phenotypes in vessel formation can be elucidated. The system allows the study of angiogenesis relative to wound repair, aging, cancer, psoriasis, diabetic retinopathy, inflammatory diseases, stroke, and atherosclerosis, Importantly, a model following the teachings of the disclosure may be adapted to provide fully functional vascular systems capable of being incorporated into bioengineered artificial tissues.

The present disclosure also provides new and novel approaches, including a manifold design for making microvessels, making microvessels from endothelial cells and making larger vessels (e.g. having the size of coronary arteries). These and other important new teachings, including, for example, a method for creation of microvascular networks are evident from the specification and claims hereinbelow.

BRIEF DESCRIPTION OF THE DRAWINGS

FIG. 9 schematically shows an alternate embodiment of a CPD.

FIG. 13C schematically shows a CPD before filling the matrix chamber with collagen and before cell seeding.

FIG. 13D schematically shows a CPD after collagen seeding, retraction of mandrel, and cell-seeding through the mandrel.

FIG. 13E schematically shows a CPD during perfusion.

FIG. 19 shows microvessels stained with labeled wheat germ agglutinin to show the vessel structure and with the fluorescent dye DAPI to show nuclei.

FIG. 20A schematically shows the initial cells density of seeding plotted against the position along the aren't microvessel.

FIG. 20B, shows an image of a sprouting parent microvessel at the initial cell seeding density with an overlay of a plot of the cell density.

FIG. 20C shows an image of a sprouting parent microvessel after 24 h post seeding.

FIG. 20D, shows an image of a sprouting parent microvessel after 4 h post seeding.

FIG. 20E, shows an image of a sprouting parent microvessel after 72 h post seeding.

FIG. 20F, shows an image of a sprouting parent microvessel after 96 h post seeding.

FIG. 21A schematically shows a plot of the average sprout length versus (microns) the position along the parent microvessel (mm).

FIG. 21B schematically shows a plot of the best fit lines for average sprout length versus (microns) the initial seeding density (number of cells per Sq. mm).

FIG. 26A is a bright field image of two collagen channels from a CPD 2600, with one seeded with HUVECs that has formed a sprouting parent vessel and the second seeded with breast cancer cells 2608 of BT474 cell line.

FIG. 26B shows a corresponding fluorescence microscopy image of the same seeded collagen channels from the CPD in FIG. 26A.

DETAILED DESCRIPTION OF THE PREFERRED EMBODIMENTS

The examples presented herein are for the purpose of furthering an understanding of the invention The examples are illustrative and the invention is not limited to the example embodiments. The method of the present invention is useful for the study of physiological and pathological vascular growth, and vascular growth in response to angiogenic or angiostatic factors. Other useful applications are to methods that evaluate the angiogenic potential of cancer tissues and the response to antiangiogenic drugs. Further applications and methods are for basic research on physiology or pathology of vessel sprouting. Additionally, the method of the invention may be used to construct various wound-healing devices and for vascularization of tissue-engineered constructs.

In one example a method and device for the creation of perfusable three-dimensional microvessel networks is disclosed. As used herein "EC" refers to endothelial cells, "SMC" refers to smooth muscle cells and "CAS" refers to coronary-artery substitutes.

Generally, the devices for the culture and perfusion of microvessel networks consist of a chamber holding one or more mandrels in the center (as best shown in FIG. 1). The chambers can be fabricated from any biocompatible material and by a number of techniques; for example, by sandwiching laser-cut frames; by punching holes and channels into sheets of silicone, or by molding techniques. The mandrels are assembled within the chamber in such way that they are retractable. This can be achieved by fitting the ends of the mandrels into tubing, as for example, by heat shrinking, (as demonstrated in FIG. 2). The diameter of the mandrels depends on the desired vessel caliber. The setup can be modified to accommodate single vessels, two vessels, or up entire arrays of vessels in 2D or 3D. Mandrels can be of various materials, such as polymer fibers, glass fibers, wires or the like.

Microvessels are created by seeding cells onto the mandrels, stimulating the cells to multiply around the mandrels, and extracting the mandrels when cells have formed vessel walls. The vessels are then embedded in a matrix. Depending on the culture conditions, the composition of the matrix, and the presence of angiogenic stimuli (e.g, growth factors), the parent vessels will sprout into the surrounding matrix. The sprouts will anastomoze with each other and, thus leading to the formation of microvessel networks. After removal of the mandrels, the devices are connected to a perfusion system, and vessels are subjected to luminal fluid flow.

Figure 1A:
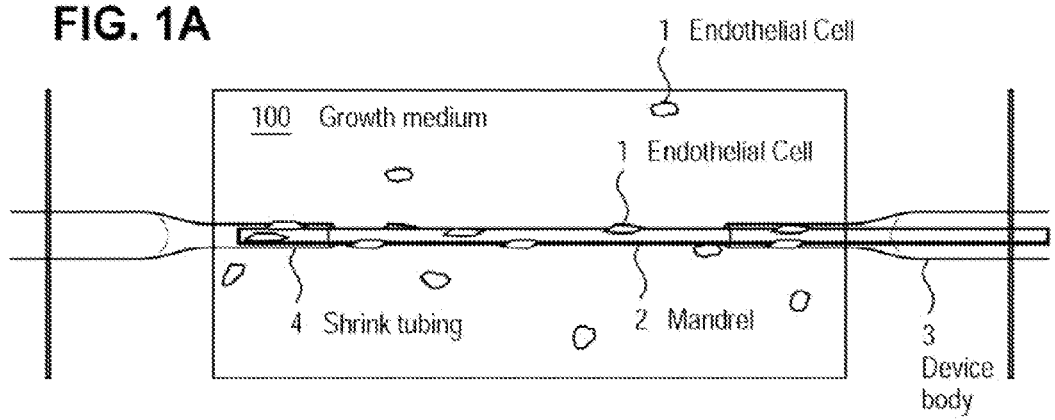
FIG. 1A, FIG. 1B and FIG. 1C schematically show an example of parent-vessel creation.
Figure 1B:
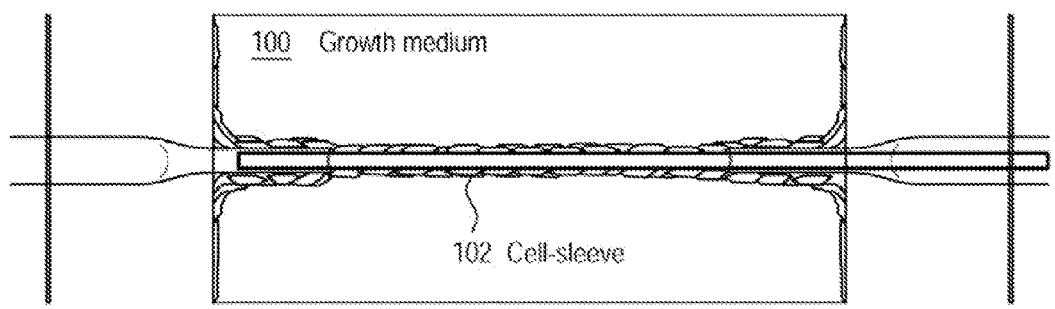
Figure 1C:
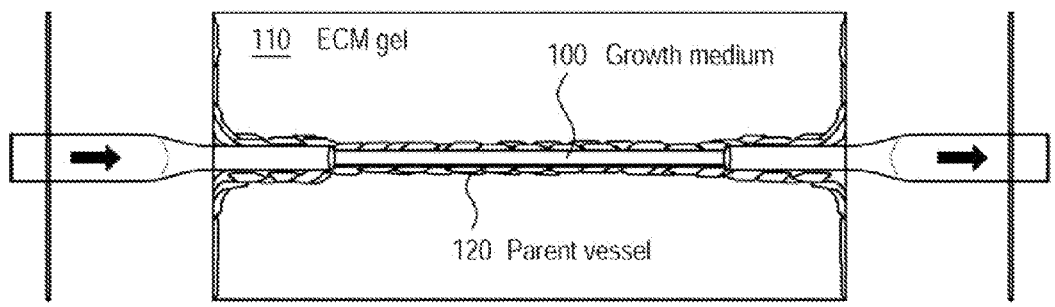

Referring now to FIG. 1A, FIG. 1B and FIG. 1C, there shown is an example schematic of parent-vessel creation. FIG. 1A shows endothelial cells 1 in a culture growth medium 100, seeded onto mandrel 2 held by shrink tubing 4 in a device body 3. FIG. 1B shows that the cells 1 have multiplied and formed a circular layer in the form of cell-sleeve 102. FIG. 1C shows the cell-sleeve after extraction of the mandrel 2 in an extracellular matrix (ECM) gel 110 being perfused with culture growth medium 100.

The method disclosed herein comprises the engineering of perfusable bioartificial vessel structures for tissue-engineering applications and research models. The general principle of the disclosed method involves the culture of cells in layers around removable mandrels that are tightly fit into thin-wall tubing or other fittings. Once the cell layers have reached a desired wall thickness, the mandrels are removed, and the hereby-created bioartificial vessels (BAVs) may be perfused with culture medium, blood, blood substitutes, or other fluids by aid of a perfusion system. The disclosed method allows for the production of mass manufactured or custom-created blood vessels, perfused in vitro angiogenesis models, wound healing devices, tissue components, whole tissues and organs, as well as research models.

Manufacture of Culture/Perfusion Devices

Referring now to FIG. 2A, FIG. 2B, FIG. 2C and FIG. 2D, there shown is an example schematic of a known heat-shrink process. As shown specifically in FIG. 2A each culture/perfusion device (CPD) may comprise one or more mandrels 2 held by a supporting frame 12. The mandrels 2 of the diameter of the desired vessel caliber are fit with their ends tightly into medical-grade shrink tubing segments 4. The mandrels 2 may comprise biocompatible fibers (e.g. polymer, glass, wires or equivalents) having diameters from several micrometers up to several millimeters depending on the vessel size being emulated. In one example, microcapillary tubing comprising optical fibers was employed as mandrels.

Figure 2A:
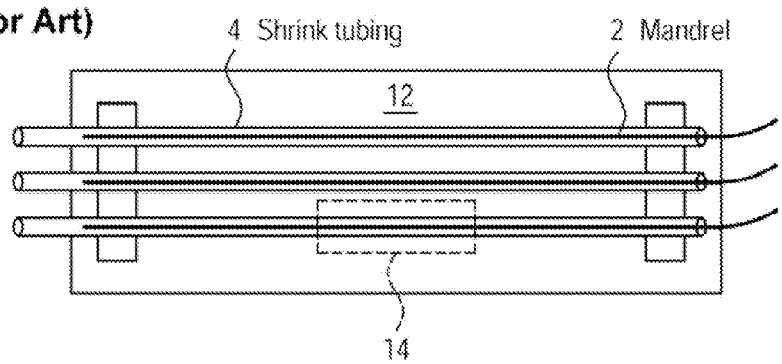
FIG. 2A, FIG. 2B, FIG. 2C and FIG. 2D schematically show an example of a known heat-shrink process.
Figure 2B:
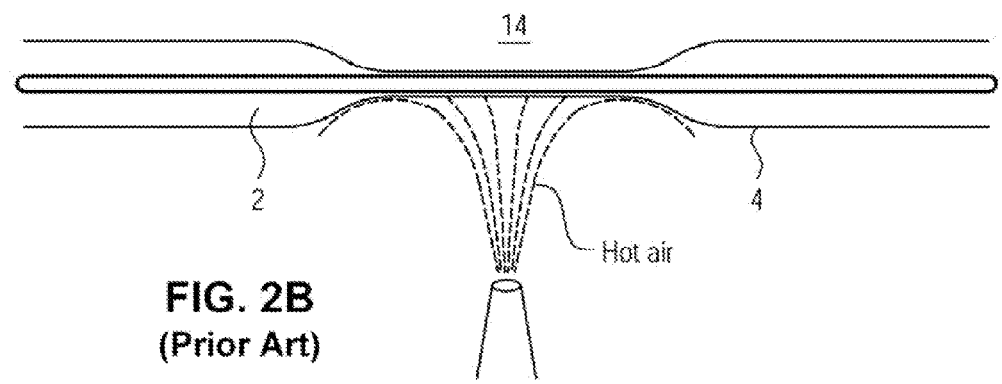
Figure 2C:
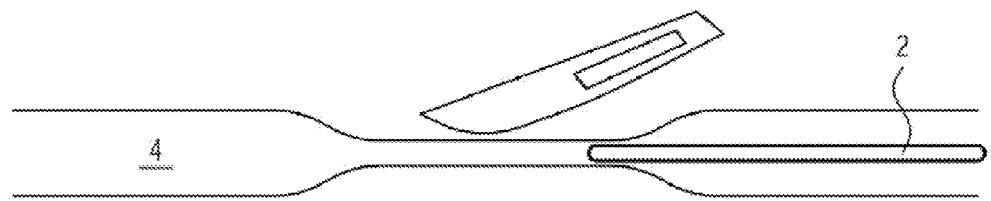
Figure 2D:
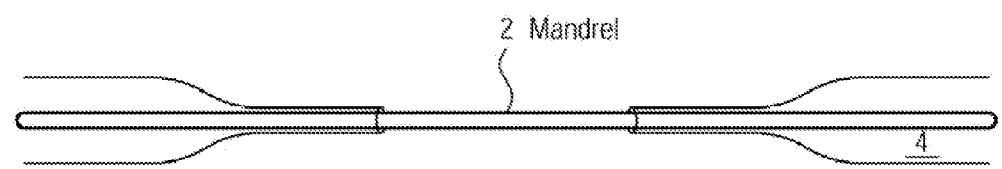

As shown in the more detailed drawing of FIG. 2B, a central portion 14 of each shrink tubing segment 4 is heat-shrunk around one of the mandrels 2. Subsequently; as specifically shown in FIG. 2G, the mandrel 2 is retracted, and the tubing cut. FIG. 2D shows the situation after re-positioning the mandrel such that both ends of the mandrel are enclosed by the now cut-and-separated shrink tubing segment 4. The frames 12 may be fabricated using various materials and techniques. The setup may be modified to accommodate either single bioartificial vessels or arrays of bioartificial vessels. Similarly, by layering several planes of mandrel arrays, a thick; perfusable tissue may be generated with vascular networks.

Machining of Perfusion Chambers

Figure 3A:
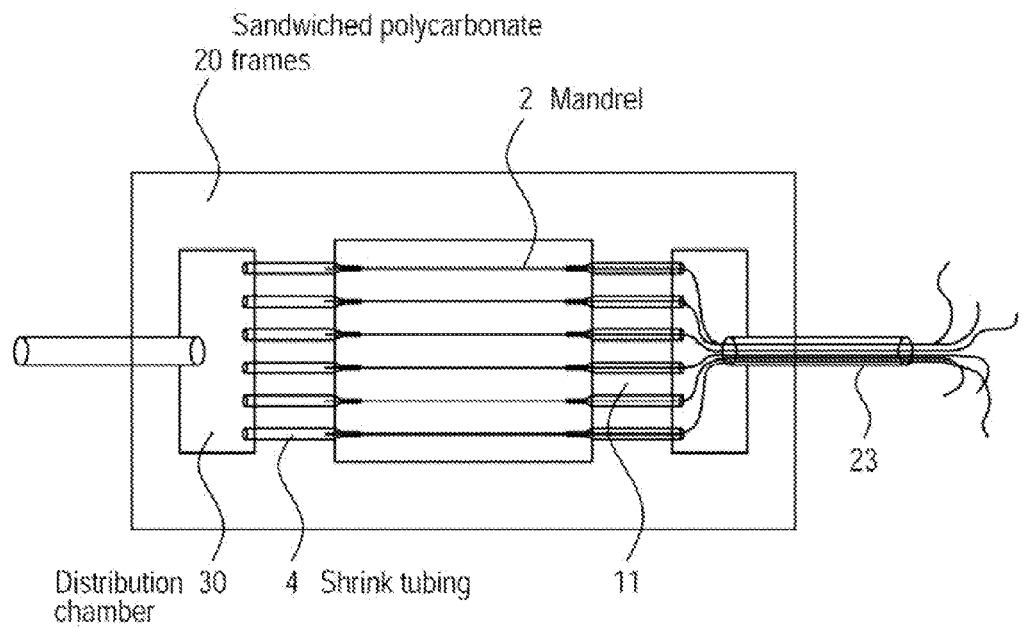
FIG. 3A schematically shows a known design for mounting culture/perfusion devices, FIG. 3B schematically shows a design used in a manufacturing method for mounting culture/perfusion devices.

Referring now to FIG. 3A, a known setup for the perfusion of several mandrel/shrink-tubing assemblies 11 is shown. A frame 20 may advantageously be milled from polycarbonate or equivalent materials. Distribution chambers 30 may be included into the design, which allows for simultaneous perfusion of many bioartificial vessels. Ends of a set of threads comprising the mandrels 2 are gathered in a silicon tube 23.

Laser Cutting of Mylar Frames

Figure 3B:
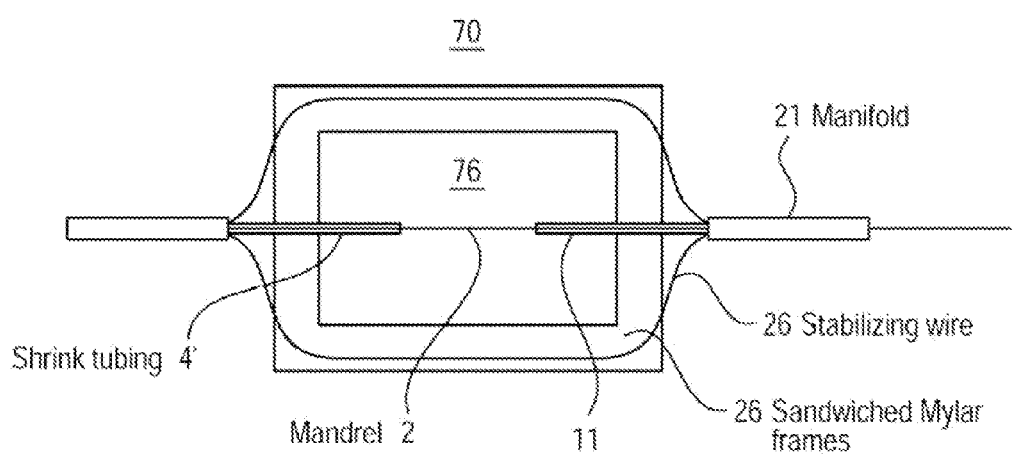

Referring now to FIG. 3B, a novel design used in a manufacturing method for mounting culture/perfusion devices is schematically shown. A single vessel design, CPD 70, may advantageously be created by sandwiching a mandrel 2 held by heat-shrink tubing 4 between two laser-cut Mylar® frames 22. A cylindrical epoxy manifold 21, constructed as detailed below, may advantageously be used for holding the mandrel/shrink-tubing assembly 11.

Mandrel/shrink-tubing assemblies may be sandwiched between two frames of a polyester film or the like, such as Mylar®, with adhesive sides pressed together such that each mandrel is suspended in the frame window 76 by two shrink-tubing segments 4' at each end. The two shrink-tubing segments 4' are stabilized and strengthened by inclusion of at least one thin stabilizing wire 26 in the frame 22 and by encapsulation in cylindrical epoxy manifolds that are cast around the shrink-tubing and the at least one thin stabilizing wire 26 by use of a mold of silicone tubing. The two shrink-tubing segments 4' will eventually become the inflow and outflow ports for the CPD 70.

Figure 4A:
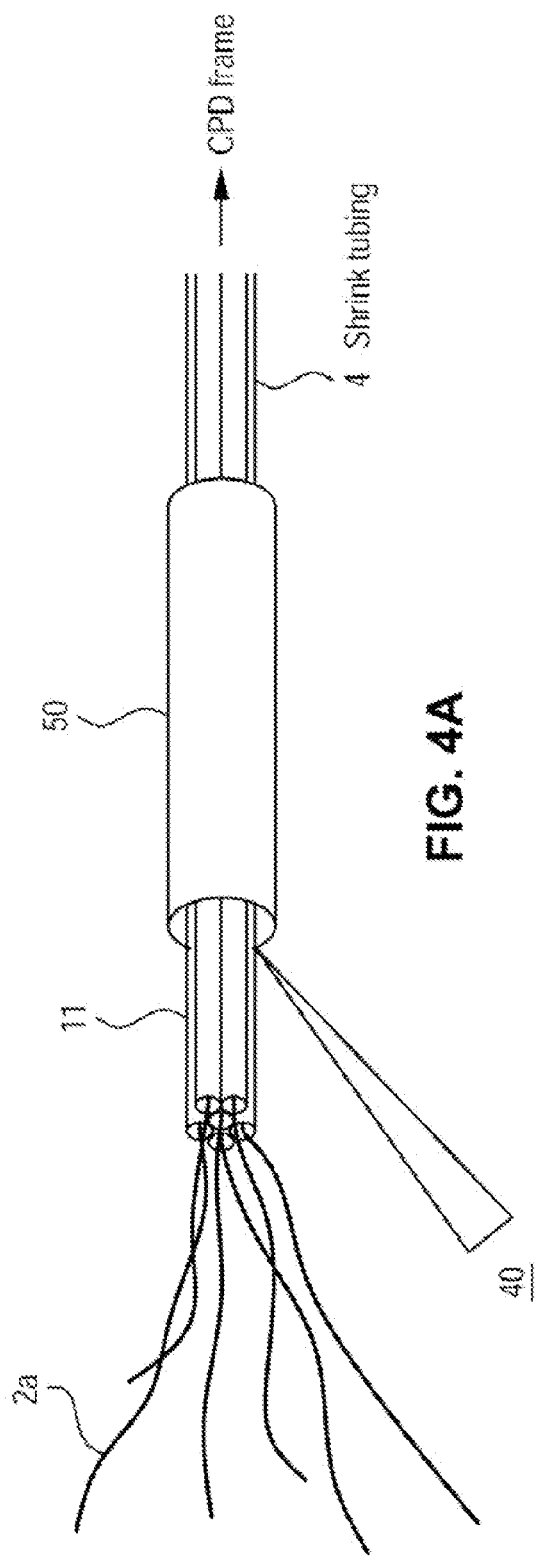
FIG. 4A and FIG. 4B schematically show creation of manifolds for culture/perfusion devices.
Figure 4B:
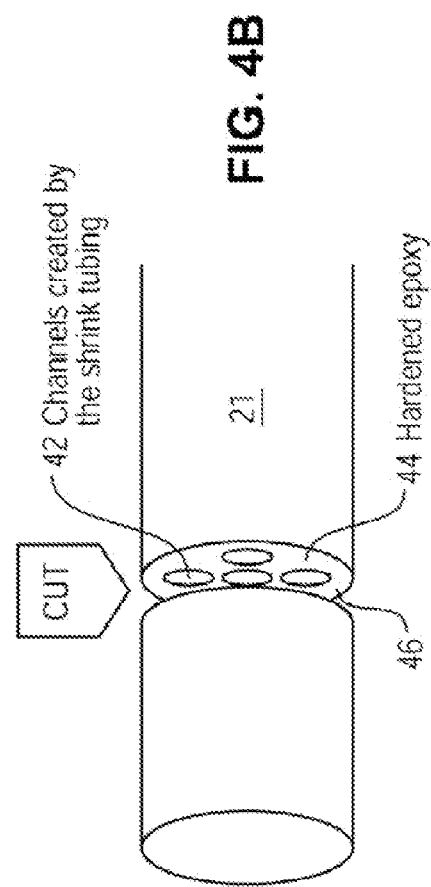

Referring now to FIG. 4A and FIG. 4B, there schematically shown is a method for creation of manifolds for culture profusion devices. FIG. 4A particularly shows a plurality of shrink-tubing/mandrel assemblies 11 pulled through a sleeve of, for example, silicone tubing 50. An epoxy glue 40 is injected to fill the silicone tubing 50 and allowed to harden.

FIG. 4B particularly shows the condition after the epoxy glue 40 has hardened and the silicone tubing 50 is slit open and removed. Remaining is a hardened epoxy rod 44. The epoxy rod 44 is cut after the mandrels have been retracted behind the cutting spot leaving channels 42 created by the shrink tubing. The ends 46 of many shrink tubes may be integrated to form a manifold 21. Stacking of individual CPDs or CPD frame assemblies can be used to create 3D vessel arrays.

Alternative Methods

Figure 5A:
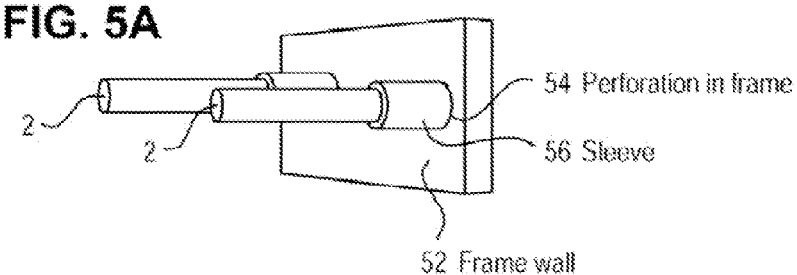
FIG. 5A, FIG. 5B and FIG. 5C schematically show an alternative design for microfabricated culture/perfusion devices.
Figure 5B:
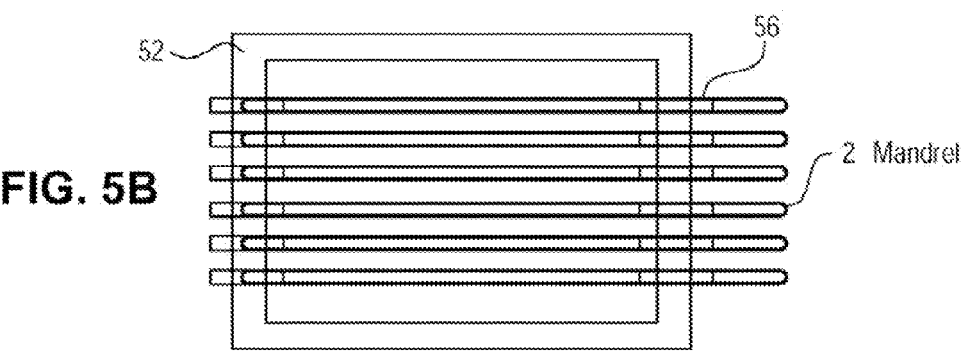
Figure 5C:
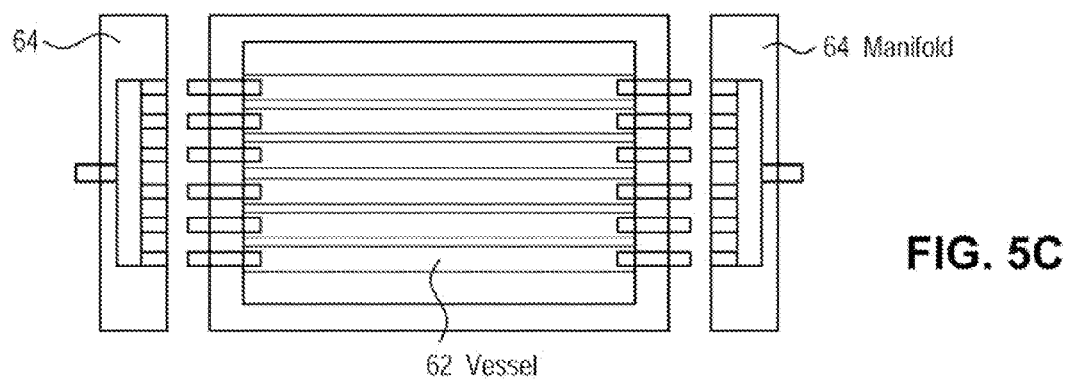

Referring now to FIG. 5A, FIG. 5B and FIG. 5C, there schematically shown is an alternative design for microfabricated culture/perfusion devices. FIG. 5A particularly shows a set of mandrels 2 introduced through small perforations 54 in a frame where the perforations have sleeves 56, which substitute for the shrink tubing. FIG. 5B particularly shows a CPD before cell seeding including a set of mandrels 2 mounted in a frame wall 52.

FIG. 5C particularly shows an alternate example of a culture/perfusion device with vessels 62 where microfabricated manifolds 64 may be attached to the sleeves 56 on the outside of the frame 52. The vessels 62 are grown on mandrels as shown herein and remain after the mandrels are removed. Microfabrication methods, such as micro molding, may be used for the mass production of such CPD frame assemblies.

Vessel Creation and Perfusion

Figure 6:
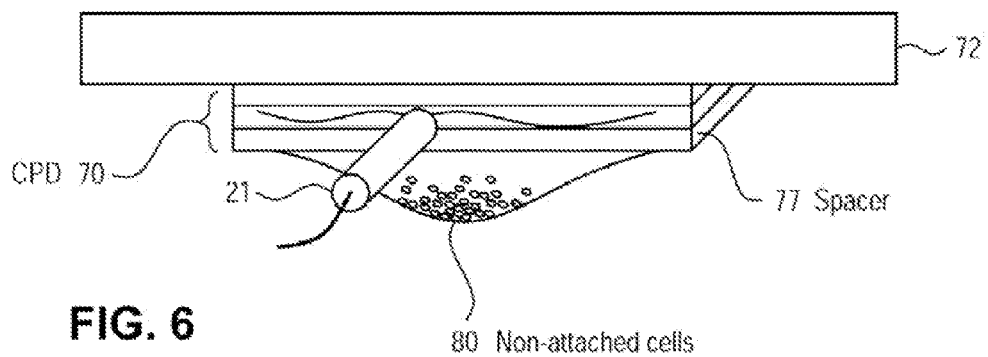
FIG. 6 schematically shows a cell-seeding procedure.

Referring now to FIG. 6, there schematically shown is a cell-seeding procedure. In order to prepare the CPDs 70 for cell seeding, they are first cleaned and then UV-sterilized Under sterile conditions, the CPDs are fixed to a surface, e.g. the bottom of the Petri dish 72. The inner window 76 (as shown in FIG. 3B) of the CPD frame assembly 70 is then filled with a solution that contains an attachment-protein, such as laminin-1, and equivalents. One or more spacers 77 may be used as necessary. After an incubation period, the attachment-protein containing solution is removed, and a suspension of the desired cell type (e.g. smooth muscle cells, endothelial cells, and in some cases pericytes, and fibroblasts, as well as precursor cell types including stem cells) in culture medium is then transferred into the window 76 of the CPD 70.

Cell seeding may be done by filling a volume of cell suspension into the window, and flipping the CPD frame assembly 70 upside down, thus creating a hanging droplet 80. During an incubation period of about 45 min., a large number of cells will attach to the mandrel/shrink tubing assemblies within the CPD frame assembly. Excessive cells will sink into the tip of the hanging drop and may be easily collected and discarded. The Petri dish, containing one or more CPD frame assemblies, is then returned into an upright position, filled with culture medium until the CPD frame assemblies are flooded, and incubated. The incubation conditions in one example were in an environment of 5% $CO_2$ at 37° C. The cells attached to the mandrel/shrink tubing assemblies will spread out and multiply, forming concentric monolayers (e.g. endothelial cells) or multilayers of 150 µm and more in thickness (e.g. smooth muscle cells).

At the desired wall configuration or thickness the mandrels are extracted, thereby creating hollow cellular tubes. Thinner walls may be protected from rupture by casting a gel such as for example, agarose, collagen, a gel of basement membrane proteins or the like, around the cell sleeves prior to mandrel extraction. The manifolds of the CPD frame assemblies are then connected to a perfusion system and perfused with the fluid of choice, such as growth medium.

In another embodiment, a method for the creation of endothelial "parent" vessels from human vascular endothelial cells (HUVEC) comprises the steps wherein:

The culture device is first cleaned and then sterilized by UV exposure for 30 min, from each side. Under sterile conditions, the device is fixed to the bottom of a Petri dish with sterile strips.

The inner window of the device is then filled with an attachment-protein solution of laminin-1. Other attachment proteins may also be used such as fibronectin, vitronectin, fibrin, arginine-glycine-aspartate motif (RGD) proteins, RGD-peptides, gelatin, collagen, different collagen sub-types and equivalents.

After overnight incubation, the attachment-protein containing solution is removed, and a suspension of human vascular endothelial cells in culture medium is then transferred into the window of the device.

The Petri dish is then flipped upside down, thus creating a hanging drop of cell-medium suspension in the window of the device. After a 45 min. incubation period in a cell culture incubator (5% $CO_2$, 37° C.) a large number of cells will be attached to the mandrel/shrink tubing assemblies within the devices.

The Petri dish is then brought back into the upright position, and filled with growth medium for human vascular endothelial cells until the device is submerged.

Cells not bound to the mandrels will float off and can be aspirated and discarded.

The Petri dish is then placed in an incubator (5% $CO_2$, 37° C.). The cells attached to the mandrels will spread out and multiply, forming concentric monolayers of human vascular endothelial cells.

The culture medium is then removed from the Petri dish. A collagen solution is filled into the window of the culture device, and allowed to solidify, thus embedding the mandrel with the cell layer.

The human vascular endothelial cells will form sprouts into the collagen gel. The mandrel is then slowly extracted, leaving behind a perfusable "parent" microvessel of human vascular endothelial cells.

The manifolds of the device are then connected to a perfusion system and perfused with human vascular endothelial cells growth medium.

Perfusion System

The CPDs may be attached to perfusion systems either in linear or in circulatory mode. A linear setup may be created with a gravity flow system, or a commercially available or custom-built syringe pump. Syringes are filled with perfusion medium, mounted into the syringe pump and connected to the upstream ends of the CPDs via gas-tight tubing. The CPDs may be stored in an incubator under sterile conditions or a sterile cell culture environment may be established within the CPD. The downstream manifold of the CPDs are connected to end reservoirs that collect the perfusate. A circulatory system may be built by using a peristaltic pump. Both, the linear and the circulatory system may be fitted with devices for gas exchange. Gas concentration, perfusion pressure, flow, temperature, and the concentration of nutrients and metabolic byproducts are measured with sensors. The collected data may be fed into a feedback loop, allowing for tight control of the desired parameters.

Specific Applications

Models for Angiogenesis Related Research

Figure 7:
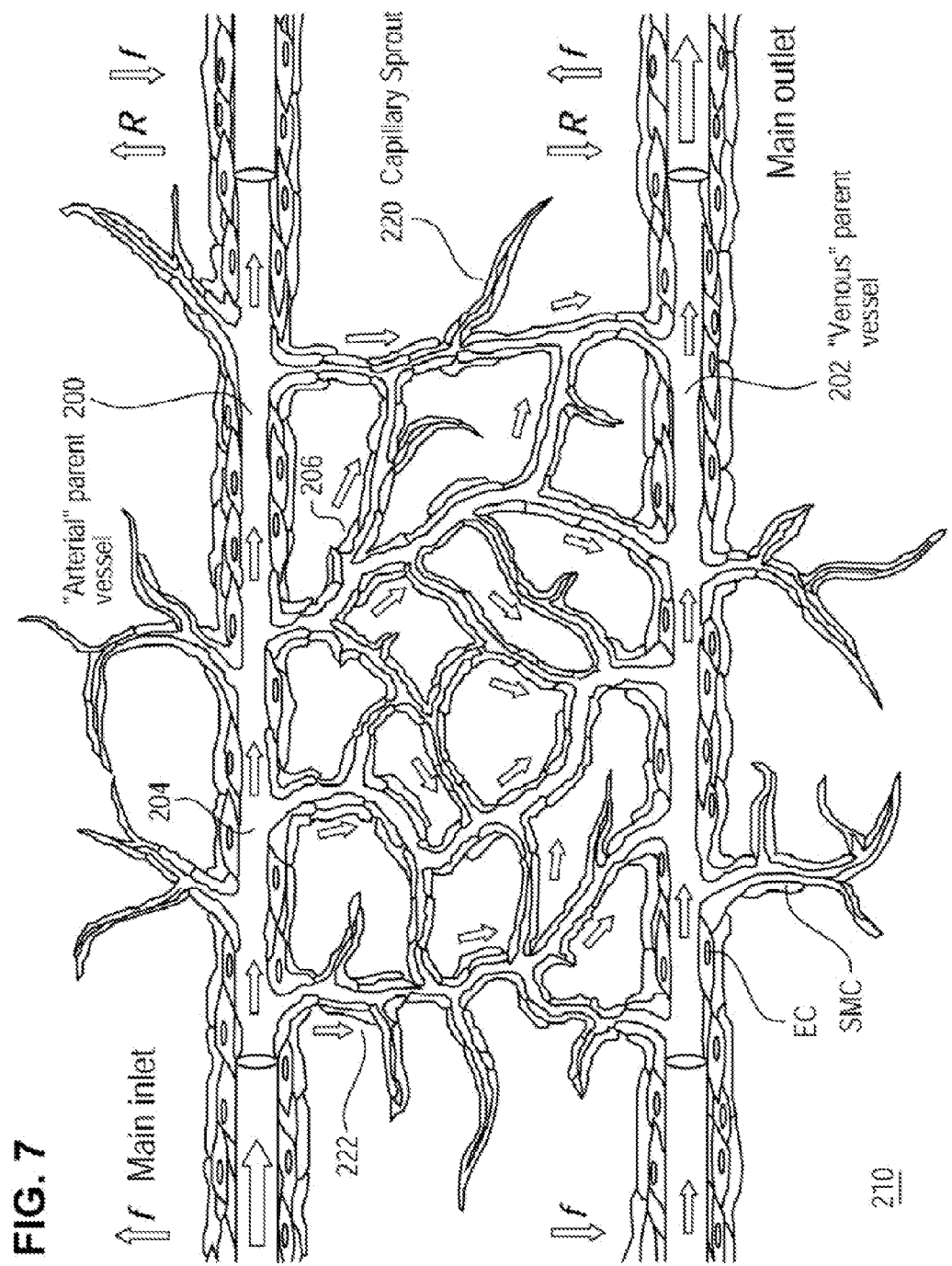
FIG. 7 shows a schematic of a capillary network between two bioartificial parent vessels.

Referring now to FIG. 7, FIG. 7 shows a schematic of a microvessel network between two bioartificial parent vessels 200, 202. The fluid perfusate 204 is re-routed through the capillaries 206 by decreasing the flow (f) into the "venous" parent vessel 202, and increasing the resistance (R) in the "arterial" parent vessel 200. Consequently, the perfusate 204 is driven from the vessel with higher pressure to the vessel with lower pressure, simulating natural blood flow from the arterial end to the venous end of the capillary bed. For example, in one example embodiment, both parent vessels are perfused at the same rate and the resistance in the outlets is kept the same. If the flow is increased into the first vessel and, at the same time flow is decreased into the second vessel, the perfusate would become re-routed from the first vessel into the second vessel. In order to facilitate the re-routing even more in other embodiments, the resistance at the downstream end of the first vessel could be increased and lowered in the second vessel. This could be done by raising or lowering the back pressure. In an alternate embodiment the downstream end of the first vessel and upstream end of the second vessel would be completely closed; then the perfusate would enter through the first vessel and proceed to enter the second vessel through the microvessel network and leave through the downstream end of the second microvessel parent vessel.

The mandrel method may be also used for the development of models for angiogenesis research, leukocyte adhesion assays, or as needed for pharmaceutical testing and research in wound repair and diseases of aging, cancer, psoriasis, diabetic retinopathy, inflammatory diseases; stroke, and atherosclerosis. Using endothelial cells only, or combinations of endothelial cells, smooth muscle cells, and pericytes, parent bioartificial microvessels (BMVs) can be cultured around micron-diameter mandrels, and embedded into a supportive gel of extracellular matrix. In some cases additional cell types may be used including fibroblast cells, progenitor cells, stem cells and equivalents. The mandrels will then be extracted, leaving behind patent endothelial cell tubes within the extracellular matrix gel 210. The extraction may be done by hand, or by aid of an automated device, and with speeds varying from extremely slow to extremely fast. Other variations may include the extraction of the mandrel from bioartificial microvessels in a frozen state. coating of the mandrels with a thermo-responsive polymer, or pulling on either end of the mandrel, and thereby thinning it until rupture.

The sprouting of the parent vessels into the surrounding gel 210 will be induced by compounds, such as basic fibroblast growth factor (bFGF), vascular endothelial growth factor (VEGF), and the phorbol ester, phorbol 12-myristate-13-acetate (PMA), which are added to the gel and/or perfusate (e.g. growth medium). Other growth factors that can be used to induce sprouting include long $R^3$ insulin-like growth factor ($R^3$IGF-1), insulin like growth factors (e.g. IGF-1), Interleukin-8 (IL-8) and human epidermal growth factor (hEGF), connective-tissue growth factor (CTGF), heparin-binding EGF like growth factors (HB-EGF), angiopoietins, placental growth factor, cytokines, various chemokines (e.g. SDF-1α). TGF-β, and soluble mitogens. Further, the density of seeding of cells contributes to the induction of a sprouting competent phenotype.

Complex microvessel networks 222 may be created by establishing a pressure difference between two adjacent parent bioartificial microvessels, thereby imitating arterial and venous blood flow. The fluid flow will then be re-directed from the "arterial" bioartificial microvessel through the interconnected sprouts into the "venous" bioartificial microvessel.

The perfusate may advantageously comprise oxygenated cell growth medium, free of serum and angiogenic or angiostatic substances. In another example the perfusate may be an oxygenated cell growth medium, supplemented with serum, and/or angiogenesis influencing compounds. In yet another example embodiment the perfusate may be an oxygenated physiological salt solution. In some cases the medium is buffered for physiologic ranges. In another example the perfusate may include oxygenated blood, blood components, or blood substitutes. In yet another example embodiment the perfusate may not be an oxygenated, and oxygenation of the system is achieved by diffusion through the matrix. In yet another example embodiment angiogenic or angiostatic compounds may be added to a perfusate.

In one example embodiment, angiogenic and angiostatic compounds or the like are added to the matrix. In yet another example embodiment cells comprise genetically modified cells that release products into a perfusate or into the matrix. In yet another example embodiment the matrix may advantageously comprise fibrin, collagen, basement-membrane matrices, extracellular matrix components, and gelatin. One type of useful matrix is Matrigel® gel. In another example embodiment the matrix may comprise agar, agarose, alginate, or silica gel.

In another example embodiment basement membrane based matrix may include collagen type IV, perlecan, laminin, integrins, enactins, dystroglycans, type VII collagen fibers and collagen type VII microfibrils. In still another embodiment extra cellular based matrix may include proteoglycans, glycosaminoglycans, heparin sulfate proteoglycans, chondroitin sulfate proteoglycans, keratin sulfate proteoglycans, hyaluronic acid, collagen, fibronectin, vitronectin, elastin, and laminin.

In one example embodiment, the cells may be selected from the group consisting of endothelial cells, smooth muscle cells, pericytes, fibroblast cells, progenitor cells, stem cells, muscle cells, liver cells, lung cells, skin cells, epithelial cells, human cells, animal cells, plant cells, eukaryotic cells, genetically engineered cells, genetically modified cells, diseased cells, virally infected cells, and cancerous cells. Similarly, the matrix may be populated with cells selected from the group consisting of endothelial cells, smooth muscle cells, pericytes, fibroblast cells, progenitor cells, stem cells, muscle cells, liver cells, lung cells, skin cells, epithelial cells, human cells, animal cells, plant cells, eukaryotic cells, genetically engineered cells, genetically modified cells, diseased cells, virally infected cells, and cancerous cells, either dispersed throughout the matrix, or locally concentrated. In some cases a fragment of healthy or diseased tissue, such as cancer tissue is embedded into the matrix. In other cases virally infected or genetically engineered tissue is embedded into the matrix.

Sprouting from parent vessels may be microscopically studied in vitro, in sectioned material or in whole-mount preparations. Perfusion of the bioartificial microvessels with fluorescent solutions (e.g. fluorescent dextrans) aids analysis of the sprout diameter, the patency of sprout lumens, and the degree of anastomization. 3D reconstruction of sprout morphologies may be performed by z-axis stacking of epifluorescence images taken by a confocal microscope. The synthesis of a pericellular basement-membrane matrix by sprouts 220 may be monitored in whole mounts and in histological (paraffin) sections by immunolabeling with anti-laminin and type IV collagen primary antibodies and fluorescent or peroxidase-tagged second antibodies.

In composite EC/SMC sprouts, the spatial relationships between the two cell types may be examined by labeling endothelial cells with a FITC-monoclonal antibody (MAb) to human CD31 (clone P2B1—Chemicon) or FITC-UEA 1 agglutinin—a specific marker for human endothelial cells, smooth muscle cells may be labeled with a MAb to human alpha-SM actin followed by RITC-anti-mouse second antibodies. Details of luminal structure and interaction between endothelial cells and smooth muscle cells may be obtained from paraffin sections labeled with the aforementioned reagents.

The described fabrication methods are the foundation for commercial mass-production of angiogenesis devices with a high repeatability. With suitable preservation (e.g. cryostorage), pre-grown parent vessels or whole microvessel networks could be made available to researchers in off-the-shelf fashion.

Coronary-artery Substitutes

For the creation of coronary-artery substitutes, mandrels with an outer diameter selected to yield a coronary artery substitute having a vessel lumen with an inner diameter of approximately 4 mm to 5.5 mm. Alternatively, the mandrel may be a hollow tube that is perfused and permeable enough to allow for exchange of nutrients and gases during the growth period of the coronary-artery substitute. The coronary-artery substitutes may be grown either solely from smooth muscle cells, thus presenting a structure analog to the media layer in blood vessels, or made as composite structures from two or three cell types.

Smooth muscle cells are seeded onto the mandrels and grown to circular layers of 300-500 µm. In order to speed up the creation of coronary artery substitutes, the SMC-phenotype may be manipulated in such way that the cells are brought into a highly proliferative phenotype during the initial growth phase, and then switched to a differentiated state after the vessel wall has reached the desired thickness. The phenotype switch will cause the smooth muscle cell's to dramatically slow down their growth rate, and induce the production of extracellular matrix proteins, such as collagen and elastin, which affect mechanical properties of the vessels. The phenotype switch may be achieved by controlling the expression of certain genes. For example, with aid of a tetracycline-responsive promoter, gene expression (e.g. for elastin) may be suppressed until the vessel wall has reached the desired thickness (Clontech Laboratories Inc.). Omitting tetracycline from the growth medium will then activate the inserted gene. Over-expression of elastin, for instance, will inhibit further cell proliferation and exert structural and signaling functions within the vessel wall. Mechanical conditioning, e.g. pulsatile flow may be used to strengthen the coronary-artery substitutes, and induce physiological alignment of the cells.

Other external or internal "phenotype switches" may be potentially used, as well. For example, endothelial and smooth muscle specific genes or other candidates may be engineered via recombinant DNA techniques to be expressed via native, cell or tissue specific, inducible, and heterologous promoters. Additionally, advanced lentiviral transduction systems provide the ability to integrate a gene of interest under the transcriptional control of a desired promoter into quiescent or other cell types (Clontech Laboratories Inc., Invitrogen Corp.). These methods allow manipulation of gene dosage, expression levels, mutational analysis, and regulation, all of which allow control of cellular phenotypic switches.

Endothelial cells may be seeded into the SMC sleeves either directly after removal of the mandrel, or after the conditioning and restructuring of the smooth muscle cells. Endothelial cell seeding may be done by infusion of an endothelial cell suspension into the SMC sleeve. The flow is then stopped for a period of time to allow proper attachment of the endothelial cells. If necessary, the vessels may be rotated, or repeatedly flipped upside down in order to facilitate an even distribution of the endothelial cells.

Alternatively, endothelial cells may be seeded onto the mandrel first. In that case smooth muscle cells are seeded onto a confluent endothelial cell layer, For this method, it will be necessary to prevent the endothelial cells from migration towards the periphery of the coronary-artery substitute, which is richer in oxygen and nutrients.

If desired, seeding fibroblast cells onto the outside of the SMC sleeves can create an adventitial layer. In some cases the seeding of pericytes is included for growth of vessels where they can contribute to formation of the basement membrane. In other cases seeding of progenitor and/or stem cells is also included for growth of vessels.

The cells for creating coronary-artery substitutes may be derived from autologous, heterologous, or xenogeneic material. The cells may be stem cells, precursor cells, or differentiated cells. The cells may be genetically modified to achieve a specific phenotype or to lower the immune response of the host organism.

The herein-disclosed CPD method provides the option for mass-producing off-the-shelf vessel substitutes, or vessel substitutes that are custom designed for the recipient. The herein-disclosed CPD method is also suitable for the development of models for tissue engineering of coronary-artery substitutes, for research in atherogenesis, arteriogenesis, for research in the interaction of different vascular cell types with each other and with extracellular matrix components, for studies on the effects of nitric oxide, and for the study of various pharmaceuticals.

Blood and Lymphatic Vessels of Different Size or Type

The herein-disclosed CPD method may be used to create blood vessels in diameter and type other than coronary arteries. Changing the diameter of the mandrel will vary the vessel diameter. In some cases the mandrel can be from about 20 microns to about 500 microns approximating the size of smaller vessels. In other cases the mandrel may be from about 200 microns to about 5.5 mm approximating midsized to larger vessels. The type of the vessel (e g. arterial, venous, lymphatic) may be varied with the phenotype of the cells, and/or the time point when the proliferation of the cells is inhibited. Veins, for example, contain only a small smooth muscle cell layer.

Other Tubular-like Tissues

The herein-disclosed CPD method may be used for the engineering of other tubular tissues, such as bile duct, lacrimal duct, pharyngotympany tube, oviduct, vas deferens, ureter, urethra, pulmonary airways etc. The herein-disclosed CPD method may also prove useful for the generation of nerve conduits from different cell types, including glial cells, for guidance of neural growth and repair.

BAV Systems for Engineered Tissues

The herein-disclosed CPD method may be used for the engineering of tissues and organs by using arrays of removable mandrels as scaffold. The cells of the desired tissue/organ (muscle, liver, kidney, lung, skin, etc,) are seeded onto the attachment-protein coated mandrels. These mandrels may be made from solid fibers or wires, or, alternatively from perfusable permeable tubes, such cellulose. The mandrels are separated from each other in a precise spacing that allows the single cell sleeves to merge. With this method, sheets or blocks of tissue may be formed. The mandrels are then extracted (or differently removed), and the bioartificial tissue is internally perfused by aid of a perfusion system.

Wound Healing Device

Pre-manufactured bioartificial vessel systems may be used to assist in wound healing, such as for chronic ulcers in diabetic patients. Bioartificial microvessel networks could be embedded into patches of supportive materials (e.g, from extracellular matrix gels, enriched with angiogenic growth factors), and placed onto the wound. Autonomously perfused with oxygenized nutrient solutions, the bioartificial vessel would facilitate the sprouting of the donor vasculature and skin. Alternatively, such a bioartificial vessel patch could be sandwiched between the wound and a skin graft, and facilitate the in-growth of the graft.

Gene-therapy Device

Bioartificial vessels could be used for implantable drug delivery devices. Cells, taken from a patient, could be genetically modified in vitro to produce a certain protein (hormone, enzyme etc.). These cells may be then grown into bioartificial vessels or vascular networks, using the aforementioned method. Re-implanted into the host, the cells continue to produce the target substance and release it locally or systemically.

Artificial Tissues and Organs

Tissue engineered vascular networks, as described above, may be used for the creation of tissues, or even whole organs. One approach is the creation of one or more in vitro perfused parent vessels. Parenchymal cells, from the desired tissue or organ are seeded around the parent vessels, as for example, in a gel. Different stromal cell types can be added as well (e.g. immune cells, inflammatory cells, pericytes, fibroblasts, or endothelial cells). The parenchymal cells are supplied with nutrients and oxygen via the parent vessels. Parenchymal cell multiplication increases demand for nutrients and oxygen. The cells release angiogenic factors, and stimulate the vessels to sprout. The vessel system sprouts in the same rate, as the tissue grows—very similar to the natural growth. Therefore, this system would be also a good model for studies in developmental biology.

Another approach utilizes parallel arrays of mandrels as a scaffold for parenchymal cells. As the parenchymal cells multiply, cell layers are formed around the mandrels. Eventually the space between all the mandrels is filled with parenchymal cells, resulting in a sheet of tissue. Upon removal of the mandrels, the tissue may be perfused through the channels, left behind by the mandrels. Those channels can become endothelialized through luminal seeding. The approach is not limited to 2D. Either several sheets may be stacked, or 3D scaffolds may be used. The inventor herein has used 2D arrays as well as 3D arrays for the engineering of muscle tissue.

In yet another approach, layers of tissue and layers of vascular networks could be created independently, and then intermittently stacked. All these approaches can produce either simple models with one or two cell types, or rather complex constructs composed of several cell types.

Figure 8A:
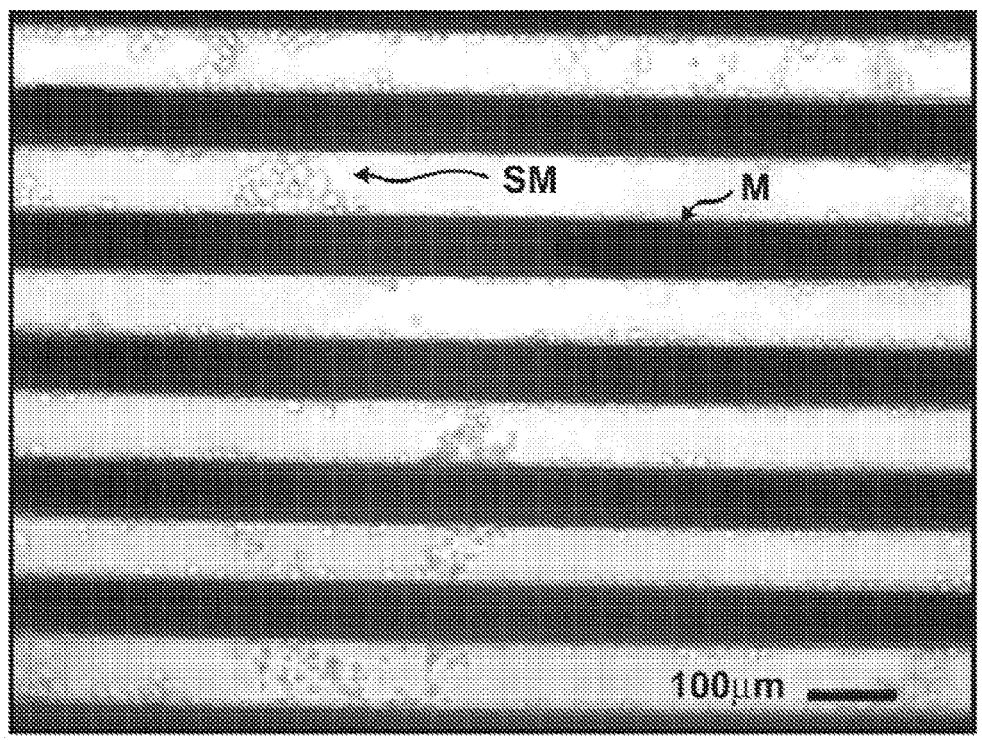
FIG. 8a shows an in vitro image of an example of a plurality of mandrels after seeding with smooth muscle cells.

Upon implantation, the tissues or organs, engineered with these methods could be either connected directly to the blood stream, or kept perfused by a perfusion system until the host vasculature has grown into the graft, Example of Perfused Tissue Engineered Muscle Construct Referring now to FIG. 8a, an in vitro image of an example of a plurality of mandrels after seeding with smooth muscle cells is shown. A plurality of mandrel-and-shrink tubing units M were sandwiched on a Mylar® frame. The distance between the mandrels M was adjusted to approximately 100 µm. The ends of all shrink tubing segments were combined in one upstream and one downstream manifold (not shown) The Mylar frame was sterilized, laminin coated and seeded with a suspension of $5 \times 10^6$ rat aortic smooth muscle cells SM (RASMCs)/ml. The cells SM attached to each individual mandrel M and multiplied, thus forming circular layers. After 10 days, the individual layers had merged and resulted in one thick sheet or plate of smooth muscle cells. After additional 7 days in growth medium, the medium was supplemented with 50 U/ml heparin for another 7 days. Then, all mandrels were extracted, and the tissue perfused with heparin-medium at a rate of 10 ml/day. The perfusion chamber was kept fixed to the bottom of a 100-mm Petri dish filled with heparin-medium.

The SMC plate was perfused for 11 days. Over that time, the channels CH remained functional and remained clearly visible in vitro (as best shown in FIG. 8b).

Figure 8B:
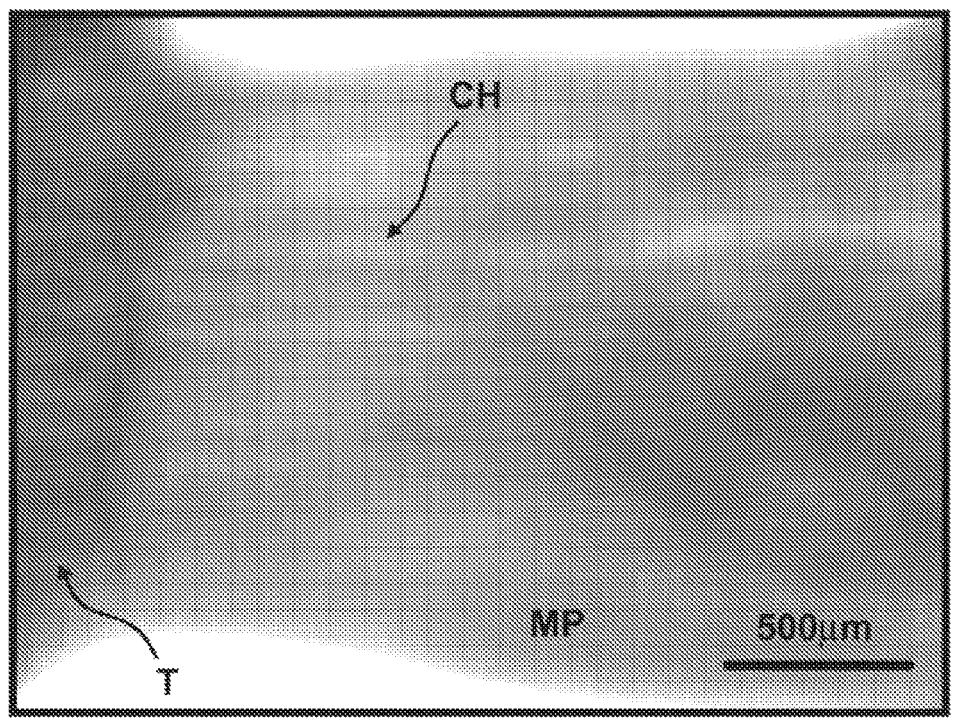
FIG. 8b shows an example of a perfused muscle plate.

Referring now to FIG. 8b, an example of a perfused muscle plate MP is shown. Fluid is shown perfused through the tubing ends (T) into channels (CH) left behind by the extracted mandrels.

Referring now to FIG. 9, an alternate embodiment of a CPD is schematically shown. In one example, a CPD 900 includes a layer 902 juxtaposed between a first glass slide 904 and a second glass slide 920. The layer 902 has a thickness suitable for embedding a plurality of fluid ports connected by channels 922. The plurality of fluid ports include a cell suspension port 914, a plurality of inlet ports 912 and a plurality of outlet ports 918. Ports that are connected by channels 922 to allow for passage and sharing of fluids function similarly. Multiple ports, such as ports 912, are arranged to provide multiple access points. Other applications may advantageously employ microfluidic designs with fluid chambers and ports created in microfluidic materials. Similarly, the layer may comprise silicone or other materials suitable for use in microscopy or microfluidic applications. A collagen chamber 906 is advantageously located for access by a pair of hollow, flexible glass capillary tubes 916, or equivalents. The number of capillary tubes employed may range from one to substantially more than two as may be accommodated by the size of the CPD and the number of vessels being created. Each of the plurality of ports and chambers may be accessed through the layer by one or more syringe pumps through tubing inlets 940A, 940B, where the syringe pumps are attached to syringes having needles. While only two syringe pump tube inlets 940A, 940B are shown to simplify the drawings, it will be understood that separate syringe pumps, syringes or equivalents may be used for injecting or extracting materials into each chamber and/or port as the case may be. In one embodiment, the syringe pumps are coupled to gas tight syringes.

Having described the features of the alternate embodiment CPD 900, it will aid the understanding of the invention to now describe one method for constructing the CPD. In one example employing a silicone layer for layer 902, a pattern of holes and channels is punched into a silicone layer covered with an adhesive top layer 943 and adhesive bottom layer 945. Then, hollow needles are punctured through the silicone, which are then used to guide polyimide-coated fused-silica capillaries 916 into the collagen chamber 906 and also into one of the inlet ports 912. The two capillary tubes are held by small-bore tubing 910, leading from the main chamber into the outlet ports 908. The silicone layer 902 is then sandwiched in between two glass slides with aid of the adhesive layers. The CPD 900 is then autoclaved and stored until use. To get the chamber 906 ready for vessel creation, a collagen solution is prepared, injected through a syringe needle directly into the collagen chamber 906, and allowed to gel in an incubator overnight. The CPD 900 is then connected to a syringe pump by injecting syringe needles into the two inlet ports.

The syringe needles are, in turn, connected to gas-tight tubing, which leads to two gas-tight syringes, filled with grow medium with well adjusted pH, and mounted into a syringe pump. The two outlet ports 908A, 9088 are connected to waste reservoirs in similar fashion. The syringe pumps, here operating as perfusion pumps, are then turned on, thereby filling the inlet ports and sequentially priming the inlet ports, the capillary tubes, and the outlet ports. When all the air is pushed out of the system, the each capillary tube is grabbed with tweezers and the ends that reach into the collagen chamber are pulled back through the collagen gel until only the ends of the capillaries reach into the matrix chamber. With this procedure, two perfusable channels are created in the collagen gel. In order to seed cells into the collagen channels, a highly concentrated suspension of endothelial cells is injected into the ports for cell suspension. The syringe pump is then turned off, and the other ends of the capillaries are then pulled back into the small reservoirs 914R that contain the cells, leading to an immediate influx of large numbers of cells into the collagen channels. The flow rate of the cells can be tightly controlled through the height of the waste reservoirs. In some cases the flow rate may be regulated to approximate in vivo flow in native capillaries and vessels. The CPD is then placed in an incubator for 45 min. for allowing the cells to attach to the walls of the collagen channels. The CPD can be flipped over several times or otherwise manipulated to distribute the cells optimally. Finally; the capillary tubes are pulled out of the cell reservoirs into reservoirs that are part of the inlet port, and the syringe pump is turned on and set to the desired perfusion rate. Excessive cells are washed out. This seeding procedure leads to two parent vessels with homogeneous monolayers of cells after allowing time for growth, where the time required is shorter for more highly concentrated numbers of cells injected into the tubes. Note that the mandrel may be removed from the matrix by extraction and/or decomposition, depending on the type of mandrel used.

Figure 10:
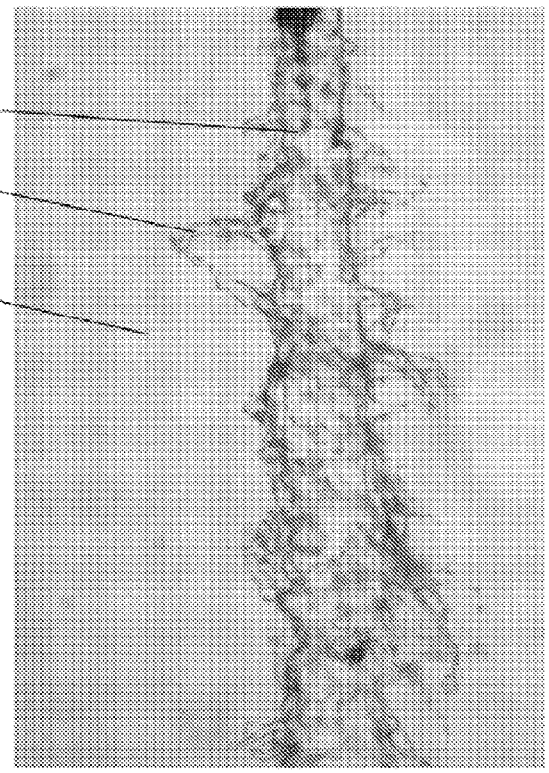
FIG. 10 shows a single parent vessel growing sprouts into the surrounding matrix.

Referring now to FIG. 10, a single parent vessel 1050 growing sprouts 1052 into a surrounding matrix 1054 is shown. When Human Umbilical Cord Vein Cells (HUVECs) are seeded into the collagen channels, the so created parent vessels begin to sprout into the collagen. These sprouts elongate and begin to branch. These branches eventually anastomoze with branches from the opposite parent vessel and, thus, form vascular networks.

Figure 11:
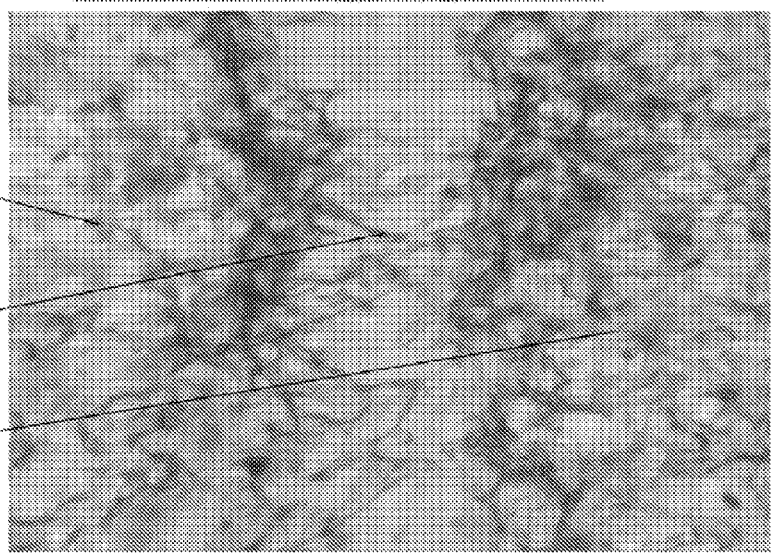
FIG. 11 shows one parent vessel connected through a network sprouts to a second parent vessel.

Referring now to FIG. 11, a first parent vessel 1102 is shown connected through a network of sprouts 1106 to a second parent vessel 1104. The sprouts 1106 have lumens and are perfused.

Protocol for Creation of Parent Vessels

Figure 12:
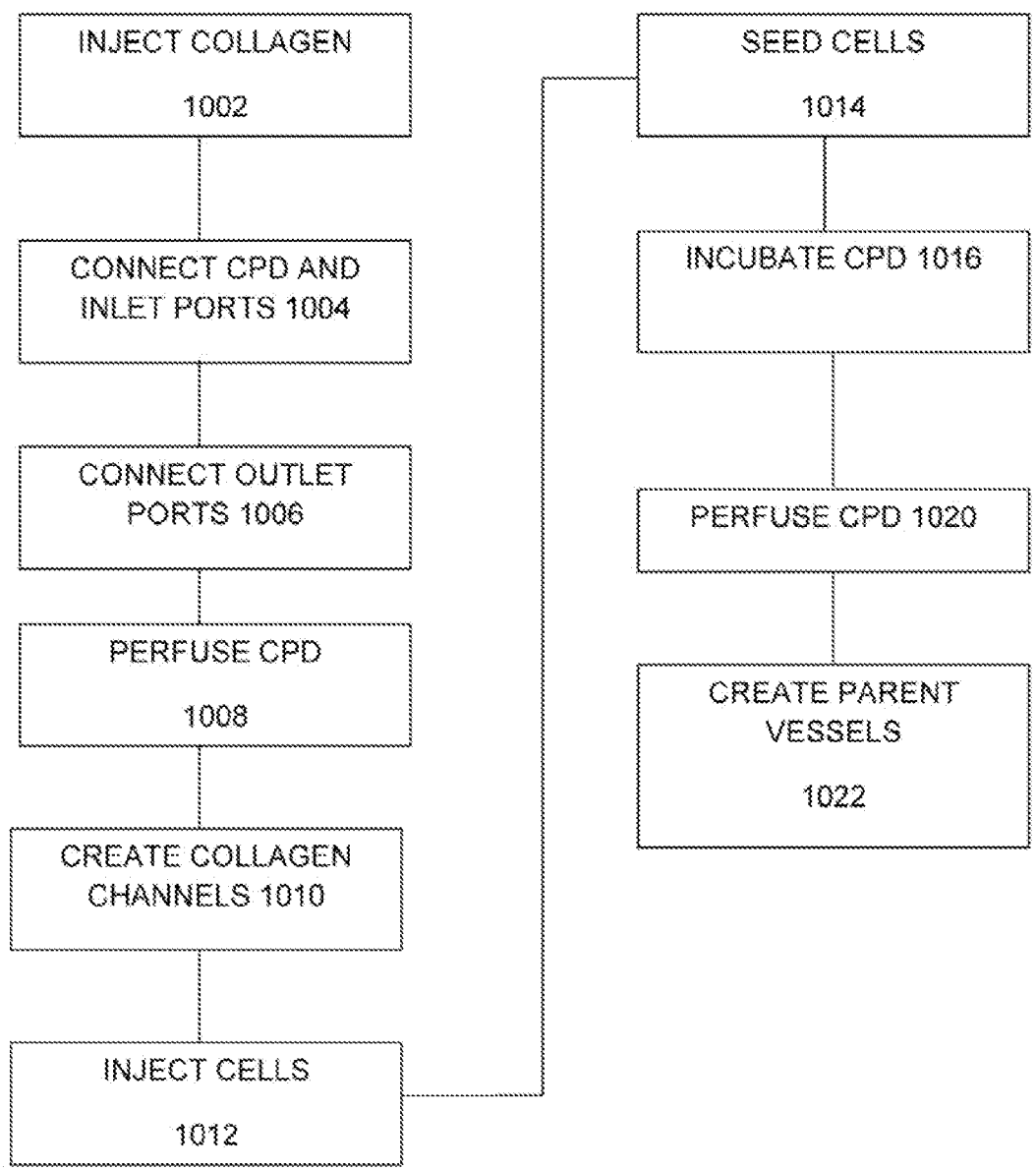
FIG. 12 an alternate method for creating parent cells by seeding cells into channels in a collagen matrix is shown

Referring now to FIG. 12, an alternate method for creating parent cells by seeding channels in a collagen matrix is shown. Having described the alternate CPD using a silicone layer, a specific example of an application for creating a microvessel system will now be described to facilitate understanding of the disclosure by those skilled in the art.

The CPD is sterilized in an autoclave, and kept in a sterile environment until use. A collagen solution is prepared and kept on ice. The collagen is filled into a small syringe. The syringe is fitted with a 30 G syringe needle, and the collagen solution is injected into the collagen chamber through the syringe needle until the chamber is completely filled with collagen 1002. A second syringe needle is injected from the opposite side of the chamber as an air outlet.

The CPD is then connected to a syringe pump by injecting syringe needles into the two inlet ports 1004. The syringe needles are, in turn, connected to gas-tight tubing, which leads to two gas-tight syringes, filled with grow medium with well adjusted pH, and mounted into the syringe pump. The two outlet ports are connected to waste containers in similar fashion (i.e. syringe needles injected into the outlet ports, with tubing leading to the waste containers) 1006.

The CPD is perfused by operating the syringe pump as a perfusion pump, thereby filling the inlet ports and sequentially priming the inlet ports, the capillary tubes, and the outlet ports 1008. When all the air is pushed out of the system (e.g. through small diameter syringe needles serving as removable air outlets), then each capillary tube is grabbed with tweezers and the ends that reach into the collagen chamber are pulled back through the collagen gel until only the ends of the capillaries reach into the chamber. With this procedure, two perfusable channels are created in the collagen gel 1010.

In order to seed cells into the collagen channels, a highly concentrated suspension of endothelial cells is injected into the ports for cell suspension 1012. The syringe pump is then turned off, and the other ends of the capillary tubes are then pulled back from the inlet ports into the small reservoirs that contain the cells, leading to an immediate influx of large numbers of cells through the capillary tubes into the collagen channels 1014. The flow rate of the cells can be tightly controlled through the backpressure (height of the waste reservoirs). The capillaries are then pulled back further into the reservoirs that are connected to the inlet ports.

The CPD is then placed in an incubator for 45 min for allowing the cells to attach to the walls of the collagen channels 1016. The CPD can be flipped over several times or otherwise manipulated to distribute the cells optimally.

Finally, the syringe pump is turned on and set to a desired perfusion rate 1020. Excessive cells are washed out. This seeding procedure leads to two parent vessels with homogeneous monolayers of cells 1022. One or more microvessel networks may be created by perfusing the parent vessels as described above.

Alternately the procedure for creating the parent vessels may also include embedding mandrels into the collagen matrix, extracting the mandrels, and infusing cells into the channels left behind by the mandrels as well as seeding cells onto mandrels as described above with reference to FIG. 1A-1C and others. The combination of the two methods allows layering of different cell types.

Protocol for Activating a Sprouting Competent Phenotype

In another example method the seeding of cell types at high-densities activates competency of the cells for sprouting as microvessels from parent vessels. The process is performed as previously discussed with CPD 900 unless otherwise noted. Images presented below are taken via brightfield or confocal fluorescent microscopy using standard techniques and reagents. Features specific to the activation of the sprouting competency phenotype are distinguished to aid understanding of the disclosure by those skilled in the art.

Figure 13A:
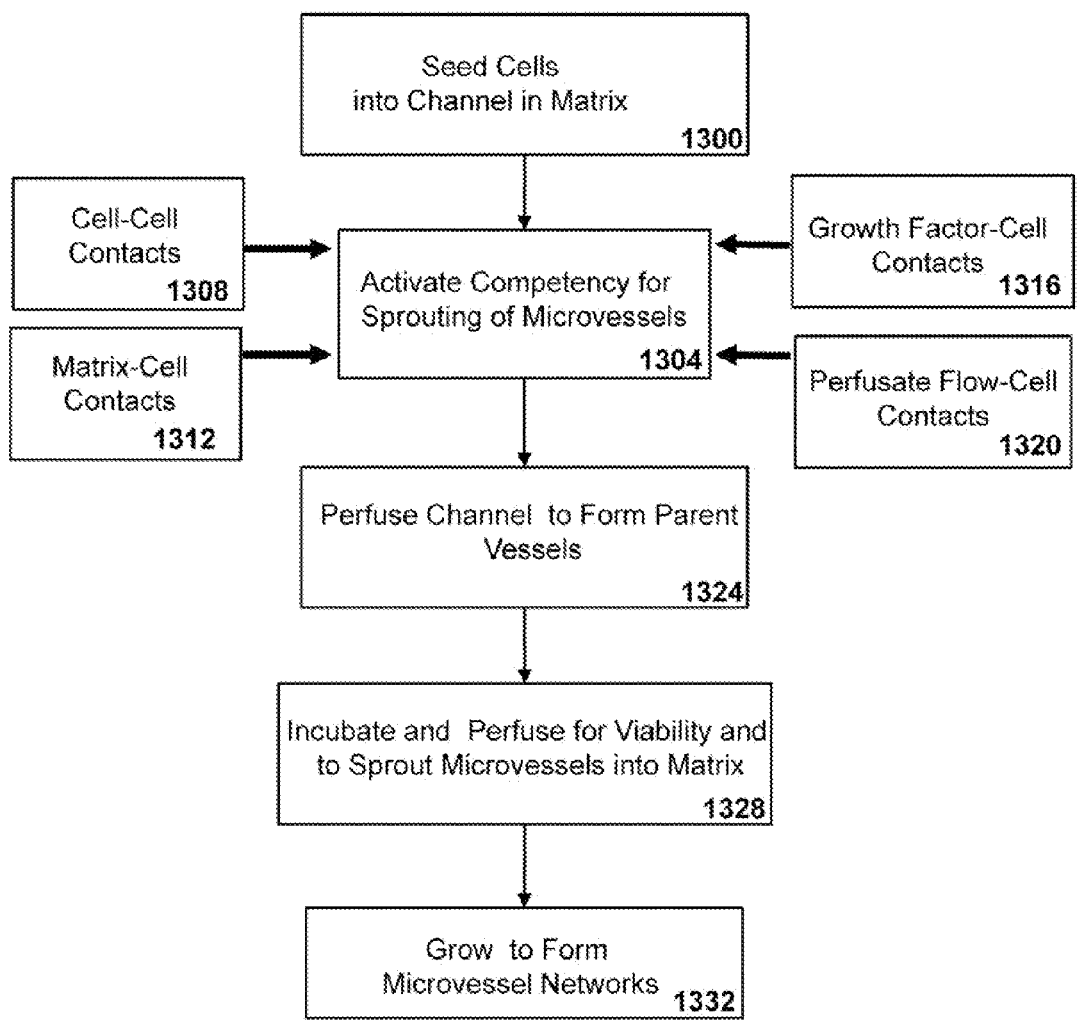
FIG. 13A shows methods for activating sprouting competency in cells and parent vessels.

Referring, to FIG. 13A, a method for forming sprouting competent cells and parent vessels is described. Cell types such as human umbilical endothelial cells (HUVECs) are seeded at high-densities 1300 where the majority of cells are in direct contact or nearly in contact with neighboring cells in the 3D space of the channel. A subset of cells is in contact with the matrix of the channel wall.

The seeding at high-density activates a competency for sprouting in the cells 1304. Without being bound to a particular theory, it is believed that this phenotype is from cell-cell contacts that are present when cells are seeded at a high-density which activates cellular signaling induced from homophilic contacts between the cells 1308. It would also be expected that heterotypic interactions between different cell types could also contribute to activate the sprouting competent phenotype.

Additionally, contacts between the cells and the matrix components of the channel wall may contribute to the activation of sprouting competency 1312. Further, there are contributions to activation of sprouting competency from soluble growth factors 1316 contacts with cells. For example, growth factors present in the perfusate medium, were previously shown to induce sprouting (as shown in FIG. 7, for example).

There may also be contributions from mechanical sensing of the perfusate flow by cells during the seeding and perfusing of the cells 1320.

Cellular signal transduction events likely activate the sprouting competent state 1304 observed for the cells. When the cells are perfused in the matrix channels they grow or come from cell migration forming parent vessels 1324 with continuous lumens. The parent vessels are perfused and incubated for viability and to sprout microvessels into the matrix 1328. The trigger for the sprouting competence phenotype initially appears to be a phenomenon related to the seeding density, but ongoing analysis will delineate if this phenotype can be regulated further. Further growth leads to the formation of complex 3D microvessel networks 1332. In some embodiments microvessels networks from different parent vessels merge via anastomosis.

Without being bound to a particular theory, one hypothesis is that the sprouting competency phenotype is derived from the sum of contacts that mediate cellular signaling that depends on the density of seeding. Additionally, contribution of the physical forces from seeding at high-density can be evaluated for the sprouting competency phenotype. For example, seeding of endothelial cells at high-density results in physical compression where the endothelial cells are balled up during the process. Since endothelial cells are typically spread out laterally in vessel formation this is not initially possible during seeding where cells are tightly packed together and growth into the matrix may be favored triggering the sprouting phenotype.

Figure 13B:
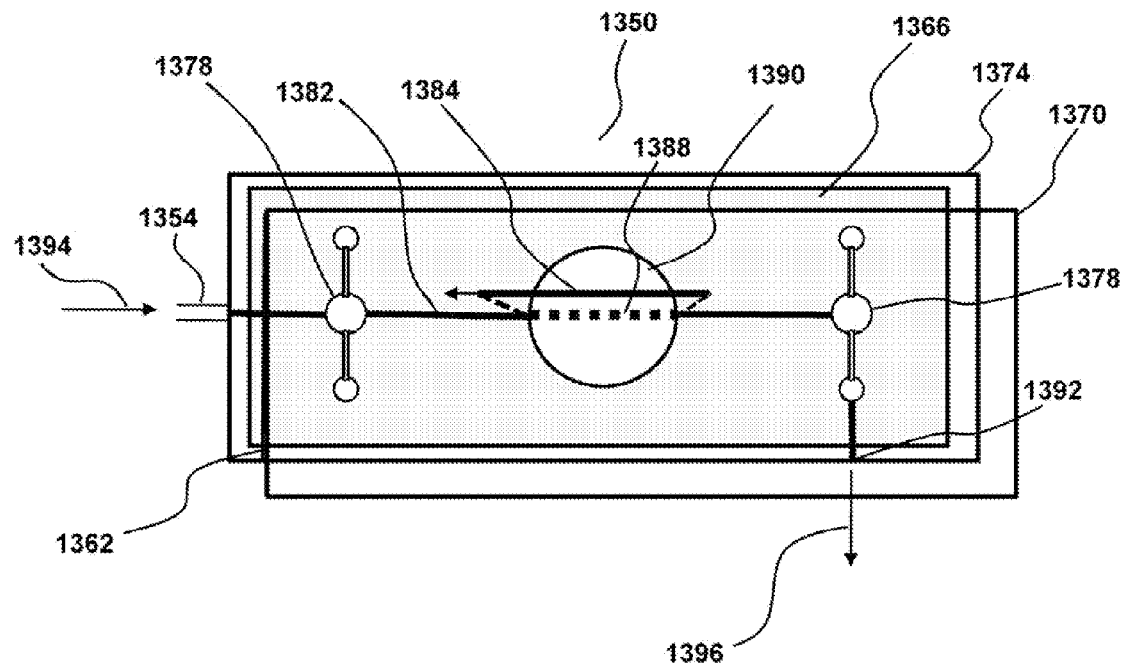
FIG. 13B schematically shows an embodiment of a CPD.

Referring now to FIG. 13B, an alternate cellular perfusion device CPD 1350 is shown. The CPD 1350 provides for long term continuous perfusion by having a single inlet fluid port 1354 and single outlet fluid port 1392 to enhance functioning and efficiency of perfusion. A silicone layer 1366 is sealed within a first slide 1370 and second slide 1374 using oxygen plasma indicated by seal 1362. The resulting seal 1362 is watertight under pressure that may be generated by long term perfusion.

The single inlet fluid port 1354 allows priming and seeding of cells at high-densities via injection into a priming chamber 1378. A conduit 1382 is coupled to a glass capillary mandrel 1384 within a collagen matrix chamber 1390. Collagen can be injected into the matrix chamber 1390 around a glass capillary mandrel 1384 forming the matrix in the collagen chamber 1390. Removal of the glass capillary mandrel 1384 through the conduit 1382 provides a channel 1388 within the collagen matrix. Flow of a perfusate medium 1394 proceeds into the fluid inlet port 1354 through conduit 1382 to the channel 1388 across the matrix chamber 1390 and to a second priming chamber 1378 to the outlet port 1392 and to a waste reservoir 1396. More than one channel may be present in alternate example CPDs.

Referring now to FIG. 13C to FIG. 13E, the seeding of the CPD is schematically depicted. In FIG. 13C a top view of the alternate CPD 1350 is schematically depicted. Note the orientation is opposite of that in FIG. 13B. The CPD 1350 is shown with the mandrel 1384 within the matrix chamber 1390 that can be filled with collagen. The CPD contains a silicone layer 1366 that is sealed with oxygen plasma between two glass slides 1370/1374. Referring now to FIG. 13D collagen 1391 or equivalent matrix is injected into the matrix chamber 1390 and allowed to gel around the mandrel 1384. The mandrel is removed through conduit 1382 leaving a channel 1388. Cells 1 (e.g. HUVECS and other cell types) are seeded at high-density in a perfusate medium 1394. Cells may be injected by a suitable means for example by a syringe.

The perfusate flow is maintained by means of a pump or equivalent device which moves the cells 1 into the channel 1388 where flow is stopped briefly for about 45 minutes allowing the cells to adhere to the channel wall. Growth by means of an incubator or equivalent device leads to the formation of a sprouting parent vessel within the channel (not depicted). Referring now to FIG. 13E the CPD 1350 is shown configured once perfusion is resumed through the cells 1 forming the parent vessel. Here, the inlet port 1354 is shown at the bottom on the same side of the CPD as the outlet port 1396, which facilitates handling of the device, but the location as seen on the right in FIG. 13C and FIG. 13D is also similarly functional. The incubator means further allows for growing the sprouting microvessels until the microvessels have formed networks.

Figure 14A:
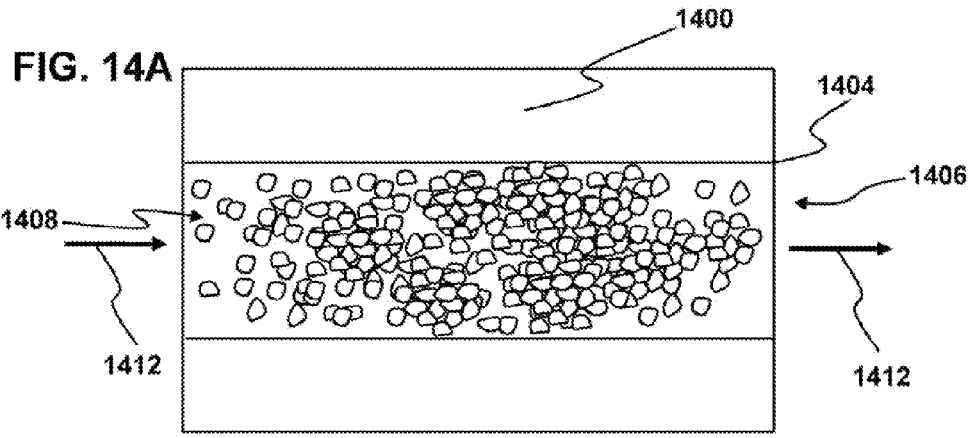
FIG. 14A schematically shows an example of a channel within a matrix seeded with human umbilical vein endothelial cells (HUVECs) at a high density.
Figure 14B:
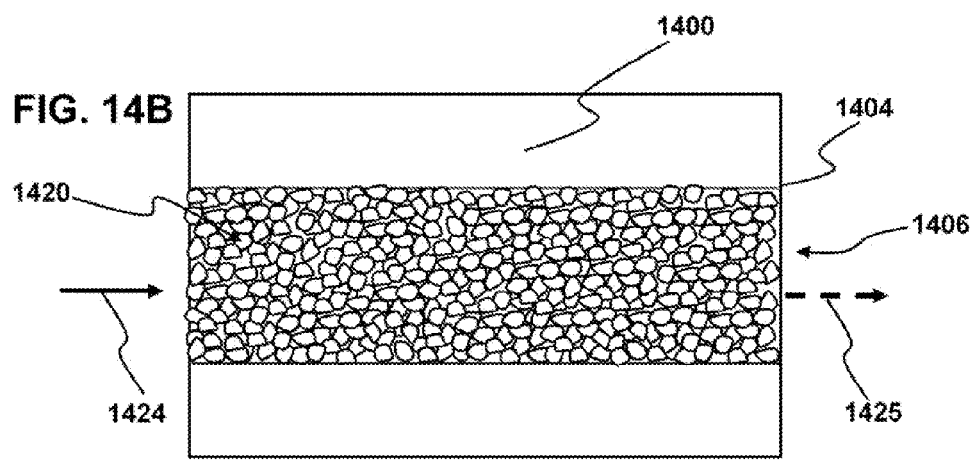
FIG. 14B schematically shows a channel within a matrix seeded with HUVECs where the cell density results in a plug within the channel.
Figure 14C:
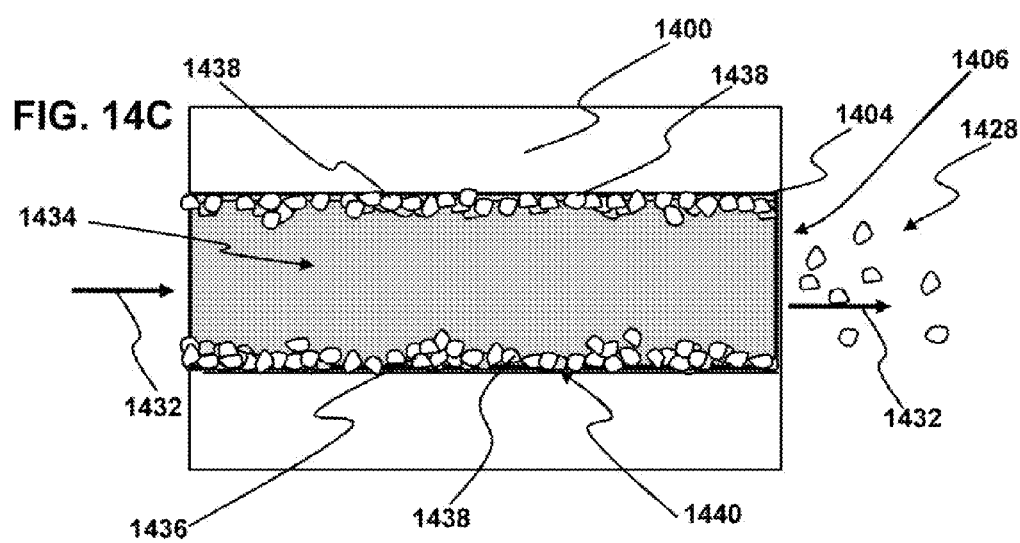
FIG. 14C schematically shows a channel after perfusion has removed non-adherent HUVECs.

The following examples were performed using a CPD (e.g. CPD 1350), equivalent device, or are schematically shown. Referring now jointly to FIG. 14A, FIG. 14B, and FIG. 14C, a high-density seeding method for a matrix channel is schematically shown. In FIG. 14A, an example of a collagen matrix is depicted 1400 together with a channel 1404. The channel diameter may be made to any desirable size for angiogenesis study or vessel growth. Cells, 1408, such as human umbilical vein endothelial cells (HUVECs), alone or mixed with other cell types (e.g. SMC, pericytes, fibroblasts, and precursors) are seeded at a high-density into the channel at a specified flow rate in a perfusate medium 1412. In some example embodiments endothelial cells or equivalents are present from a high-density minimum of about 250 cells to a maximum of about 2000 cells per sq. mm given a measured average cell size of about 18.0 microns diameter and systematic correction factor of about 2.5. The cells are thus highly concentrated and exhibiting reduced flow characteristics. The flow rate of the perfusate medium 1412 is set from a syringe pump or equivalent device and can be adjusted to provide a specific flow rate and pressure for a given channel. In certain embodiments a flow rate of 2 microliter/min is used which corresponds to a shear stress of 1.2 dyn/cm$^2$. Shear stress values of 0.75 to 30 dyn/cm$^2$ have been reported as physiological and represent additional embodiments. In other embodiments the flow rate could also be adjusted to create shear stresses outside the normal limits for creating pathological conditions.

In FIG. 14B, for some example embodiments the concentration is sufficiently high that flow of the cells within the channel is significantly reduced or stopped as a naturally occurring plug 1420 at the given flow rate 1424. In many cases the plug of cells is temporary and resolves without an increase in flow rate or pressure. In other cases the flow rate and pressure may be increased to remove the plug of cells. In certain examples the flow of cells stopped in the plug 1420 for about one or two seconds and then resumed 1425 without adjusting flow rate from the pump. In other examples the flow rate was increased slightly just before or after a plug of cells formed. In representative embodiments the flow was then discontinued by switching off the pump for about 30 to about 45 minutes allowing cells to adhere to the channel wall. It is recognized that the concentration of cells, when seeded at a high-density, is sufficiently high that flow of the cells reduces.

Also, evident is that physical stresses act on cells from the perfusate flow and pressure as well as from contacts between cells and from contacts between cells and the channel wall. These physical forces act as stimuli and stress on the cells and are particularly evident when a plug of cells forms stopping flow briefly. The aggregate physical stimuli can be altered, increased or decreased, based on changes in the cell concentration, pressure, and flow rate. Though it is believed the sprouting phenotype in vitro is mediated via a mechanism related to the high-density of seeding, in some cases the viscosity of the perfusate medium could be increased to impart further physical stress effects. Such, aggregate stimuli is believed to contribute to or initiate cellular events that mediate the activation of the sprouting phenotype. Also, perfusion pressure appears to affect growth rate and sprout maturation over time. It should be noted that sprouting in vivo is not dependent on a seeding density or cells being in a spherical shape. Sprouting in vivo does happen from flattened cells and is not dependent on cell density. The right set of angiogenic factors, ECM, and perfusate would be expected to stimulate normal flat endothelial cells or equivalents to sprout in our in vitro model similarly to what is observed in vivo.

Referring now to FIG. 14C, a side view through the channel is depicted. After the incubation to allow cells to adhere to the channel wall 1404 the flow rate of the perfusate medium is increased 1432 to about 2 microliters per minute clearing cells from the channel 1428 that were are not adherent to the channel wall 1404. After clearing, the channel wall 1404 is lined with a layer of cells. The majority of cells is confluent and is in contact with other cells and the matrix. For illustration purposes the schematic view through the side of the channel depicts cells lining the far side shown as grey shading 1434, whereas those cells on the top and bottom of the channel are depicted schematically outlined in black 1436, 1438. In some regions cells may be two or more layers thick 1436, but the most cells are present as single layers 1438. In some cases cells may not be in contact with other cells 1440, initially being subconfluent until later proliferation forms the parent vessel.

Figure 15A:
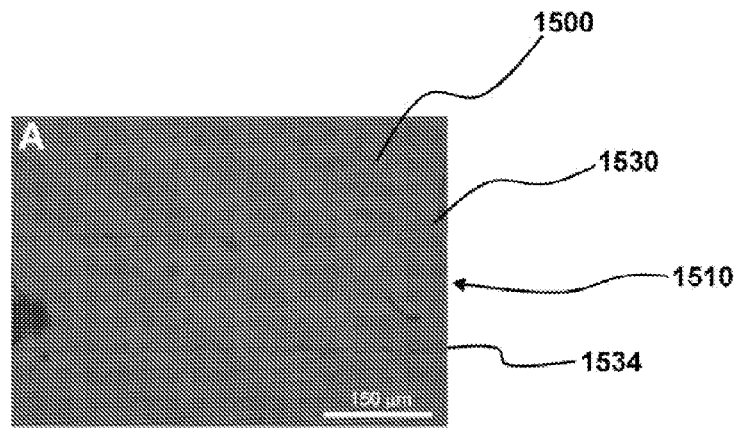
FIG. 15A shows an empty channel in a collagen matrix.

Referring now to FIG. 15A, an example of a collagen matrix 1500 with a representative channel 1510 of about 150 µm diameter is depicted with a top 1530 and bottom wall 1534. This channel 1510 was seeded at a high-density with HUVECs as described in FIG. 14A-C. The collagen matrix was formed with about 3 mg/ml final concentration. Higher or lower concentrations of collagen or equivalent may be used in alternate embodiments. In some examples alternate or hybrid matrix compositions may be used.

Figure 15B:
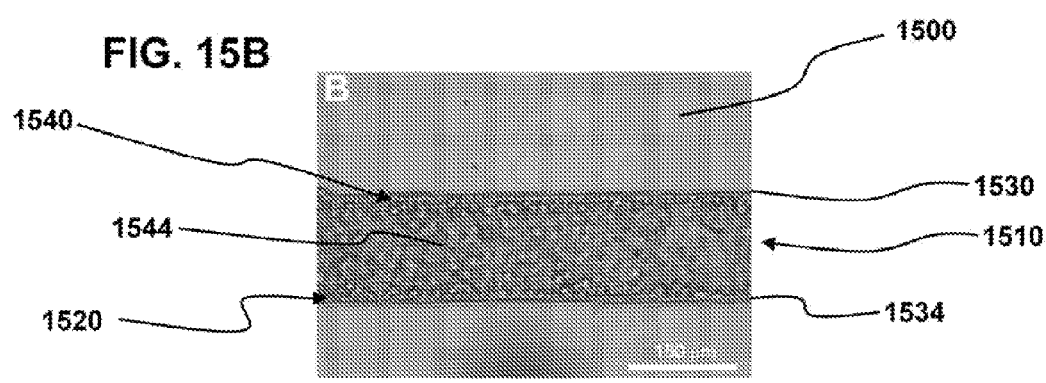
FIG. 15B shows the channel in FIG. 15A, with adherent cells after seeding at high density.

Referring now to FIG. 15B, the same matrix 1500 and channel 1510 are shown seeded with adherent human umbilical vein endothelial cells 1520, 1540, 1544 (HUVECs). In this example the cells were seeded at where cells appear to be maximally packed into the channel at about 1000 to 2000 cells per Sq. mm channel.

During seeding the perfusate flow stopped naturally forming a plug for about one second that resolved without changing the flow rate with perfusion continuing. The pump was at this point turned off stopping perfusion for about 30-45 minutes, allowing the cells to adhere to the cell channel wall and then subjected to ongoing perfusion. Subsequently, the pump was turned on at the rate of 2 microliters/min which was used to clear away non-adherent cells resulting in the channel lined with cells, either one 1520 or two or more 1540 layers deep. In some cases a higher perfusate flow setting could be used if necessary to facilitate flow and clearing of cells. Cells on the top 1540 or bottom 1520 are in focus and appear more retractile. The cells visible in the central portion 1544 are somewhat out of focus representing adherent cells on the near and far sides of the channel.

Figure 15C:
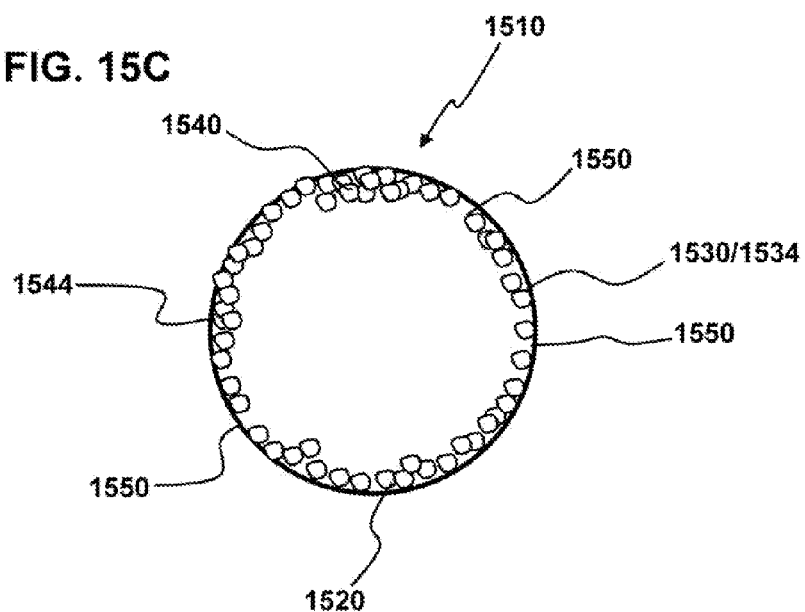
FIG. 15C schematically depicts a cross section of seeded channel shown in FIG. 15B.

In FIG. 15C, the channel 1510 from FIG. 15B, is depicted schematically (end view into channel). This represents the channel after unbound cells have been washed out. The majority of cells 1520, 1540, 1544 are in direct contact with each other or with the channel wall 1530/1534, forming a confluent sleeve of cells that are in most cases one layer thick. Some regions may include two or more layers of cells 1540. In some cases regions may be present where cells are nearly in contact with other cells and are subconfluent 1550. Subsequent cellular proliferation will typically cover these regions as the parent vessel grows.

Figure 16:
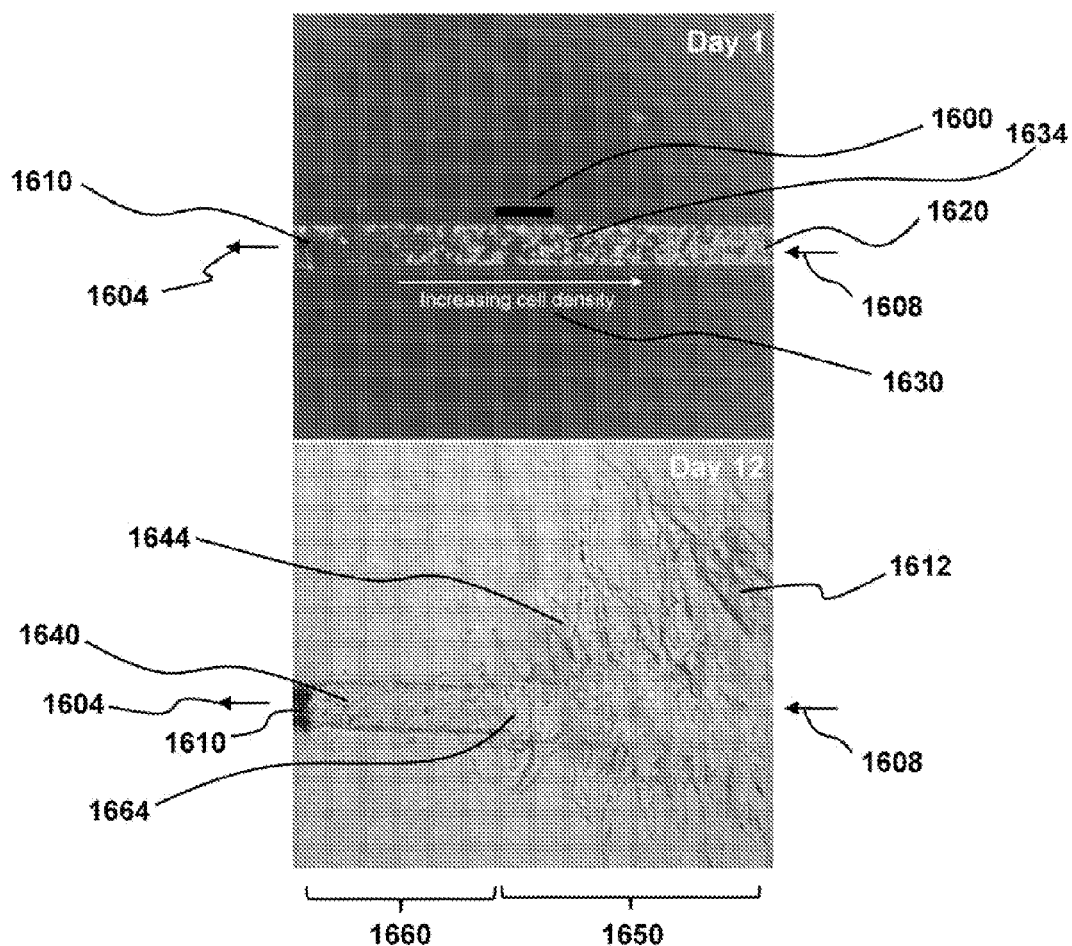
FIG. 16 shows a matrix channel immediately after seeding of endothelial cells in high density gradient at Day 1 (top panel). Also shown is the same channel after 12 days of perfusion (bottom panel). The induction of sprouting related to cell density is apparent (bottom panel).

Referring now to FIG. 16, an example of the activation of sprouting competency for cells (HUVECs) is shown. The top panel shows a channel 1610 within a collagen matrix that has been seeded with a plurality of cells 1620 in a cellular density gradient 1630. The cellular gradient was created by stopping the influx of cells prematurely, thus there was less cell coverage per volume of channel at the upstream end of the channel 1604 and more concentrated cells in the downstream end 1608. The cells were allowed to adhere for about 45 minutes and then were subjected to perfusion. Parent vessels within intact lumens typically form quickly, within minutes, and appear to form almost instantaneously when cells are seeded at high-density concentrations. A complete monolayer is then formed when the cells attach and stretch out, usually occurring in about 30-60 minutes. When a lower cell concentration is used, it takes longer for a complete monolayer to form.

Sprouting of microvessels from parent vessels also depends on the density of seeding. In high-density seeded parent vessels, the first minuscule sprouts seen as merely cellular protrusions are visible after a few hours. Larger sprouts usually develop during the first 2-3 days after seeding.

The center 1600 of the cellular density gradient is where the dramatic sprouting phenotype is first activated and observable. It can be seen in the top panel at day 1 of growth the majority but not all of the cells 1634 are in contact with neighboring cells in the 3D space within the channel. Cells 1620 are also in contact with the channel wall.

The lower panel shows a parent vessel 1640 after 12 days of growth with perfusion in the same channel 1610. The beginning of dramatic sprouting of microvessels is observed from the middle region 1644 of the parent vessel. This region corresponds to the cellular density indicated by the bar 1600 in the top panel. Even more dramatic sprouting is observed more upstream 1612, whereas the downstream end of the parent vessel corresponding to lower density of cells shows no sprouting 1660. Sprouting of microvessels continues and proliferation increases as the density of cellular seeding increases 1650. The demarcation between the quiescent domain and sprouting domain 1664 is clear and striking correlating with seeding density. In most cases low density seeding resulted in quiescent parent vessel's that do not proliferate and sprout microvessels. This observation suggests that a threshold density of seeding triggers the phenotype.

Estimation of the cellular density that triggers activation of the cells was addressed further in quantitative experiments (e,g. see FIG. 20A-F and FIG. 21A-B).

It is possible cells seeded below this density may retain some reduced capacity to sprout as microvessels. In addition to the cell-cell contact trigger the composition of the perfusate also is believed impart competency for sprouting. Growth factors present in the perfusate medium may act synergistically with cellular contact signaling to mediate the phenotype. Additionally, the cell matrix contacts s also may contribute to the phenotype. Further, the physical forces from perfusate flow, pressure, and stress from plug formation may also contribute to the activation of the sprouting competency in cells. However, the cell-cell contact trigger appears to contribute significantly to the activation of the sprouting competence phenotype.

Figure 17:
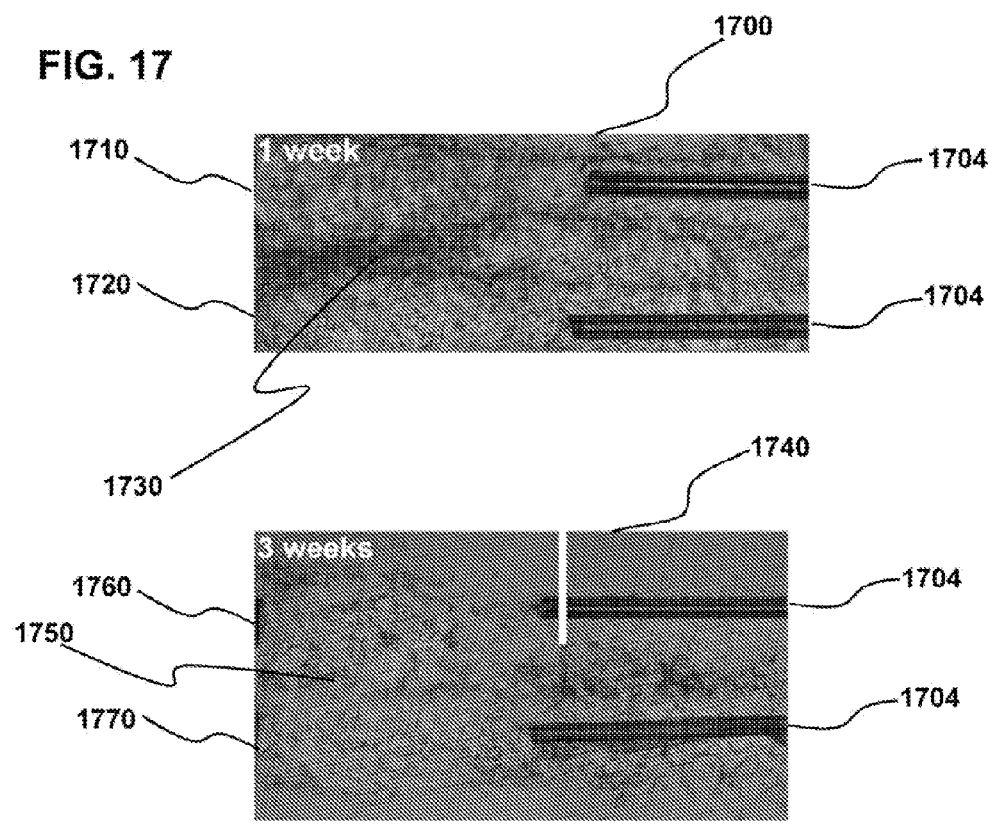
FIG. 17 shows examples of two sprouting competent parent vessels that have been grown for one week and three weeks undergoing anastomosis to form complex microvessel networks.

Referring now to FIG. 17, shown are examples of two sets of tandem parent vessels derived from high-density seeding that are undergoing anastomosis to form complex 3D microvessel networks. Individual CPD's were incubated with perfusion over time and processed at time points with the longest ending at 5 weeks. In most experiments channels were about 500 microns apart, but additional configurations were also examined. The maximal distance between channels that microvessels can traverse has not been determined. However, microvessels should be capable of growing towards the other parent vessels from over 500 microns to about several millimeters.

Depicted are parent vessels 1710, 1720 growing from conduit 1704, after one week 1700 and three weeks 1740. After the one week of growth 1700 the first vessel 1710 and second vessel 1720 are observed expanding in diameter with their associated microvessels 1730 sprouting to form the microvessel network between the two vessels. In a similar assay 1740, after 3 weeks the microvessel network 1750 is merged via anastomosis and remains viable and capable of perfusion. The parent vessels 1760, 1770 can be seen, but are almost completely merged into the microvessel network. In some examples the microvessel network merged to such an extent that a cavity formed, however the network was still capable of being perfused through the microvessels.

The incubation time required until the microvessel networks merge via anastomosis is dependent on the original placement and distance between the channels. Perfusion of tandem parent vessels resulted in the formation of sprouting and complex 3D microvessel networks. Sprouting microvessels grew in all 3D from the parent vessels. If parent vessels were originally close together the sprouting microvessel networks usually anastomose into a larger merged microvessel network that remained viable and competent for perfusion.

Periods of up to five weeks with ongoing continuous perfusion have been examined. A majority of cells throughout the parent vessels and complex and extended microvessel networks remain viable as assayed with Live/Dead fluorescence viability staining. Useful stains such as Live/Dead are commercially available from, for example, Invitrogen Corp. of Carlsbad Calif. Overall, sprouting does slow over time likely reflecting limits on in vitro cultivation of the HUVEC primary cell cultures.

Sprouting microvessels likely grow and also regress depending on nutrients, cellular signals, and culture conditions (e.g. presence or absence of serum and specific growth factors). The stability of newly formed microvessels and maturation into more mature vessels can be assessed by methods of this disclosure using endothelial cells and additional cells types. Composite microvessels comprising endothelial cells have been shown to be stabilized by culture conditions and the presence of support cells. For example growth factors such as VEGF, IGF-1 with serum free conditions have been shown to promote angiogenesis and increased short term stability of capillary-like networks in vitro (French, Lindemann et al. 2001). Similarly, it has been shown that addition of perivascular cells such as pericytes and smooth muscle cells can stabilize such newly formed capillaries and aid their maturation (Frerich, Lindemann et al. 2001). It is feasible addition of additional cell types such as endothelial (vascular) progenitor cells or stem cells coupled to defined culture condition in perfusates could also aid the stability and maturation of composite microvessels.

Figure 18:
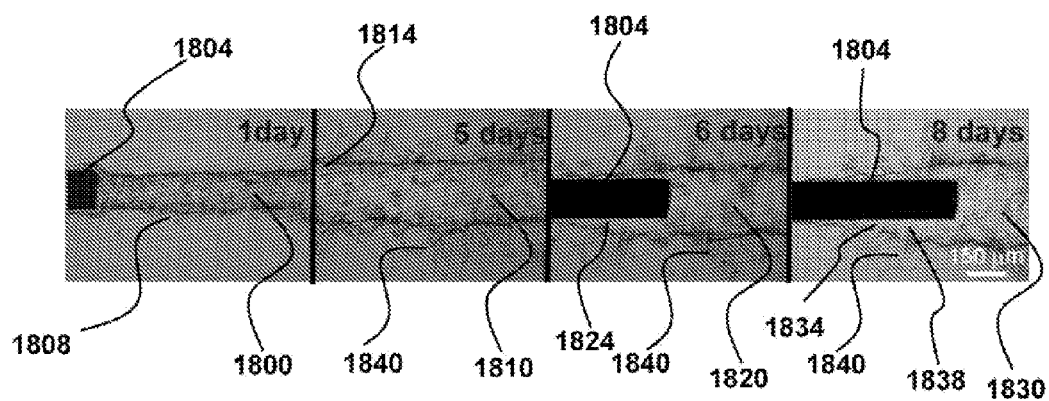
FIG. 18 shows the growth of parent vessels and associated sprouting of microvessels from one to eight days.

Referring now to FIG. 18, parent vessels grown after one to eight days of luminal perfusion are shown in several adjacent panels to illustrate additional growth characteristics. Each CPD used to grow parent vessels was handled similarly and processed for imaging of each parent vessel 1800, 1810, 1820, and 1830, at the indicated day. Each parent vessel is perfused from conduit 1804 visible in some of the panels. The first panel after day one of perfusion shows the parent vessel 1800 with only nascent sprouting of microvessels 1808. In the next panel after day five of perfusion the vessel 1810 shows robust sprouting of microvessels 1840. The visible increase in diameter of the parent vessel 1814 is also evident. In the next panel by day six of perfusion the parent vessel 1820 appears to have reached an increase of about twice the original 150 micron diameter. It appears proliferation of cells of the parent vessel encompasses the conduit 1804 growing over the ends 1824. The final panel after eight days of perfusion shows that the parent vessel 1830 continues the sprouting of microvessels 1840 and has continued to increase slightly in diameter. Also the growth of the vessel over the end of the conduit 1804 is evident 1834.

The expansion in diameter of each parent vessel is believed to be both from invasion and growth of cells within the collagen matrix and from responses of the vessel to the pressure of the perfusion flow. The degree of cellular proliferation and sprouting was observed to be continuous over time but did slow somewhat after several weeks of incubation. The slowing of growth and sprouting may be due to the limited lifespan of HUVECs in vitro.

Referring to FIG. 19, shown are confocal 3D reconstruction images from a representative microvessel network. The microvessels networks 1900 were grown using the high-density seeding methods described previously. The sprouting microvessels were labeled with rhodamine labeled wheat germ agglutinin to visualize the membrane structure of endothelial cells in the microvessels and with the fluorescent DNA stain 4',6-diamidino-2-phenylindole (DAPI) to show nuclei.

In panel A, the microvessels 1910 are seen to be branched with intact with unobstructed patent lumens based on the 3D tube structures and perfusion. In panel, B, a higher magnification of microvessels 1920 is depicted with an intact tubular vessel structure. The nuclei 1930 of individual endothelial cells are also shown for this sample. Branches from the microvessel are evident 1940 that are intact with unobstructed patent lumens with nuclei. The structure of the microvessels is consistent with viability as assessed by staining and capacity for perfusion.

Quantitative Analysis of Sprouting

Referring, now jointly to FIG. 20A-FIG. 20F and FIG. 21A-FIG. 21B, a series of assays were done to with quantitative image analysis to determine the minimal and maximum seeding density that triggers the sprouting competency phenotype as well as aspects of sprout growth. Endothelial cells were seeded as described previously in a CPD1350 and incubated to form sprouting parent vessels. Samples were examined at time points after seeding measured in hours (h) to examine both shorter term and longer term incubation effects on sprouting. Growth of sprouting parent microvessels was analyzed for incubation experiments from up to 96 h with data analyzed at 0, 24 h, 48 h, 72 h and 96 hours (h) post seeding. The minimum and maximum cell seeding densities that provided sprouting were determined together with measurements of the average sprout length along the parent microvessel position.

Cell seeding density measurements were performed by analyzing the video image data for mean greyscale value (GSV) along the length of the vessel. The images analyzed were acquired using transmission dark field microscopy with a 4×0.10 NA objective lens. A region of interest (ROI) of 100 pixels wide was selected every 100 pixels along the length of the vessel to sample the mean GSV within each box. To compensate for uneven background illumination, another similar set of ROIs was used to sample the background surrounding the vessel. The background corrected mean GSV was plotted versus position along the vessel. To calculate cell seeding density, the relationship between number of cells and mean greyscale value within a given ROI was established. The relationship between cell seeding and GSV was found to be approximately linear within the range of cell counts measured (data not shown). The slope of the best fit line was used in calculations to relate mean GSV to cell seeding density.

Referring now to FIG. 20A, the plot of the initial cell seeding density versus position along the parent vessel is depicted 2000. The minimum cell seeding density was established by plotting sprout length versus cell seeding density, where the sprout length equals zero for the best fit lines of this plot, this is the true minimum cell seeding density. These values are 362 cells per sq. mm for 24 h, 340 cells per sq. mm, for 48 h, 317 cells per sq. mm, 293 cells per sq. mm, 96 h. The minimum actual seeding experiments for cell seeding density will always be larger than the values quoted above (e.g. 293 cells/sq. mm for 96 h) and plotted in FIG. 21B.

Referring now jointly to FIG. 20B to FIG. 20F, the microscope images of sprouting parent microvessels from the short term growth experiments summarized in FIG. 20A (above). In FIG. 20B the initial cell seeding 2008 with an overlay of the cell seeding density 2012 is shown. In FIG. 20C sprouting parent microvessels after 24 h incubation after seeding is shown 2016. Representative sprouts are shown in the middle portion of the parent microvessel 2018. A viable sprout for the lowest density region is indicated by the white line 2020. The same parent vessels are shown after 24 h 2024, 72 h 2032, and 96 h 2040. The minimum initial seeding density where a viable sprout was found is also shown by white lines for each 2028 (48 h), 2036 (72 h), 2044 (96 h). The overall sprout length increases with time as seen by representative sprouts from the middle of each parent microvessel 2026 (48 h), 2034 (72 h), 2042 (96 h). In FIG. 20F an air bubble is visible just to the left of the white line 2044 for the minimum density for a viable sprout. It can be seen that sprouting is fairly uniform over the domain where sprouting is evident.

The data from experiments for short term growth experiments established the minimal seeding density required for sprouting. The minimum value for sprouting was about 250 attached cells per sq. mm. This minimum can be compared to the peak measured value of about 1000 to 2000 cells per sq. mm, where the cells appear visually to be maximally packed within the conduit or channel during seeding. The measured 1000 to 2000 cells per sq. mm agrees with theoretical maximum values.

Referring now to FIG. 21A and FIG. 21B, the average sprout length was also determined for the growth of parent vessels from 0 to 96 h. In FIG. 21A the sprout length 2100 is shown for 24 h, 2116, 48 h, 2108, 72 h, 2112, and 96 h, 2116. The sprout length agrees reasonably well with direct measurements from the microscope images.

Referring, now to FIG. 21B, a graph of the average sprout length versus the initial seeding density is show 2120. The best fit line for each time point analyzed is also shown 24 h, 2124, 48 h, 2128, 72 h, 2132, and 96 h, 2136. The minimum cell density data can be found from where the best fit line intersects the x-axis, the initial seeding density (number of Cells per sq. mm). An expanded view would show the intersections to be the values of 362 cells per sq. mm for 24 h, 340 cells per sq. mm, for 48 h, 317 cells per sq. mm, 293 cells per sq. mm, 96 h.

It should be noted there may be a misleading factor regarding measurement of sprout length. As the inner diameter of a microvessel gets larger this has not been taken into account in the current analysis. Thus, any changes in diameter are included in the sprout length values.

Figure 22:
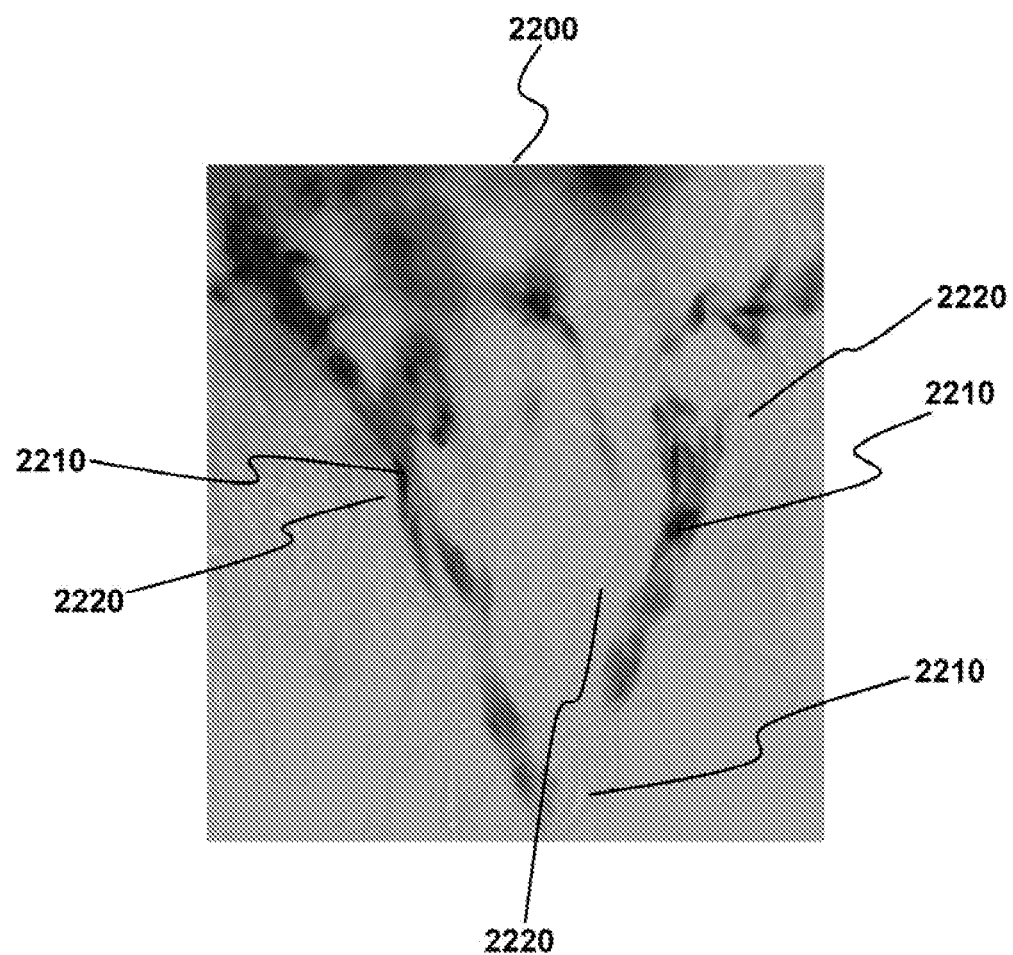
FIG. 22 shows an image of a composite sprout with human umbilical endothelial cells (HUVECs) stained with cell tracker green (dark) and rat smooth muscle cells as retractile (clear/light) surrounding the HUVECs in a perivascular location.

Referring now to FIG. 22, composite parent vessels consisting of HUVECs and rat aortic smooth muscle cells (RASMCs) were examined. The HUVECs were labeled with fluorescent dye (Cell Tracker Green) and seeded at high densities and with methods described above in this disclosure where the increased sprouting phenotype was evident. After, growth for about 24 h, the HUVECs formed sprouting parent vessels which were subjected to ongoing perfusion with a growth medium. RASMCs were seeded into the HUVEC parent vessels and were observed to adhere to the microvessel wall and subsequently to migrate through the microvessel wall assuming a perivascular position. In FIG. 22 an overlay of fluorescent and bright field images is shown 2200 of representative composite HUVEC and RASMC sprouting parent microvessels. The parent microvessels are seen with dark staining 2210, while perivascular RASMCs appear clear 2220. The migration of the RASMCs to the perivascular position around the HUVEC parent microvessels is consistent with their known support role in vessel maturation and stability.

Assays and Targets for Angiogenesis Research

The ability to dramatically activate HUVECs for a sprouting competent phenotype provides for increased ability to screen for products that are angiogenic or that are angiostatic within the perfusate, matrix, or that are derived from normal, pathogenic (e.g. cancerous, virally infected), or engineered cells and tissues. Monitoring the microvessel networks provides an efficient measure where increased sprouting and microvessel growth indicates an angiogenic effect and reduced sprouting and microvessel growth indicates an angiostatic effect. Also the contribution of endothelial cells, smooth muscle cells, pericytes, and fibroblasts together with progenitor cells and stem cells can be assayed for additional aspects of vessel formation and function. Also, cancer cells can be tested for their angiogenic potential by having them suspended in the matrix. Development and growth of complex tissues can be better examined with improved vascularization now available. The robust increase in sprouting of microvessels provides a sensitive assay system.

The hypothesis that cell-cell mediated signaling is primarily responsible for the activation of the sprouting phenotype can be tested by examining candidate genes and their gene products known to facilitate cellular signaling in homophilic endothelial cell adhesion. The contribution of cell-matrix mediated signaling, growth factor-cell mediated signaling, and mechanical sensing mediated signaling related to flow of perfusate can also be addressed to determine the overall cellular phenotype and behavior in vessel formation. Further, the promise of the ability to regulate the activation of the sprouting phenotype provides even additional benefits for angiogenesis models and research.

Endothelial Specific Markers

Target genes in endothelial cells can be genetically modified via recombinant DNA methods to examine their contribution to cellular phenotypes including but not limited to the activation of the sprouting competency phenotype. Specific marker genes expressed in endothelial cells are attractive targets for manipulation and testing in assays using methods of this disclosure. Endothelium derived cell lines can also be examined such as those derived from macrovessels and from microvessels. Endothelial cells display significant heterogeneity in vivo (Aird 2007). Numerous genes preferentially expressed in either arterial endothelium or venous endothelium have been identified. Arterial endothelial cells have been shown to specifically express several genes including ephrinB2 (Gale, Baluk et al. 2001), Delta-like 4 (Dll4) (Krebs, Xue et al. 2000), activin-receptor-like kinase (Alk1) (Seki, Yun et al. 2003), endothelial PAS domain protein (EPAS1) (Tian, McKnight et al. 1997), Hey1 (Nakagawa, Nakagawa et al. 1999), Hey2 (Nakagawa, Nakagawa et al. 1999), neuropilin 1 (NRP1) (Mukouyama, Gerber et al. 2005), and decidual protein induced by progesterone (Depp) (Shin and Anderson 2005). Venous endothelial cells have been shown to specifically express several genes including EphB4 (Gerety, Wang et al. 1999), neurophilin 2 (NRP2) (Yuan, Moyon et al. 2002), COUP-TFII (You, Lin et al. 2005), and class III β-tubulin at the tip of venous valves (Kang and Lee 2006).

Each of these known genes could be obtained and genetically engineered to assay the effect of over expression, gene dosage, mutations, or loss of function, on endothelial cell function in angiogenesis using methods presented in this disclosure. Sequence data is available for each of these genes from the NIH Genbank genetic sequence database facilitating such analysis. Genbank is an annotated collection of all publicly available DNA sequences (Benson, Karsch-Mizrachi et al. 2008).

Endothelial Cell Lines

Assaying subpopulations of endothelial cells from particular sources or established endothelial derived cell lines provides for advances in understanding angiogenesis and in regulating growth of vessels. For example, endothelial cell lines derived from either arterial macro or micro vessel sources could be selected to form microvessels using CPDs and methods of this disclosure. Candidate cell lines with extended lifespan or that are immortalized could additionally be characterized for normal karyotypes and non-tumorgenic phenotypes as well as expression patterns of adhesive proteins and coagulation molecules (Bouis, Hospers et al. 2001). Endothelial cell lines made from human umbilical vein (HUVEC) that have extended lifespan, are characterized to varying degrees, but that are not immortalized, exist including ESV233, ESVSF108, ESV2010 (INS/EGF), ESV2010-GF (Hohenwarter, Jakoubek et al. 1994). Several immortalized endothelial cells lines exist that are well characterized including macro vessel derived line EA.hy926 (Edgell, McDonald et al. 1983), macrovessel derived line EV304 (Takahashi, Sawasaki et al. 1990), and microvessel derived line HMEC-1 (Ades, Candal et al. 1992). Additionally, cell lines exist and new lines could also be generated for study.

Endothelial cell lines with extended lifespan or that are immortalized could be assayed for function in forming vessels and in angiogenesis using methods presented in this disclosure. Use of candidate endothelial lines offers the practical advantage of their extended life span in vitro, reported stable karyotype, and associated phenotypes. Additionally, such cell lines could be further genetically modified or engineered to exploit their existing cellular phenotypes. Also, endothelial cells can be isolated from patients to test how they respond to certain drugs using personalized medicine approaches with methods of this disclosure. The same is true for cancer cells.

Additionally, similar cells and cells line derived from lymphatic tissue could be utilized in methods of this disclosure.

Cellular Adhesion and Signaling Pathways

The activated sprouting phenotype induces proliferation of microvessels sprouting from the parent vessels. This phenotype is likely related to cellular responses to proliferative signals. During angiogenesis capillary sprouts grow from larger vessels that contain contact inhibited cells. Genes and their protein products from adhesion and signaling pathways associated with contact inhibition are candidates to be assayed via methods of this disclosure to gain insights into vessel formation and angiogenesis.

The activation of the sprouting competency observed with HUVECs is dependent of the seeding density probably from cell-cell contacts. Contributions from cell-matrix-contact, as well as cell-growth factor contacts and even mechanical signaling from seeding and perfusate flow are also potentially involved in activating the sprouting competency. All of these stimuli sources implicate signaling and may be integrated to mediate the overall cellular phenotype and behavior.

Adherens junctions play important roles between endothelial cells for contact inhibition of cellular growth and paracellular permeability to circulating solutes and leukocytes. Tight junctions are also involved in cellular adhesion and are responsible for regulating barrier functions and polarity (Wheelock and Johnson 2003; Bazzoni and Dejana 2004). Additionally, other adhesion proteins, such as the platelet endothelial cell adhesion molecule, PECAM-1, found at endothelial intercellular junctions, are involved in cellular adhesion and cellular signaling.

Endothelial cells form unique cell-cell adherens junctions containing an endothelial specific cadherin, VE-cadherin. Endothelial cells also express N-cadherin, T-cadherin, and a related protein named VE-cadheren-2. VE-cadherin and the other cadherins expressed in endothelial cells transfer information intracellularly through interactions with a complex network of cytoskeleton proteins and signaling molecules. VE-cadherin forms complexes with β-catenin, plakoglobin, and p120 catenin and likely contacts the actin cytoskeleton in structures that are similar to typical adherens junctions. The formation of endothelial adherens junctions, maintenance, and disassembly are important points of regulation for vessel formation and function.

Signaling pathways associated with endothelial adherens junctions include the wnt pathway, Rho GTPases and signaling through receptor tyrosine kinases and are candidates for further study of the activation of the sprouting competency phenotype. It follows that genes and protein products from these signaling pathways in addition to adherens junctions components VE-cadherin, N-cadherin, T-cadherin, and VE-cadheren-2, as well as the interacting proteins of VE-cadherin β-catenin, plakoglobin, and p120 catenin, as well as PECAM-1, are candidates for manipulation and for assaying in the microvessel network assay of this disclosure. Further, downstream events that are unknown could be elucidated using the microvessel assays and methods of this disclosure.

Components of tight junctions are also known and include transmembrane adhesive proteins, intracellular molecules, and signaling pathways. Occludin, claudins (e.g. claudin 1 and 2, and other claudin family members), junctional adhesion molecules (e.g. JAM-A, JAM-B, JAMC) are involved in tight junction adhesive functions. Intracellular components of tight junctions include membrane-associated guanylate kinases family members (MAGUK) including ZO-1, and related ZO-2, and ZO-3, along with non-MAGUK proteins of AF-6/afadin, Par-3/ASIP, and MUPP-1 (Bazzoni and Dejana 2004). Manipulation of tight junction components may yield important information about the activation of sprouting competency and aid in determining barrier function of such vessels. Also, downstream events that are unknown could be elucidated using the microvessel assays and methods of this disclosure.

Each of the known genes of adherens junctions and tight junctions or associated signaling components could be isolated without undue effort and genetically engineered to assay the effect of over expression, gene dosage, mutations, or loss of function on endothelial cell function in angiogenesis using methods presented in this disclosure. Sequence data is available for each of these genes from the NIH Genbank genetic sequence database facilitating such analysis.

Morphogenesis of Endothelial Cells in Angiogenesis and Vasculogenesis

Endothelial cell morphogenesis includes angiogenesis, where vessels form from existing vessels, as well as vasculogenesis, where vessels form from endothelial cells (EC) or EC precursors and progenitor cells in tissues or from delivery via circulation. Endothelial cell morphogenesis also includes cases where microvessels regress based on signaling input and regulation.

The activated sprouting phenotype induces proliferation of microvessels sprouting from the parent vessels. This phenotype is also likely related to endothelial cell morphogenesis from contacts between endothelial cells and also from contacts between endothelial cells and the extra cellular matrix (ECM). Endothelial cell morphogenesis in forming new vessels has been shown to be affected by the matrix-integrin-cytoskeletal (MIC) signaling pathway (Review, Davis, Bayless et al. 2002).

This MIC pathway starts with interactions between cells via cell-cell junctional contacts and from interactions between cells and the extracellular matrix components. Involvement of integrins (e.g. α2β1, α1β1, αvβ3, α5β1, α6β1) and extracellular matrix interactions, participation of cytoskeletal elements (e.g. actin, microtubule, and intermediate filament cytoskeletons) and downstream signaling and regulatory molecules (e.g. Rho GTPases, Rho A, Rac1, Cdc42, PAK-1, lateral inhibitory factors, ECM degrading proteinases) all contribute to the ability of endothelial cells to form tube structures, sprout, and branch as new microvessels during morphogenesis.

Membrane-type matrix metalloproteinases (MT-MMPs) that degrade ECM are postulated to participate in endothelial cell morphogenesis (Hiraoka, Allen et al. 1998); (Notary, Allen et al. 2000). Candidates for study and manipulation are MMP-1, MMP-2, MMP-9, as well as other equivalent MT-MMPs (Davis, Bayless et al. 2002). Also, inhibitors that block MT-MMPs such as the protein TIMP-2, and the chemical MMP inhibitor GM6001 have been shown to block endothelial cell morphogenesis when endothelial cells are suspended in collagen (unpublished data, Davis, Bayless et al. 2002)). TIMP-2 inhibits endothelial cell proliferation and is a TIMP family member of natural metalloproteinase inhibitors. The chemical GM6001 is an inhibitor of collagenases and is available from Millipore.

Lateral inhibition is a phenomenon where subsets of cells produce factors that inhibit neighboring cells which can result in selective differentiation. Such inhibitory factors could play a role in endothelial sprout density (Davis, Bayless et al. 2002). For example, molecules shown to regulate lateral inhibition are the Notch ligands Jagged, and Delta (Lindsell, Boulter et al. 1996; Zimrin, Pepper et al. 1996; Bell, Mavila et al. 2001). Also, the Notch 1 and Notch4 receptor have been shown to be present in endothelial cells (Zimrin, Pepper et al. 1996; Uyttendaele, Closson et al. 2000; Lindner, Booth et al. 2001). These factors are candidates for study and manipulation to determine their overall role in endothelial morphogenesis.

Manipulation of MIC components and assay of individual products from the MIC and downstream pathways is feasible in methods of this disclosure. Many genes and gene products associated with MIC signaling and endothelial cell morphogenesis are known and could be assessed in the microvessel assay for contribution to sprouting competency and angiogenesis.

Known MIC pathway genes or associated signaling and regulatory components could be isolated without undue effort and genetically engineered to assay the effect of over expression, gene dosage, mutations, or loss of function on endothelial cell morphogenesis using methods presented in this disclosure. Sequence data is available for many of these genes from the NIH Genbank genetic sequence database facilitating such analysis.

Screening for Products Affecting Angiogenesis

Figure 23:
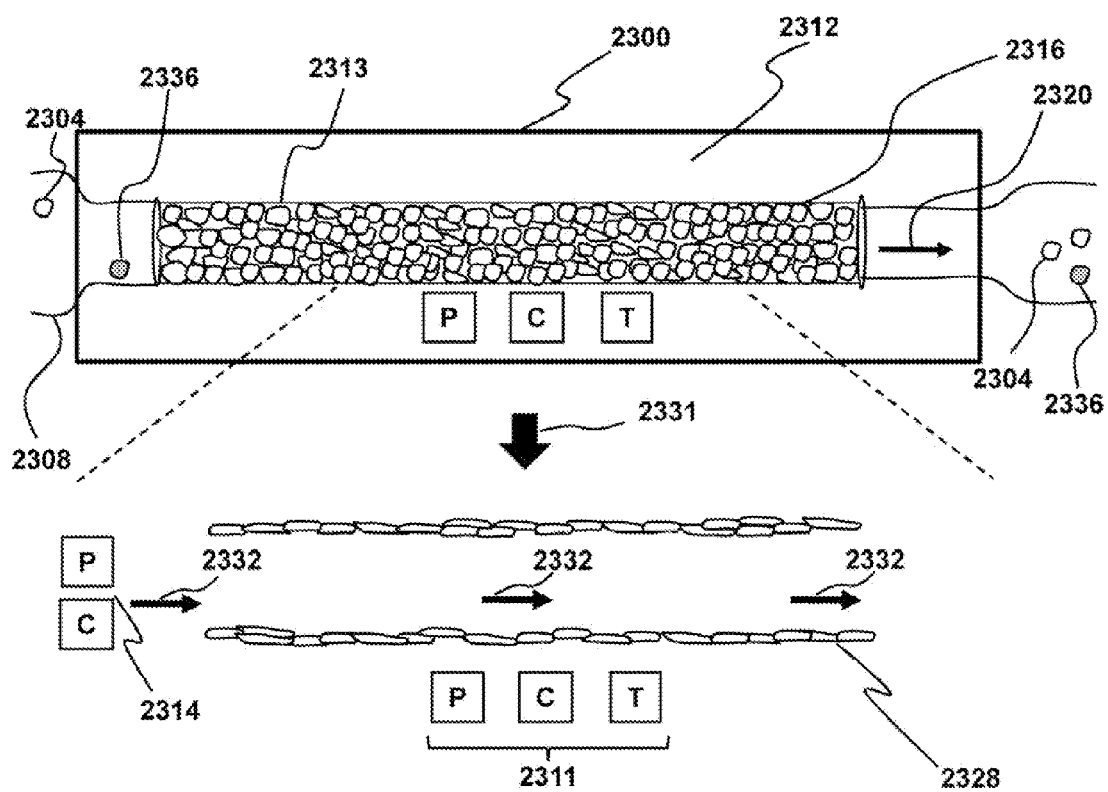
FIG. 23 schematically shows the seeding of cells into a matrix channel at a high-density and parent vessel formation for a microvessel sprouting assay.

Referring now to FIG. 23, shown schematically is an assay for screening for cells (C), products (P), and tissue (T) that affect parent vessels, microvessel sprouting, and microvessel network formation. Utilizing a CPD such as CPD 1350, CPD 900, or equivalent, and methods of high-density seeding to activate the sprouting competent phenotype, responses of microvessel sprouting as well as the formation of microvessel networks can be examined. The networks of microvessels can be used to screen for angiogenic and angiostatic factors in the matrix or perfusate medium by monitoring the formation of the microvessel network, where increased growth of the network indicates an angiogenic factor and decreased growth of the network indicates an angiostatic factor.

Candidates, including Cells, (C) products (P), and tissue (T) can be assayed either dispersed throughout the matrix, or locally concentrated. Alternately, cells (C) and products (P) can be added to the perfusate medium. In many embodiments bioactive products that may be released from the different candidates being assayed can be assessed. Bioactive means that the candidates affect growth of sprouting microvessels in some discernible manner, for example by providing for measurable differences in growth.

Cells can be endothelial cells, smooth muscle cells, pericytes, fibroblast cells, progenitor cells, stem cells, muscle cells, liver cells, lung cells, skin cells, epithelial cells, human cells, animal cells, plant cells, eukaryotic cells, genetically engineered cells, genetically modified cells, diseased cells, virally infected cells, and cancerous cells. Products can include growth factors (e.g. basic fibroblast growth factor (bFGF), vascular endothelial growth factor (VEGF), phorbol esters (e.g. phorbol 12-myristate-13-acetate (PMA)), platelet-derived growth factor (PDGF), connective-tissue growth factor (CTGF), heparin-binding growth factors (HB-EGF), interleukin-8 (IL-8), long $R^3$ insulin-like growth factor ($R^3$IGF-1), insulin like growth factors (e.g. IGF-1), human epidermal growth factor (hEGF), connective-tissue growth factor (CTGF), heparin-binding EGF like growth factor (HB-EGF), cytokines, angiopoietins, placental growth factor, various chemokines (e.g. SDF-1α), TGF-β, soluble mitogens, cellular adhesion proteins (e.g. fibronectin, vitronectin, fibrin, arginine-glycine-aspartate motif (RGD) proteins, RGD-peptides, gelatin, collagen, and different collagen subtypes), synthetic peptides, and equivalent bioactive compounds. Tissues can be healthy, cancerous, virally infected, or genetically modified or engineered.

At least one cell type 2304 can be seeded at a high-density 2313 through conduit 2308 into a channel 2316 within a matrix 2312 of a CPD 2300. The at least one cell type can be HUVECs, or combinations of cell types (e.g. SMC, pericytes, progenitor cells, stem cells) some of which are capable of being activated for competency for sprouting as microvessels from parent vessels 2328, via cell-cell, cell-matrix, cell-growth factor, and physical contacts from perfusate flow. Alternately, the cells 2336 can be genetically modified or engineered to release bioactive products. Incubating the seeded channels further allows the parent vessel to develop confluent cell layers 2331.

A first perfusate medium 2320 can remove cells 2304 that do not adhere to the channel matrix wall 2316 after about 45 minutes incubation. The incubation time can be much shorter or omitted, depending on the experimental conditions. The first perfusate medium 2320 or a second perfusate medium 2332 also provides for growth of the parent vessel 2328.

In different embodiments the perfusate mediums can be of the same composition or can be differently formulated as required. Cells (C), products (P) or tissue (T) 2311 can be seeded into the matrix 2312 at various locations either locally concentrated or dispersed. Alternately, cells (C) or products (P) 2314 added to the perfusate medium 2320, 2332. Products (P), for example angiogenic and angiostatic bioactive compounds, can also be secreted from cells of the parent vessel 2328.

Figure 24A:
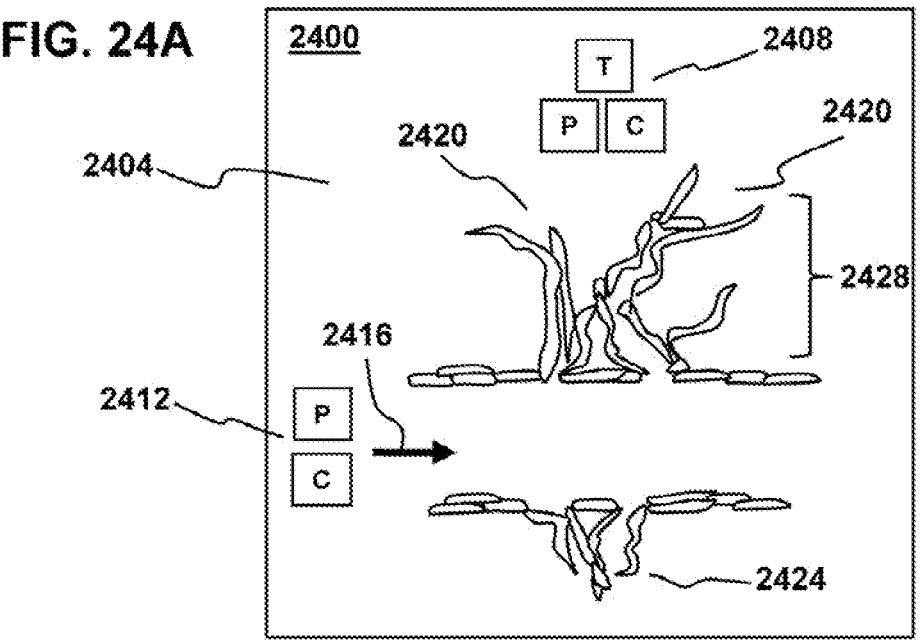
FIG. 24A schematically shows a microvessel sprouting assay with angiogenic properties from cells, products, and tissues present in higher amounts in a CPD.
Figure 24B:
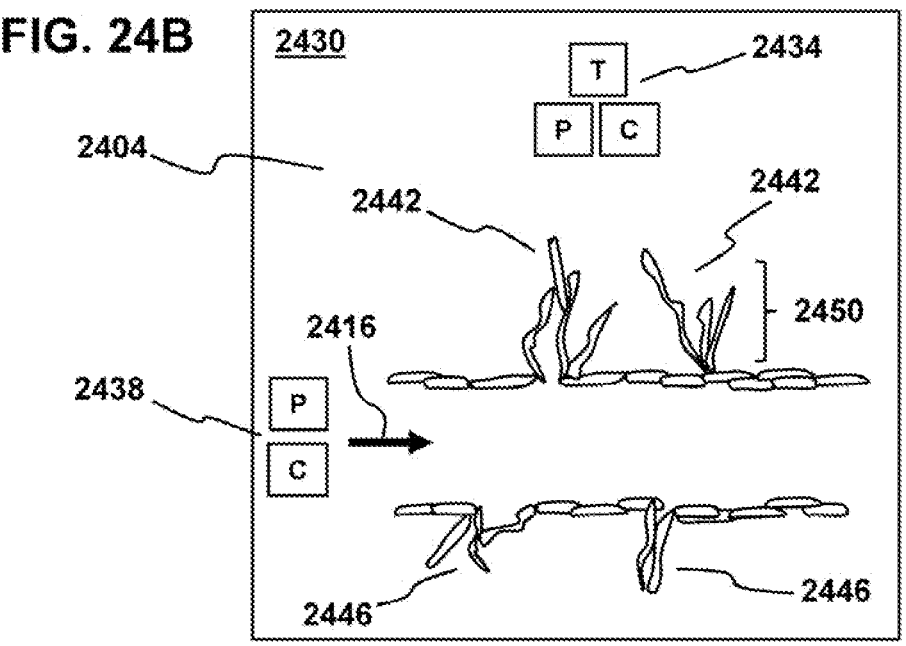
FIG. 24B schematically shows a microvessel sprouting assay with angiogenic properties from cells, products, and tissues present in higher amounts in a CPD.

Referring now to FIG. 24A and FIG. 24B jointly, the response of microvessel sprouting and network formation to added candidate cells (C), candidate products (P), and candidate tissue (T) is depicted schematically after cell seeding at a high density. A portion of a single parent microvessel is depicted for illustration purposes only. Single, double, or complex arrays of parent microvessels could be analyzed in different embodiments in a series of CPDs.

In FIG. 24A and FIG. 24B, two CPDs are schematically shown with different amounts of candidates, including candidate cells (C), products (P), or tissue (T) candidates, concentrated locally. In FIG. 24A, the CPD 2400 is shown to include a matrix 2404 with a higher amount of candidate cells (C), products (P), or tissue (T), 2408. Similarly, a higher amount of cells (C) or products (P) 2412 may be added to the perfusate 2416. After incubation with perfusion the effect of the addition of candidate (C), products (P), or tissue (T) can be assessed by measuring 2428 the length of new sprouts 2420, 2424. An angiogenic effect from locally concentrated candidates will result in increased and more robust sprouting 2420 close to the candidates being assayed, while sprouts distal to the candidates will show less growth 2424. Addition of higher amounts of cells (C) or products (P) 2412 to the perfusate would be expected to increase sprout growth on all sides of the parent vessel (not depicted). In FIG. 24B, the CPD 2430 includes a lower amount of candidate cells (C), products (P), or tissue (T) 2124, concentrated locally, or similarly with lower amounts of cells (C), or products (P) 2438 added in the perfusate 2416. The sprouts would be expected to show less growth 2450 for sprouts 2442 close to the candidates being assayed compared to CPDs with higher amounts 2400. In some cases the sprouts close 2442 and distal 2446 to the candidates may be similar in size. By assaying a broad range of amounts for candidates the angiogenic effect can be determined based on the degree of increased growth of new sprouts compared to controls.

Figure 25A:
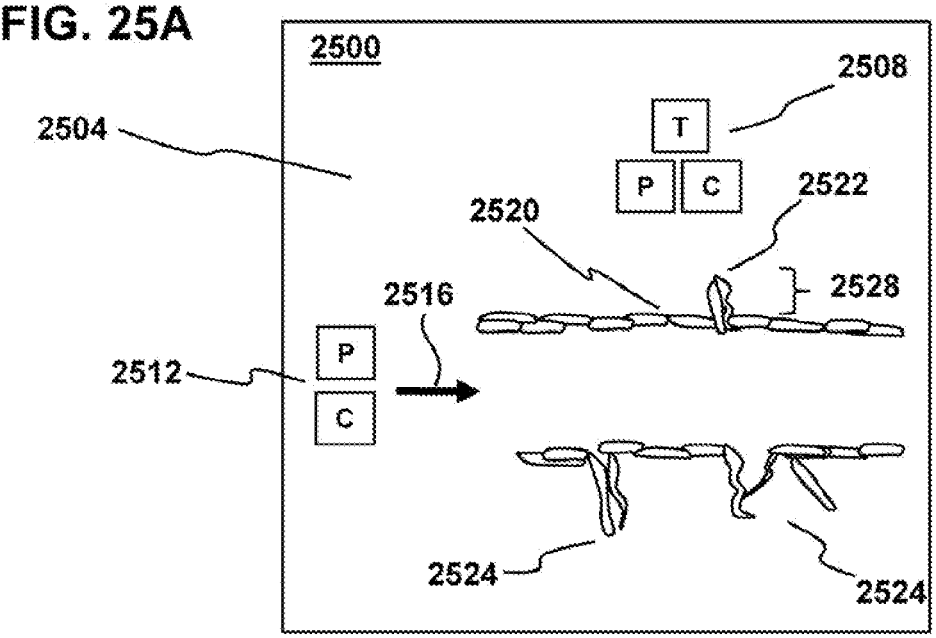
FIG. 25A schematically shows a microvessel sprouting assay with angiostatic properties from cells, products, and tissues present in higher amounts in a CPD.
Figure 25B:
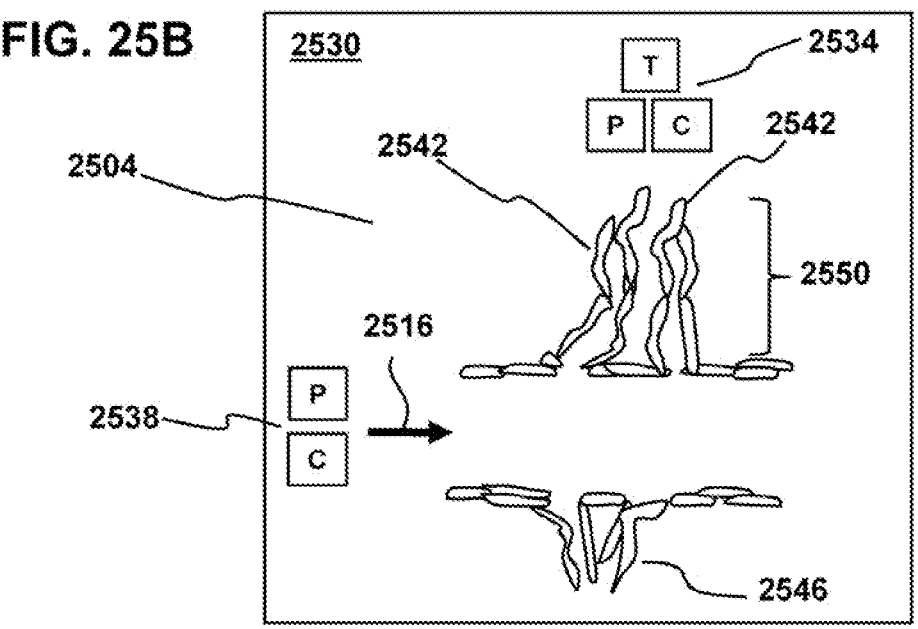
FIG. 25B schematically shows a microvessel sprouting assay with angiostatic properties from cells, products, and tissues present in lower amounts in a CPD.

Referring now to FIG. 25A and FIG. 25B jointly, two CPDs are schematically shown with different amounts of candidate cells (C), products (P), or tissue (T) candidates, concentrated locally. In FIG. 25A, the CPD 2500 is shown to include a matrix 2504 with a higher amount of candidate cells (C), products (P), or tissue (T) 2508. Similarly, a higher amount of cells (C) or products (P) 2512 may be added to the perfusate 2516. After incubation with perfusion the effect of the addition of candidate (C), products (P), or tissue (T) can be assessed by measuring 2528 the length of new sprouts, 2520, 2524. An angiostatic effect from locally concentrated candidates will result in decreased 2522 or even no sprouting 2520 close to the candidates being assayed, while sprouts distal to the candidates will show some or even normal growth 2524. Addition of higher amounts of (C) or products (P) 2512 to the perfusate would be expected to decrease sprout growth on all sides of the parent vessel (not depicted). In FIG. 25B, the CPD 2530 includes a lower amount of candidate cells (C), products (P), or tissue (T) concentrated locally 2534, or similarly with lower amounts of cells (C), or products (P) 2538 added in the perfusate 2516. The sprouts would be expected to show more normal growth 2550 for sprouts 2542 close to the candidates being assayed compared to CPDs with higher amounts 2500. In some cases the sprouts close 2542 and distal 2546 to the candidates may be similar in size indicating less or no angiostatic effect for candidates. By assaying a broad range of amounts for candidates the angiostatic effects can be determined based on the degree of inhibition of growth of new sprouts compared to controls.

In alternate embodiments increasing amounts of locally concentrated candidates could be assayed in a single CPD. Also, various combinations could be assayed in different embodiments in the microvessel formation assay. For example, only one parent vessel is depicted in the schematic, but different embodiments could have two or more parent vessels with cells (C), products (P), and tissue (T) placed at various locations in the matrix, either dispersed or locally concentrated. In alternate embodiments the cells (C), products (P), or tissue (T) could also be added at different times before and after microvessel sprouting. Also, cells (C), products (P), or tissue (T) could be added before and after the formation of complex microvessel networks between one or more parent vessels. In still further embodiments one channel could be seeded with endothelial cells to form a parent vessel while a second channel could be seeded with cancer cells or parenchymal cells or stromal cells for tissue models or tissue engineering. Further, one would recognize that a broad mix of channels could be seeded with a variety of cell types that could be assayed (e.g. ECs-arterial, ECs-venous, lymphatic ECs, parenchymal cells from liver or other tissues).

Angiogenesis Assay

Referring now jointly to FIG. 26A and FIG. 26B, shown is an embodiment mimicking cell induced angiogenesis. In FIG. 26A shown is a bright field image of two collagen channels from a CPD 2600, with one seeded with HUVECs that has formed a sprouting parent vessel 2604 and the second seeded with breast cancer cells 2608 of the BT474 cell line. The HUVEC parent vessel shows sprouts 2610, 2620, 2630, 2640 growing towards the breast cancer cells representative of angiogenic potential from bioactive products that may be released from the cancer cells. In FIG. 26B, a corresponding fluorescence microscopy image of the same microvessels is shown. The HUVECs were stained with a stain 2650 and the breast cancer were stained cells with a different cellular stain 2660 before seeding (cell tracker green CMFDA and cell tracker orange, CRMA, respectively, color not depicted). Thus, the sprouts 2610, 2620, 2630, and 2640 growing from the HUVEC parent vessel are of endothelial origin could monitored for angiogenic and angiostatic effects.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices and reconstruction algorithms, and that various modifications, both as to the equipment details and operating procedures, may be accomplished without departing from the true spirit and scope of the present invention.

The complete disclosures of all references cited in this specification are hereby incorporated by reference. In the event of an otherwise irreconcilable conflict, however, the present specification shall control.

REFERENCES

Ades, E. W., F. J. Candal, et al. (1992). "HMEC-1: establishment of an immortalized human microvascular endothelial cell line." *J Invest Dermatol* 99(6): 683-90.

Aird, W. C. (2007). "Phenotypic heterogeneity of the endothelium: II. Representative vascular beds." *Circ Res* 100(2): 174-90.

Akhtar, N., E. B. Dickerson, et al. (2002). "The sponge/Matrigel angiogenesis assay." *Angiogenesis* 5(1-2): 75-80.

Algire, G. H., H. W. Chalkley, et al. (1945). "Vascular reactions of normal and malignant tissues in vivo. I. Vascular reactions of mice to wounds and to normal and neoplastic transplants." *J Natl Cancer Inst* 6: 73-85.

Andrade, S. P., R. D. Machado, et al. (1997). "Sponge-induced angiogenesis in mice and the pharmacological reactivity of the neovasculature quantitated by a fluorimetric method." *Microvasc Res* 54(3): 253-61.

Arthur, W. T., R. B. Vernon, et al. (1998). "Growth factors reverse the impaired sprouting of microvessels from aged mice." *Microvasc Res* 55(3): 260-70.

Ausprunk, D. H., D. R. Knighton, et al. (1974). "Differentiation of vascular endothelium in the chick chorioallantois: a structural and autoradiographic study." *Dev Biol* 38(2): 237-48.

Bazzoni, G. and E. Dejana (2004). "Endothelial cell-to-cell junctions: molecular organization and role in vascular homeostasis." *Physiol Rev* 84(3): 869-901.

Bell, S. E., A. Mavila, et al. (2001). "Differential gene expression during capillary morphogenesis in 3D collagen matrices: regulated expression of genes involved in basement membrane matrix assembly, cell cycle progression, cellular differentiation and G-protein signaling." *J Cell Sci* 114 (Pt 15): 2755-73.

Benson, D. A., I. Karsch-Mizrachi, et al. (2008). "GenBank." *Nucl. Acids Res.* 36(suppl 1): D25-30.

Bouis, D., G. A. Hospers, et al. (2001). "Endothelium in vitro: a review of human vascular endothelial cell lines for blood vessel-related research." *Angiogenesis* 4(2): 91-102.

Clark, E. R. and E. L. Clark (1939). "Microscopic observations on the growth of blood capillaries in the living mammal." *Am J Anat* 64: 251-301.

Davis, G. E., K. J. Bayless, et al. (2002). "Molecular basis of endothelial cell morphogenesis in three-dimensional extracellular matrices." *Anat Rec* 268(3): 252-75.

Davis, G. E. and C. W. Camarillo (1996). "An alpha 2 beta 1 integrin-dependent pinocytic mechanism involving intracellular vacuole formation and coalescence regulates capillary lumen and tube formation in three-dimensional collagen matrix." *Exp Cell Res* 224(1): 39-51.

Edgell, C. J., C. C. McDonald, et al. (1983). "Permanent cell line expressing human factor VIII-related antigen established by hybridization." *Proc Natl Acad Sci USA* 80(12): 3734-7.

Elsdale, T. and J. Bard (1972). "Collagen substrate for studies on cell behavior." *J Cell Biol* 54(3): 626-37.

Feder, J., S. C. Marasa, et al. (1983). "The formation of capillary-like tubes by calf aortic endothelial cells grown in vitro." *J Cell Physiol* 116(1): 1-6.

Fishman, J. A., G. B. Ryan, et al. (1975). "Endothelial regeneration in the rat carotid artery and the significance of endothelial denudation in the pathogenesis of myointimal thickening." *Lab Invest* 32(3): 339-51.

Folkman, J. and C. Haudenschild (1980). "Angiogenesis in vitro." *Nature* 288(5791): 551-6.

Folkman, J., C. C. Haudenschild, et al. (1979). "Long-term culture of capillary endothelial cells." *Proc Natl Acad Sci USA* 76(10): 5217-21.

Frerich, B., N. Lindemann, et al. (2001). "In vitro model of a vascular stroma for the engineering of vascularized tissues." *Int J Oral Maxillofac Surg* 30(5): 414-20.

Frerich, B., K. Zuckmantel, et al. (2008). "Maturation of capillary-like structures in a tube-like construct in perfusion and rotation culture." *Int J Oral Maxillofac Surg* 37(5): 459-66.

Gale, N. W., P. Baluk, et al. (2001). "Ephrin-B2 selectively marks arterial vessels and neovascularization sites in the adult, with expression in both endothelial and smooth-muscle cells." *Dev Biol* 230(2): 151-60.

Gerety, S. S., H. U. Wang, et al. (1999). "Symmetrical mutant phenotypes of the receptor EphB4 and its specific transmembrane ligand ephrin-B2 in cardiovascular development" *Mol Cell* 4(3): 403-14.

Gimbrone, M. A., Jr. (1976). Culture of vascular endothelium. *Prog Hemost Thromb.* 3: 1-28.

Gimbrone, M. A., Jr., R. S. Cotran, et al. (1974). "Human vascular endothelial cells in culture. Growth and DNA synthesis." *J Cell Biol* 60(3): 673-84.

Gimbrone, M. A., Jr., R. S. Cotran, et al. (1974). "Tumor growth and neovascularization: an experimental model using the rabbit cornea." *J Natl Cancer Inst* 52(2): 413-27.

Greenblatt, M. and P. Shubi (1968). "Tumor angiogenesis: transfilter diffusion studies in the hamster by the transparent chamber technique." *J Natl Cancer Inst* 41(1): 111-24.

Hiraoka, N., E. Allen, et al. (1998). "Matrix metalloproteinases regulate neovascularization by acting as pericellular fibrinolysins." *Cell* 95(3): 365-77.

Hohenwarter, O., A. Jakoubek, et al. (1994). "Expression of SV40 tumour antigens enables human endothelial cells to grow independently from foetal calf serum and exogenous growth factors." *J Biotechnol* 34(2): 205-11.

Hotary, K., E. Allen, et al. (2000). "Regulation of cell invasion and morphogenesis in a three-dimensional type I collagen matrix by membrane-type matrix metalloproteinases 1, 2, and 3." *J Cell Biol* 149(6): 1309-23.

Hoying, J. B., C. A. Boswell, et al. (1996). "Angiogenic potential of microvessel fragments established in three-dimensional collagen gels." *In Vitro Cell Dev Biol Anim* 32(7): 409-19.

Jaffe, E. A., R. L. Nachman, et al. (1973). "Culture of human endothelial cells derived from umbilical veins. Identification by morphologic and immunologic criteria." *J Clin Invest* 52(11): 2745-56.

Jozaki, K., P. T. Marucha, et al. (1990). "An in vitro model of cell migration: evaluation of vascular endothelial cell migration." *Anal Biochem* 190(1): 39-47.

Kang, J. and I. Lee (2006). "TuJ1 (class III beta-tubulin) as phenotypic marker of lymphatic and venous valves." *Cardiovasc Pathol* 15(4): 218-21.

Koike, T., R. B. Vernon, et al. (2003). "Inhibited angiogenesis in aging: a role for TIMP-2." *J Gerontol A Biol Sci Med Sci* 58(9): B798-805.

Krebs, L. T., Y. Xue, et al. (2000). "Notch signaling is essential for vascular morphogenesis in mice." *Genes Dev* 14(11): 1343-52.

Kubota, Y., H. K. Kleinman, et al. (1988). "Role of laminin and basement membrane in the morphological differentiation of human endothelial cells into capillary-like structures." *J Cell Biol* 107(4): 1589-98.

Kuzuya, M. and J. L. Kinsella (1994). "Induction of endothelial cell differentiation in vitro by fibroblast-derived soluble factors." *Exp Cell Res* 215(2): 310-8.

Lindner, V., C. Booth, et al. (2001). "Members of the Jagged/Notch gene families are expressed in injured arteries and regulate cell phenotype via alterations in cell matrix and cell-cell interaction." *Am J Pathol* 159(3): 875-83.

Lindsell, C. E., J. Boulter, et al. (1996). "Expression patterns of Jagged, Delta1, Notch1, Notch2, and Notch3 genes identify ligand-receptor pairs that may function in neural development." *Mol Cell Neurosci* 8(1): 14-27.

Maciag, T., J. Kadish, et al. (1982). "Organizational behavior of human umbilical vein endothelial cells." *J Cell Biol* 94(3): 511-20.

Madri, J. A. (1982). "Endothelial cell-matrix interactions in hemostasis." *Prog Hemost Thromb* 6: 1-24.

Madri, J. A. and B. M. Pratt (1986). "Endothelial cell-matrix interactions: in vitro models of angiogenesis." *J Histochem Cytochem* 34(1): 85-91.

Madri, J. A., B. M. Pratt, et al. (1988). "Phenotypic modulation of endothelial cells by transforming growth factor-beta depends upon the composition and organization of the extracellular matrix." *J Cell Biol* 106(4): 1375-84.

Madri, J. A. and K. S. Stenn (1982). "Aortic endothelial cell migration. I. Matrix requirements and composition." *Am J Pathol* 106(2): 180-6.

Manoussaki, D., S. R. Lubkin, et al. (1996). "A mechanical model for the formation of vascular networks in vitro." *Acta Biotheor* 44(3-4): 271-82.

Marx, M., R. A. Perlmutter, et al. (1994). "Modulation of platelet-derived growth factor receptor expression in microvascular endothelial cells during in vitro angiogenesis." *J Clin Invest* 93(1): 131-9.

Merwin, J. R., J. M. Anderson, et al. (1990). "Transforming growth factor beta 1 modulates extracellular matrix organization and cell-cell junctional complex formation during in vitro angiogenesis." *J Cell Physiol* 142(1): 117-28.

Montesano, R. and L. Orci (1985). "Tumor-promoting phorbol esters induce angiogenesis in vitro." *Cell* 42(2): 469-77.

Montesano, R., L. Orci, et al. (1983). "In vitro rapid organization of endothelial cells into capillary-like networks is promoted by collagen matrices." *J Cell Biol* 97(5 Pt 1): 1648-52.

Montesano, R., M. S. Pepper, et al. (1993). "Paracrine induction of angiogenesis in vitro by Swiss 3T3 fibroblasts." *J Cell Sci* 105 (Pt 4): 1013-24.

Mori, M., Y. Sadahira, et al. (1988). "Capillary growth from reversed rat aortic segments cultured in collagen gel." *Acta Pathol Jpn* 38(12): 1503-12.

Mukouyama, Y. S., H. P. Gerber, et al. (2005). "Peripheral nerve-derived VEGF promotes arterial differentiation via neuropilin 1-mediated positive feedback." *Development* 132(5): 941-52.

Nakagawa, O., M. Nakagawa, et al. (1999). "HRT1, HRT2, and HRT3: a new subclass of bHLH transcription factors marking specific cardiac, somitic, and pharyngeal arch segments." *Dev Biol* 216(1): 72-84.

Nehls, V. and D. Drenckhahn (1995). "A novel, microcarrier-based in vitro assay for rapid and reliable quantification of three-dimensional cell migration and angiogenesis." *Microvasc Res* 50(3): 311-22.

Nehls, V. and R. Herrmann (1996). "The configuration of fibrin clots determines capillary morphogenesis and endothelial cell migration." *Microvasc Res* 51(3): 347-64.

Nicosia, R. F., E. Bonanno, et al. (1994). "Modulation of angiogenesis in vitro by laminin-entactin complex." *Dev Biol* 164(1): 197-206.

Nicosia, R. F., E. Bonanno, et al. (1992). "Large-vessel endothelium switches to a microvascular phenotype during angiogenesis in collagen gel culture of rat aorta." *Atherosclerosis* 95(2-3): 191-9.

Nicosia, R. F., S. V. Nicosia, et al. (1994). "Vascular endothelial growth factor, platelet-derived growth factor, and insulin-like growth factor-1 promote rat aortic angiogenesis in vitro." *Am J Pathol* 145(5): 1023-9.

Nicosia, R. F. and A. Ottinetti (1990). "Modulation of microvascular growth and morphogenesis by reconstituted basement membrane gel in three-dimensional cultures of rat aorta: a comparative study of angiogenesis in matrigel, collagen, fibrin, and plasma clot." *In Vitro Cell Des Biol* 26(2): 119-28.

Nicosia, R. F., R. Tchao, et al. (1982). "Histotypic angiogenesis in vitro: light microscopic, ultrastructural, and radioautographic studies." *In Vitro* 18(6): 538-49.

Nicosia, R. F., R. Tchao, et al. (1983). "Angiogenesis-dependent tumor spread in reinforced fibrin clot culture." *Cancer Res* 43(5): 2159-66.

Nicosia, R. F. and G. P. Tuszynski (1994). "Matrix-bound thrombospondin promotes angiogenesis in vitro." *J Cell Biol* 124(1-2): 183-93.

Passaniti, A., R. M. Taylor, et al. (1992). "A simple, quantitative method for assessing angiogenesis and antiangiogenic agents using reconstituted basement membrane, heparin, and fibroblast growth factor." *Lab Invest* 67(4): 519-28.

Pepper, M. S., R. Montesano, et al. (1991). "Chondrocytes inhibit endothelial sprout formation in vitro: evidence for involvement of a transforming growth factor-beta." *J Cell Physiol* 146(1): 170-9.

Rosen, E. M., L. Meromsky, et al. (1990). "Quantitation of cytokine-stimulated migration of endothelium and epithelium by a new assay using microcarrier beads." *Exp Cell Res* 186(1): 22-31.

Sage, E. H. and R. B. Vernon (1994). "Regulation of angiogenesis by extracellular matrix: the growth and the glue." *J Hypertens Suppl* 12(10): S145-52.

Seki, T., J. Yun, et al. (2003). "Arterial endothelium-specific activin receptor-like kinase 1 expression suggests its role in arterialization and vascular remodeling." *Circ Res* 93(7): 682-9.

Shin, D. and D. J. Anderson (2005). "Isolation of arterial-specific genes by subtractive hybridization reveals molecular heterogeneity among arterial endothelial cells." *Dev Dyn* 233(4): 1589-604.

Takahashi, K., Y. Sawasaki, et al. (1990). "Spontaneous transformation and immortalization of human endothelial cells." *In Vitro Cell Dev Biol* 26(3 Pt 1): 265-74.

Tian, H., S. L. McKnight, et al. (1997). "Endothelial PAS domain protein 1 (EPAS1), a transcription factor selectively expressed in endothelial cells." *Genes Dev* 11(1): 72-82.

Torres-Vázquez, J., M. Kamei, et al. (2003). "Molecular distinction between arteries and veins." *Cell and Tissue Research* 314(1): 43-59.

Uyttendaele, H., V. Closson, et al. (2000). "Notch4 and Jagged-1 induce microvessel differentiation of at brain endothelial cells." *Microvasc Res* 60(2): 91-103.

Vernon, R. B., J. C. Angello, et al. (1992). "Reorganization of basement membrane matrices by cellular traction promotes the formation of cellular networks in vitro." *Lab Invest* 66(5): 536-47.

Vernon, R. B. and M. D. Gooden (2002). "New technologies in vitro for analysis of cell movement on or within collagen gels." *Matrix Biol* 21(8): 661-9.

Vernon, R. B., S. L. Lara, et al. (1995). "Organized type I collagen influences endothelial patterns during "spontaneous angiogenesis in vitro": planar cultures as models of vascular development." *In Vitro Cell Dev Biol Anim* 31(2): 120-31.

Vernon, R. B. and E. H. Sage (1999). "A novel, quantitative model for study of endothelial cell migration and sprout formation within three-dimensional collagen matrices." *Microvasc Res* 57(2): 118-33.

Villaschi, S. and R. F. Nicosia (1993). "Angiogenic role of endogenous basic fibroblast growth factor released by rat aorta after injury." *Am J Pathol* 143(1): 181-90.

Wheelock, M. J. and K. R. Johnson (2003). "CADHERINS AS MODULATORS OF CELLULAR PHENOTYPE." *Annual Review of Cell and Developmental Biology* 19(1): 207-235.

You, L. R., F. J. Lin, et al. (2005). "Suppression of Notch signaling by the COUP-TFII transcription factor regulates vein identity." *Nature* 435(7038): 98-104.

Yuan, L., D. Moyon, et al. (2002). "Abnormal lymphatic vessel development in neuropilin 2 mutant mice." *Development* 129(20): 4797-806.

Zimrin, A. B., M. S. Pepper, et al. (1996). "An antisense oligonucleotide to the notch ligand jagged enhances fibroblast growth factor-induced angiogenesis in vitro." *J Biol Chem* 271(51): 32499-502.

What is claimed is:

1. A method for forming networks of perfusable microvessels in vitro comprising the steps of:
    seeding cells of at least one cell type capable of sprouting into at least one channel within a matrix;
    activating the competency of the at least one cell type for sprouting as microvessels from parent vessels, wherein the competency for sprouting is triggered from the density of seeding;
    perfusing the at least one channel with at least one medium to allow the at least one cell type to form at least one parent vessel;
    incubating and perfusing the at least one parent vessel to maintain viability and provide for sprouting of microvessels from the at least one parent vessel into the surrounding matrix; and
    growing the sprouting microvessels until the microvessels have formed networks.

2. The method of claim 1 wherein the competency of the at least one cell type for sprouting results from cellular signaling activated from contacts between cells.

3. The method of claim 1 wherein the competency of the at least one cell type for sprouting results from cellular signaling activated from both contacts between cells and from contacts between cells and the matrix.

4. The method of claim 1 wherein the competency of the at least one cell type for sprouting results from cellular signaling selected from the group consisting of cell-cell mediated contacts, cell-matrix mediated contacts, and growth factor-cell mediated contacts.

5. The method of claim 1 wherein the majority of cells are in cell to cell contact with each other.

6. The method of claim 1 wherein the majority of cells are almost in cell to cell contact with each other.

7. The method of claim 1 wherein the cells have a density of at least 250 cells per sq. mm of channel.

8. The method of claim 1 wherein the cells have a density from 250 to 2000 cells per sq. mm of channel.

9. The method of claim 1 wherein the microvessels sprouting from parent vessels anastomoze to form the microvessel networks.

10. The method of claim 1 wherein the parent vessels support growth of at least one cell type of a tissue embedded within the matrix.

11. The method of claim 10 wherein the parent vessels are 3D arrays of parent vessels.

12. The method of claim 1 wherein the at least one cell type comprises endothelial cells.

13. The method of claim 1 wherein monitoring the networks of microvessels is used to screen for angiogenic and angiostatic factors in the matrix, wherein increased growth of the network indicates an angiogenic factor and decreased growth of the network indicates an angiostatic factor.

14. The method of claim 1 wherein monitoring the networks of microvessels is used to screen for angiogenic and angiostatic factors in the perfusate medium, wherein increased growth of the network indicates an angiogenic factor and decreased growth of the network indicates an angiostatic factor.

15. The method of claim 1 wherein the at least one channel in the matrix is formed with a mandrel.

16. The method of claim 15 wherein the mandrels is removed by extraction.

17. The method of claim 15 wherein the mandrel is removed by decomposing.

18. The method of claim 1 wherein the seeding of the at least one channel is by a process selected from the group consisting of injection of cells into the matrix channel, and prior attachment of cells to the mandrel, and by a combination of prior attachment of cells to the mandrel and injection of cells into the matrix channel.

19. The method of claim 1 wherein the at least one channel in the matrix is from 20 micron to 500 microns in diameter.

20. The method of claim 1 wherein the at least one channel in the matrix is from 500 microns to 5.5 mm in diameter.

21. The method of claim 1 wherein the matrix comprises material selected from the group consisting of fibrin, collagen, collagen sub-types, gelatin, gelled basement membrane, agar, agarose, alginate, basement membrane proteins, extracellular matrix proteins, silica gel, and cells.

22. The method of claim 21 wherein the basement membrane proteins are chosen from the group consisting of collagen type IV, perlecan, laminin, integrins, enactins, dystroglycans, type VII collagen fibers, and collagen type VII microfibrils.

23. The method of claim 21 wherein the extra cellular matrix proteins are selected from the group consisting of proteoglycans, glycosaminoglycans, heparin sulfate proteoglycans, chondroitin sulfate proteoglycans, keratin sulfate proteoglycans, hyaluronic acid, collagen, fibronectin, vitronectin, elastin, and laminin.

24. The method of claim 1 wherein the matrix further comprises growth factors.

25. The method of claim 1 wherein increased growth of the microvessel network indicates an angiogenic factor is being secreted from the cells and decreased growth of the microvessel network indicates an angiostatic factor is being secreted from the cells.

26. The method of claim 1 wherein at least one tissue is embedded into the matrix.

27. The method of claim 26 wherein the at least one tissue is chosen from the group consisting of healthy tissue, diseased tissue, cancerous tissue, and genetically engineered tissue.

28. The method of claim 26 wherein increased growth of the microvessel network indicates an angiogenic factor is being secreted from the tissue and decreased growth of the microvessel network indicates an angiostatic factor is being secreted from the tissue.

29. The method of claim 1 wherein the flow of the at least one perfusate medium approximates in vivo flow of capillary vessels.

30. The method of claim 1 wherein the flow of the at least one perfusate medium preferentially flows through the microvessel network connecting parent vessels by decreasing the flow into one parent vessel and increasing the resistance in another parent vessel.

31. The method of claim 1 wherein the at least one perfusate medium comprises a cellular growth medium that has supplemental components selected from the group consisting of angiogenic factors, angiostatic factors, serum, phorbel esters, and growth factors.

32. The method of claim 31 wherein oxygenation of the at least one perfusate medium is substantially by diffusion through the matrix.

33. The method of claim 1 wherein the at least one medium comprises growth factors.

* * * * *